United States Patent [19]
Ogata et al.

[11] Patent Number: 5,110,956
[45] Date of Patent: May 5, 1992

[54] BENZODIOXALE DERIVATIVES

[75] Inventors: Yoshitake Ogata; Makoto Ikeda, both of Tsukuba; Seiichiro Nomoto, Ushiku; Makoto Okita, Tsukuba; Naoyuki Shimomura, Tsukuba; Toshihiko Kaneko, Tsukuba; Takashi Yamanaka, Tsukuba; Ieharu Hishinuma, Kitasouma; Junichi Nagakawa, Tsukuba; Kazuo Hirota, Tsukuba; Kaname Miyamoto, Tsukuba; Toru Horie, Tsukuba; Tsuneo Wakabayashi, Mito, all of Japan

[73] Assignee: Eisai Co., Ltd., Tokyo, Japan

[21] Appl. No.: 517,444

[22] Filed: Apr. 23, 1990

Related U.S. Application Data

[63] Continuation of Ser. No. 160,333, Feb. 25, 1988, abandoned.

[30] Foreign Application Priority Data

Mar. 4, 1987 [JP] Japan .................. 62-49141
Apr. 3, 1987 [JP] Japan .................. 62-82258
Apr. 27, 1987 [JP] Japan .................. 62-103724
Apr. 28, 1987 [JP] Japan .................. 62-105508
Apr. 28, 1987 [JP] Japan .................. 62-105509
Sep. 28, 1987 [JP] Japan .................. 62-243492

[51] Int. Cl.$^5$ .................. C07D 317/54; C07D 277/30
[52] U.S. Cl. .................. 549/447; 544/333; 544/335; 546/256; 546/270; 548/204; 548/214; 548/236; 548/248; 548/336; 548/374
[58] Field of Search .............. 549/447; 544/333, 335; 546/256, 270; 548/204, 214, 236, 248, 336, 374

[56] References Cited

U.S. PATENT DOCUMENTS 3,852,439 12/1974 Hennart et al.

FOREIGN PATENT DOCUMENTS 62-29522 2/1987 Japan .
62-39583 2/1987 Japan .

Primary Examiner—Nicky Chan
Attorney, Agent, or Firm—Birch, Stewart, Kolasch & Birch

[57] ABSTRACT

A new benzodioxole derivative has a substituent in the phenyl ring which is a carboxyalkylthioalkyl or the like and is effective to treat a liver disease.

4 Claims, No Drawings

BENZODIOXALE DERIVATIVES

This application is a continuation of application Ser. No. 07/160,333 filed on Feb. 25, 1988, now abandoned.

The invention relates to a benzodioxole derivative, a pharmacologically acceptable salt thereof, a pharmaceutical composition containing the same, a process for preparing the same and the medical treatment of liver troubles therewith. The invention compound exhibits an excellent activity as a medicine for liver troubles such as liver diseases of the human being and liver injury of animals.

STATEMENT OF PRIOR ARTS

The development of a liver trouble remedy is very difficult, because the cause, figure and pathophysiology of liver troubles are various and mostly unobvious.

Representative medicines which are widely used in the treatment and prevention of liver troubles and evaluated to be clinically effective include glycyrrhizin preparations. Although the glycyrrhizin preparations are generally believed to be effective in the treatment of a liver affection, cirrhosis and hepatitis and in the protection of a liver after a surgical operation, however, none of the preparations exhibit a sufficient effect and they are further problematic in that they cause a steroidal adverse reaction. Further, the glycyrrhizin preparations are disadvantageous in that the oral administration thereof is ineffective, though they can be administered as intravenous injections to give an effect.

Under these circumstances, it is strongly desired to develop an excellent medicine which is excellent in safety and can be orally administered to exhibit an excellent effect.

Under these circumstances, the inventors of the present invention have eagerly studied to develop a new liver trouble remedy.

The inventors of the present invention have long studied plants which have been used as folk medicines and have found 2-[(phenylmethyl)trithiojethanol (A) and cubebin (B) which are represented by the general formulas:

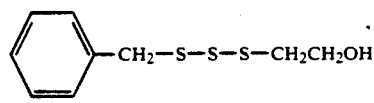
(A)

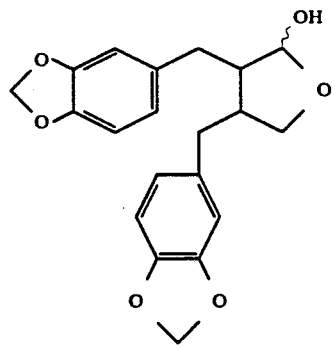
(B)

and are active compounds effective as liver trouble remedies, from *Petiveria alliacea* L. and *Cinnamonum porrectum* (Roxb.) Kosterm.

Thereafter, the inventors of the present invention have synthesized various compounds by using the above compounds as basic compounds and have examined the obtained compounds for pharmacological activity. As a result of the examination, they have found that benzodioxole derivatives represented by the general formula (I) or pharmacologically acceptable salts thereof exhibit higher safety and are useful as a more excellent liver trouble remedy. The present invention has been accomplished on the basis of this finding.

The following two patent publications show liver trouble remedies which are different from the benzodioxole derivatives of the present invention in chemical structure.

More precisely, the compounds disclosed in Japanese Patent Laid-Open No. 29522/1987 have each a structure comprising a benzodioxole ring and a saturated alkyl group bonded to the phenyl ring of the benzodioxole ring and most of them have already been known.

Further, Japanese Patent Laid-Open No. 39583/1987 discloses (1,3-benzodioxol-5-yl)methylthio derivatives. However, the group bonded to the S atom of these derivatives is a heterocyclic group such as pyridine, pyrimidine or thiadiazole, so that the derivatives are clearly different from the compounds of the present invention in structure.

As described above, the present invention has been accomplished on the basis of a hint taken from the compounds (A) and (B) found by the inventors of the present invention themselves from plant components and therefore is different from the inventions of the above two Laid-Open, Patents in conception. Accordingly, the compounds of the present invention are different from those of the above two Laid-Open Patents in chemical structure.

SUMMARY OF THE INVENTION

The invention provides a novel benzodioxole derivative having the formula [I] and a pharmacologically acceptable salt thereof:

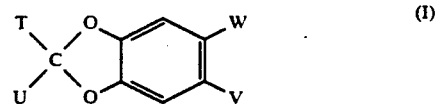
(I)

in which T, U, V and W are each defined according to the below shown respective six groups (a) to (f):

(a) T is hydrogen, U is hydrogen, V is R3 and W is

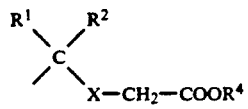

wherein $R^1$ and $R^2$ may be the same or different from each other and each represents a hydrogen atom or an alkyl, arylalkyl or heteroarylalkyl group, $R^3$ represents a hydrogen atom or a lower alkyl, arylalkyl or heterocarylalkyl group, $R^4$ represents a hydrogen atom or a lower alkyl group, or $R^2$ and $R^3$ may form together an at least 4-membered ring and X represents a group of the formula:

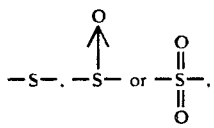

with the proviso that $R^1$ is an alkyl, arylalkyl or heteroarylalkyl group having at least 3 carbon atoms when X is a —S— group and $R^3$ and $R^2$ are each a hydrogen atom;

(b) T is hydrogen, U is hydrogen, V is hydrogen and W is $-(CH_2)_2-X-R$
wherein X represents a group of the formula:

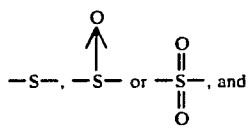

R represents:

(1) a hydrogen atom or a lower alkyl group, (2) a group of the formula: $-(CH_2)_n-COOR^1$ in which n represents an integer of 1 to 5 and $R^1$ represents a hydrogen atom or a lower alkyl group, (3) a group of the formula: $-(CH_2)_n-OR^2$ in which n represents an integer of 1 to 5 and $R^2$ represents a hydrogen atom, a lower alkyl group or an acyl group, (4) a group of the formula:

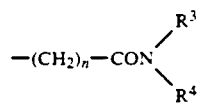

in which n represents an integer of 1 to 5, and $R^3$ and $R^4$, which may be the same or different from each other, each represents a hydrogen atom, a lower alkyl or carboxymethyl group, (5) a group of the formula:

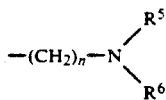

in which n represents an integer of 1 to 5, and $R^5$ and $R^6$, which may be the same or different from each other, each represents a hydrogen atom or a lower alkyl group, (6) a group of the formula:

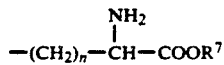

in which n represents an integer of 1 to 5 and $R^7$ represents a hydrogen atom or a lower alkyl group, (7) a group of the formula shown in the above item (2) but wherein one or more carbon atoms of the alkylene chain having n carbon atoms are bonded with a lower alkyl group or a group of the formula: $-COOR^8$ in which $R^8$ represents a hydrogen atom or a lower alkyl group, in place of hydrogen atom, (8) a group of the formula shown in the above item (3) but wherein one or more carbon atoms of the alkylene chain having n carbon atoms are bonded with a hydroxyl group in place of hydrogen atom, or (9) a group of the formula:

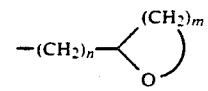

in which n represents an integer of 1 to 5 and m represents an integer of 3 or 4, with the proviso that when X represents a group of the formula: —S— and R represents a lower alkyl group, the lower alkyl group cannot be a methyl group;

(c) T is hydrogen, U is hydrogen, V is R1 and W is

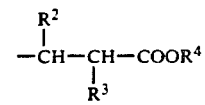

wherein $R^1$ represents a hydrogen atom or a lower alkyl or lower alkoxy-lower alkyl group, $R^2$ represents a hydrogen atom or a lower alkyl or lower alkoxy group, $R^3$ represents a hydrogen atom or a lower alkyl group and $R^4$ represents a hydrogen atom or a lower alkyl group, or $R^1$ and $R^2$ or $R^1$ and $R^3$ may form together a 5- to 7-membered ring, with the proviso that all of $R^1$, $R^2$ and $R^3$ cannot be hydrogen atoms at the same time;

(d) T is R4, U is R5, V is R3 and W is

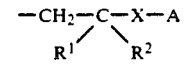

wherein $R^1$ and $R^2$ may be the same or different from each other and each represents a hydrogen atom or a lower alkyl group, $R^3$ represents a hydrogen atom, a lower alkyl group or a group of the formula: $-(CH_2)_nCOOH$ in which n represents an integer of 1 to 3, $R^4$ and $R^5$ may be the same or different from each other and each represents a hydrogen atom or a lower alkyl group, X represents a group of the

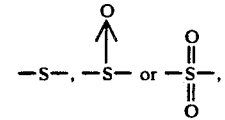

A represents a lower alkyl group, a group of the formula: $-(CH_2)_{n'}-Het$ in which n' represents an integer of 1 to 3 and Het represents a substituted or unsubstituted heterocyclic ring, a group of the formula:

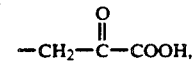

a group of the formula:

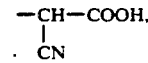

a group of the formula:

$$-\underset{\underset{R^6}{|}}{\overset{\overset{R^7}{|}}{C}}-COOH$$

in which $R^6$ and $R^7$ may be the same or different from each other and each represents a hydrogen atom or a lower alkyl group, a group of the formula: —CH$_2$—CN, a group of the formula:

$$-CH_2-\overset{\overset{O}{\|}}{C}-R^8$$

in which $R^8$ represents a lower alkyl group or a group of the formula:

$$(CH_2)_p-SO_2-N\overset{R^9}{\underset{R^{10}}{<}}$$

in which p represents an integer of 1 to 3 and $R^9$ and $R^{10}$ may be the same or different from each other and each represents a lower alkyl group;

(e) T is hydrogen, U is hydrogen, V is hydrogen and W is $$-X-S-S-\underset{\underset{R^1}{|}}{CH}-CH_2Y$$

wherein X is a group of the formula: —CH$_2$—, —CH$_2$—CH$_2$—, —CH—CH$_2$—CH$_2$— or —CH$_2$—, —CH$_2$—CH$_2$—, —CH$_2$—CH$_2$—CH$_2$— or $$-CH_2-\underset{\underset{CH_3}{|}}{CH}-;$$

$R^1$ is a hydrogen atom or a lower alkyl group and Y is hydrogen atom or an alkyl, hydroxyl, carboxyl, aryl or heteroarylcarbonyloxy group, and (f) T is hydrogen, U is hydrogen, V is $R^3$ and W is $$\underset{R^1}{\overset{}{\diagdown}}\underset{}{\overset{R^2}{\diagup}}\\-C\\\diagdown\\(CH_2)_n-S-CH_2-Y$$

wherein $R^1$ and $R^2$ may be the same or different from each other and each represents a hydrogen atom or a lower alkyl, aryl or arylalkyl group; n represents an integer of 0 or 1; Y represents a group of the formula: —COOH or $$-CON\overset{R^4}{\underset{R^5}{<}}$$

wherein $R^4$ and $R^5$ may be the same as or different from each other and each represents a hydrogen atom or a lower alkyl or carboxymethyl group and $R^3$ represents a hydrogen atom or a lower alkyl or arylalkyl group.

In addition, the invention provides a process for preparing the above shown benzodioxole derivative and a pharmaceutical composition containing it and a pharmacologically acceptable carrier.

The invention compound [I]consists of six compound groups (I-a), (I-b), (I-c), (I-d), (I-e) and (I-f). Each group is defined below, corresponding to the six group definitions (a), (h), (c), (d), (e) and (f) of T, U, V and W of the formula [I], respectively.

Compound Group (I-a)

The compound group (I-a) has the formula (I-a):

(I-a)

wherein $R^1$ and $R^2$ may be the same or different from each other and each represents a hydrogen atom or an alkyl, arylalkyl or heteroarylalkyl group, $R^3$ represents a hydrogen atom or a lower alkyl, arylalkyl or heteroarylalkyl group, $R^4$ represents a hydrogen atom or a lower alkyl group, or $R^2$ and $R^3$ may form together an at least 4-membered ring and X represents a group of the formula:

$$-S-, \ -\overset{\overset{O}{\uparrow}}{S}- \ \text{or} \ -\overset{\overset{O}{\|}}{\underset{\underset{O}{\|}}{S}}-,$$

with the proviso that $R^1$ is an alkyl, arylalkyl or heteroarylalkyl group having at least 3 carbon atoms when X is a —S— group and $R^3$ and $R^2$ are each a hydrogen atom.

In the formula (I-a), the alkyl for R1 and R2 includes a straight or branched alkyl, such as methyl, ethyl, n-propyl, n-butyl, iso-propyl, iso-butyl, 1-methylpropyl, tert-butyl, n-pentyl, 1-ethylpropyl, isoamyl, n-hexyl, n-heptyl, n-octyl, n-nonyl and n-decyl. Methyl, ethyl, n-propyl, iso-propyl and n-butyl are preferable. The lower for $R^3$ and $R^4$ includes a straight or branched alkyl having 1 to 6 carbon atoms, such as methyl, ethyl, n-propyl, n-butyl, iso-propyl, iso-butyl, 1-methylpropyl, tert-butyl, n-pentyl, 1-ethylpropyl, iso-amyl and n-hexyl. Methyl, ethyl and n-propyl are preferable. The arylalkyl for R1, $R^2$ and $R^3$ includes benzyl and phenethyl. The heteroarylalkyl for the same includes a heterocyclic ring connected with an alkyl such as methyl, ethyl and propyl. The heteroaryl includes a five- or six-membered ring having nitrogen such as pyridine, pyrimidine, pyrrole, pyrazole and imidazole, thiazole, oxazole. A preferable hetero-arylalkyl is pyridylmethyl, pyrimidylmethyl or furylmethyl, the alkyl being connected with the hetero-cyclic ring at any position. R2 and R3 may form a 4- or more membered cyclic ring together in combination. This is supported by Examples 15 and 17.

Compound Group (I-b)

The compound group (I-b) has the formula (I-b):

(I-b)

wherein X represents a group of the formula:

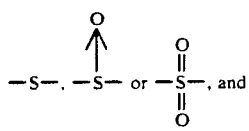

R represents:
(1) a hydrogen atom or a lower alkyl group,
(2) a group of the formula: $-(CH_2)_n-COOR^1$ in which n represents an integer of 1 to 5 and $R^1$ represents a hydrogen atom or a lower alkyl group,
(3) a group of the formula: $-(CH_2)_n-OR^2$ in which n represents an integer of 1 to 5 and $R^2$ represents a hydrogen atom, a lower alkyl group or an acyl group,
(4) a group of the formula:

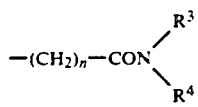

in which n represents an integer of 1 to 5, and $R^3$ and $R^4$, which may be the same or different from each other, each represents a hydrogen atom, a lower alkyl or carboxymethyl group,
(5) a group of the formula:

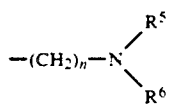

in which n represents an integer of 1 to 5, and $R^5$ and $R^6$, which may be the same or different from each other, each represents a hydrogen atom or a lower alkyl group,
(6) a group of the formula:

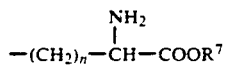

in which n represents an integer of 1 to 5 and $R^7$ represents a hydrogen atom or a lower alkyl group,
(7) a group of the formula shown in the above item (2) but wherein one or more carbon atoms of the alkylene chain having n carbon atoms are bonded with a lower alkyl group or a group of the formula: $-COOR^8$ in which $R^8$ represents a hydrogen atom or a lower alkyl group, in place of hydrogen atom,
(8) a group of the formula shown in the above item (3) but wherein one or more carbon atoms of the alkylene chain having n carbon atoms are bonded with a hydroxyl group in place of hydrogen atom, or
(9) a group of the formula:

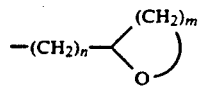

in which n represents an integer of 1 to 5 and m represents an integer of 3 or 4, with the proviso that when X represents a group of the formula: $-S-$ and R represents a lower alkyl group, the lower alkyl group cannot be a methyl group.

In the formula (I-b), the lower alkyl for R1, R2, R3, R4, R5, R6, R7 and R8 includes a straight or branched alkyl having 1 to 6 carbon atoms such as methyl, ethyl, n-propyl, n-butyl, iso-propyl, iso-butyl, 1-methylpropyl, tert-butyl, n-pentyl, 1-ethylpropyl, iso-amyl and n-hexyl. Methyl and ethyl are preferable. The acyl for R2 includes a residue of an organic acid such as an aliphatic saturated carboxylic acid, an aliphatic unsaturated carboxylic acid, a carbocyclic carboxylic acid and a hetero-cyclic carboxylic acid. It includes in particular a lower alkanoyl such as formyl, acetyl, propionyl, butyryl, iso-butyryl, valeryl, iso-valeryl and pivaloyl, an aroyl such as benzoyl, toluoyl and naphthoyl and a hetro-aroyl such as furoyl, nicbtinoyl and iso-nicotinoyl.

Compound Group (I-c)

The compound group (I-c) has the formula (I-c):

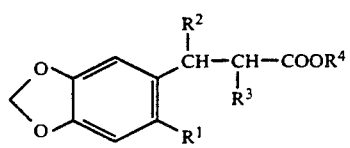

wherein $R^1$ represents a hydrogen atom or a lower alkyl or lower alkoxy-lower alkyl group, $R^2$ represents a hydrogen atom or a lower alkyl or lower alkoxy group, $R^3$ represents a hydrogen atom or a lower alkyl group and $R^4$ represents a hydrogen atom or a lower alkyl group, or $R^1$ and $R^2$ or $R^1$ and $R^3$ may form together a 5- to 7-membered ring, with the proviso that all of $R^1$, $R^2$ and $R^3$ cannot be hydrogen atoms at the same time.

In the formula (I-c), the lower alkyl for R1, R2, R3 and R4 includes an alkyl, straight or branched, having 1 to 6 carbon atoms, such as methyl, ethyl, propyl, iso-propyl, butyl, iso-butyl, sec-butyl, tert-butyl, pentyl (amyl), iso-pentyl, neopentyl, tert-pentyl, 1-methylbutyl, 2-methylbutyl, 1,2-dimethylpropyl, hexyl, iso-hexyl, 1-methylpentyl, 2-methylpentyl, 3-methylpentyl, 1,1-dimethylbutyl, 1,2-dimethylbutyl, 2,2-dimethylbutyl, 1,3-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl. Methyl, ethyl, propyl and iso-propyl are preferable. The lower alkoxy for $R^2$ includes an alkoxy, straight or branched, having 1 to 6 carbon atoms, such as methoxy, ethoxy, n-propoxy, iso-propoxy, n-butoxy, iso-butoxy, sec-butoxy, tert-butoxy, pentyloxy, iso-pentyloxy, neopentyloxy, tert-pentyloxy, 1-methylbutoxy, 2-methylbutoxy, 1,2-dimethylpropoxy and hexyloxy. Methoxy and ethoxy are preferable. The lower alkoxy-lower alkyl for R1 includes methoxymethyl, methoxyethyl, methoxypropyl, ethoxymethyl, ethoxyethyl, ethoxypropyl, propoxymethyl, propoxyethyl and propoxypropyl. Methoxymethyl and ethoxymethyl are preferable. R1 and R2 may, together in combination, form a 5- to 7-membered ring. This is exemplified in Example 13. The 5- to 7-membered ring may contain oxygen atom, in addition to a ring consisting of carbon atoms. R1 and R3 also may, together in combination, form a 5-to 7-membered ring, exemplified in Example 11.

Compound Group (I-d)

The compound group (I-d) has the formula (I-d):

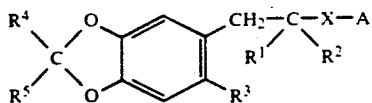 (I-d)

wherein $R^1$ and $R^2$ may be the same or different from each other and each represents a hydrogen atom or a lower alkyl group, $R^3$ represents a hydrogen atom, a lower alkyl group or a group of the formula: —$(CH_2)_n$COOH in which n represents an integer of 1 to 3, $R^4$ and $R^5$ may be the same or different from each other and each represents a hydrogen atom or a lower alkyl group, X represents a group of the formula:

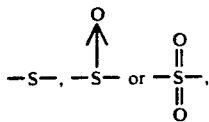

A represents a lower alkyl group, a group of the formula: —$(CH_2)_{n'}$-Het in which n' represents an integer of 1 to 3 and Het represents a substituted or unsubstituted heterocyclic ring, a group of the formula:

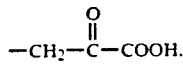

a group of the formula:

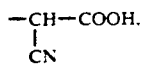

a group of the formula

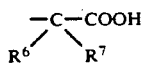

in which $R^6$ and $R^7$ may be the same or different from each other and each represents a hydrogen atom or a lower alkyl group, a group of the formula: —$CH_2$—CN, a group of the formula:

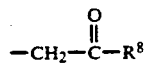

in which $R^8$ represents a lower alkyl group or a group of the formula:

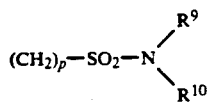

in which p represents an integer of 1 to 3 and $R^9$ and $R^{10}$ may be the same or different from each other and each represents a lower alkyl group.

In the formula (I-d), the lower alkyl for R1, R2, R3, R4, R5, R6, R7, R8, R9 and R10 includes a straight or branched alkyl having 1 to 6 carbon atoms such as methyl, ethyl, propyl, iso-propyl, butyl, iso-butyl, sec-butyl, tert-butyl, pentyl (amyl), iso-pentyl, neopentyl, tert-pentyl, 1-methylbutyl, 2-methylbutyl, 1,2-dimethylpropyl, hexyl, iso-hexyl, 1-methylpentyl, 2-methylpentyl, 3-methylpentyl, 1,1-dimethylbutyl, 1,2-dimethylbutyl, 2,2-dimethylbutyl, 1,3-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl. Methyl, ethyl, propyl and iso-propyl are preferable. The heterocyclic ring, called Het in the A, means a nitrogen-containing hetero-cyclic ring, such as pyridine, pyradine, pyrimidine, imidazole, pyrazole, oxazole, iso-oxazole, thiazole and iso-thiazole. The hetero-cyclic ring may have a substituent such as a lower alkyl, for example methyl, and hydroxyl. Pyridyl, imidazolyl and iso-oxazolyl are preferable.

Compound Group (I-e)

The compound group (I-e) has the formula (I-e):

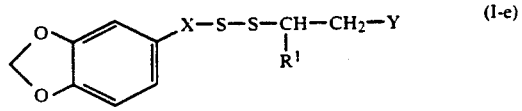 (I-e)

wherein X is a group of the formula: —$CH_2$—, —$CH_2$—$CH_2$—, —$CH_2$—$CH_2$—$CH_2$—or

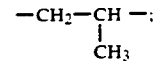

$R^1$ is a hydrogen atom or a lower alkyl group and Y is hydrogen atom or an alkyl, hydroxyl, carboxyl, aryl or heteroarylcarbonyloxy group.

In the formula (I-e), the lower alkyl for R1 includes an alkyl having 1 to 6 carbon atoms, straight or branched, such as methyl, ethyl, n-propyl, n-butyl, iso-propyl, iso-butyl, 1-methylpropyl, tert-butyl, n-pentyl, 1-ethylpropyl, iso-amyl and n-hexyl. Methyl, ethyl and n-propyl are preferable. The alkyl for Y includes an alkyl, straight or branched, such as methyl, ethyl, n-propyl, n-butyl, iso-propyl, iso-butyl, 1-methylpropyl, tert-butyl, n-pentyl, 1-ethylpropyl, iso-amyl, n-hexyl, n-heptyl, n-octyl, n-nonyl and n-decyl. The aryl for R1 includes phenyl, tolyl, xylyl, biphenyl and naphthyl. Phenyl is preferable. The hetero-arylcarboxyloxy includes one derived from a nitrogen-containing, 5- or 6-membered cyclic ring such as pyridine, pyrimidine, pyrrole, pyrazole and imidazole, thiazole, oxazole or furane. Nicotinoyloxy is preferable.

Compound Group (I-f)

The compound group (I-f) has the formula (I-f):

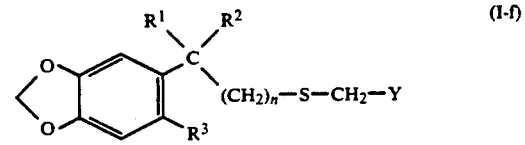 (I-f)

wherein $R^1$ and $R^2$ may be the same or different from each other and each represents a hydrogen atom or a lower alkyl, aryl or arylalkyl group; n represents an integer of 0 or 1;

Y represents a group of the formula: —COOH or

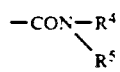

(wherein $R^4$ and $R^5$ may be the or different from each other and each represents a hydrogen atom or a lower alkyl or carboxymethyl group) and $R^3$ represents a hydrogen atom or a lower alkyl or arylalkyl group.

The lower alkyl group in the above definition with respect to the groups $R^1$, $R^2$, $R^3$, $R^4$ and $R^5$ of the compound (I) according to the present invention is a straight-chain or branched alkyl group having 1 to 6 carbon atoms and examples thereof include methyl, ethyl, n-propyl, n-butyl, isopropyl, isobutyl, 1-methylpropyl, tert-butyl, n-pentyl, 1-ethylpropyl, isoamyl and n-hexyl groups.

The aryl group in the definition with respect to the groups $R^1$ and $R^2$ includes phenyl, tolyl and naphthyl groups, among which a phenyl group is most preferred.

Preferred examples of the arylalkyl group in the definition with respect to the groups $R^1$, $R^2$ and $R^3$ include groups derived from the above aryl groups, among which benzyl and phenethyl groups are most preferred.

In the compounds according to the invention, those having the formulae (I-a), (I-b) and (I-f), respectively, are preferable.

In the invention, a preferable group of the compounds has the formula (I) in which T is hydrogen, U is hydrogen, V is $R^3$ and W is (a) or (f), in which R3, (a) and (f) are defined above, provided that the definition of (f) excludes the cases where n is zero, Y is —COOH, R1 and R2 are each hydrogen, a lower alkyl or an arylalkyl and R3 is hydrogen, a lower alkyl or an arylakyl.

It is more preferable in the formula (I-a) that X is —S—, R3 is hydrogen or a lower alkyl and R1 and R2 are each hydrogen or a lower alkyl. The compound having the formula (I-a) in which R3 is hydrogen, R1 is hydrogen, R2 is n-propyl, X is —S— and R4 is hydrogen and sodium salt thereof are most preferable.

Also the compound having the formula (I-f) in which R3 is hydrogen, R1 and R2 are hydrogen, n is one and Y is —COOH and sodium salt thereof are most preferable.

In the formula (I-b), X is preferred to be —S—. When this is the case, R is preferred to be —CH2—COOH, —(CH2)n—CH(NH2)—COOR7 or —CH —CH(NH2)COOH. In addition, it is preferred that X is —S—, R3 is hydrogen, R1 is hydrogen and R2 is —C3H8; X is —S—, R3 is hydrogen, R1 is —CH3 and R2 is —CH3; or X is —S—, R3 is —CH3 or —C2H5, R1 is hydrogen and $R^2$ is —C2H5.

All the compounds employed in the pharmacological tests, shown below, are more important to the invention. In particular, the compounds 1 to 5 shown in Table 1 in view of the the compound group I-a) and the compounds 1, 2, 4, 7, 8, 10, 11, 12, 13 and 15 listed in Table 6 in view of the compound group (I-f) are most preferred.

The pharmacologically acceptable salts may be ordinary non-toxic salts and examples thereof include salts of alkali metals such as sodium and potassium; salts of alkaline earth metals such as calcium and magnesium; salts of organic amines such as trimethylamine, triethylamine, pyridine, picoline, dicyclohexylamine and N,N'-dibenzylethylenediamine and ammonium salts and additionally, depending upon the substituent, inorganic acid salts such as hydrochloride, hydrobromide, sulfate and phosphate; organic acid salts such as acetate, maleate, tartrate, methanesulfonate, benzenesulfonate and toluenesulfonate and salts of amino acids such as arginine and aspartic and glutamic acids. Further, these salts may form hydrates.

Although the compounds of the present invention may have an asymmetric carbon atom depending upon the substituents to be present as optical isomers, it is a matter of course that these isomers are included in the scope of the present invention.

It should be understood from the results of Experimental Examples 1 and 2 that the compounds of the present invention remarkably inhibit liver trouble due to D-galactosamine or carbon tetrachloride. Thus, the compounds of the present invention are very useful as liver trouble remedies.

Accordingly, the compounds of the present invention are useful as a therapeutic and preventive medicine for various liver troubles of animals including human beings. More precisely, they can be used in the treatment and prevention of chronic or acute hepatitis, liver affections due to drugs, viral hepatitis, alcoholic hepatitis and choloplania and even cirrhosis as a terminal symptom of these diseases.

Further, it should be understood from the results of Experimental Example 3 that the compounds of the present invention exhibit remarkably low toxicity and are excellent in safety. Therefore, the compounds of the present invention are highly valuable in this regard, because they are generally administered repeatedly for a prolonged period of time owing to the nature of the trouble.

When the compounds of the present invention are administered as a therapeutic and preventive medicine for liver troubles, they may be orally administered as a powder, granule, capsule, syrup or the like or may be parenterally administered as a suppository, injection, external preparation or drop. Although the dose thereof remarkably varies depending upon the symptom, the age or the kind of the liver trouble, it is generally about 0.1 to 1,000 mg, preferably 2 to 500 mg, still preferably 5 to 100 mg, per adult and per day, which may be administered at once or in several portions a day.

The preparation of a medicine containing the compound of the present invention is carried out by using conventional carriers according to an ordinary method.

More precisely, in the production of a solid preparation for oral administration, a filler and, if necessary, a binder, disintegrating agent, lubricant, coloring agent or corrigent are added to a principal agent and the obtained mixture is converted into a tablet, coated tablet, granule, powder or capsule according to an ordinary method.

Examples of the filler include lactose, corn starch, sucrose, glucose, sorbitol, crystalline cellulose and silicon dioxide, while those of the binder include polyvinyl alcohol, polyvinyl ether, ethylcellulose, methylcellulose, gum arabic, tragacanth, gelatin, shellac, hydroxypropylcellulose, hydroxypropylmethylcellulose, calcium citrate, detrin and pectin. Examples of the lubricant include magnesium stearate, talc, polyethylene glycol, silica and hardened vegetable oils, while the coloring agent may be any one permitted as the additive to drugs. The corrigent include powdered cacao, mentha herb, aromatic powder, mentha oil, borneol and powdered cinnamon bark. Of course, these tablets and granules may be coated with sugar, gelatin or other material.

In preparing an injection containing the compound of the present invention, a principal agent is, if necessary, mixed with a pH adjusting agent, buffer, stabilizer, solubilizing agent or the like and converted into a subcutaneous, intramuscular or intravenous injection according to an ordinary method.

The above mentioned pharmacological effect of the invention compounds is supported by the pharmacological experiments procedures and results of which are described below according to the compound groups (I-a) to (I-f).

Compound Group (I-a)

Experimental Example 1a

Effect on liver injury induced by D-galactosamine in rats

Experimental method:

300 mg/kg of D-galactosamine was administered to male Fischer ($F_{344}$) rats weighing around 180 g by subcutaneous injection to induce liver injury. Each compound was dissolved in distilled water was given by oral administration in a dose of 50 mg/kg one hour after the injection of D-galactosamine.

The D-galactosamine was used in the form of a solution having a concentration of 200 mg/ml, obtained by dissolving D-galactosamine in a physiological saline solution to obtain a dilute D-galactosamine solution and adjusting the pH of the dilute solution to 7.0 with 10N aqueous potassium hydroxide.

Blood was collected from the rat's tail vein 48 h after the injection of D-galactosamine. The blood coagulation time was determined by the hepaplastin test (HPT) and GPT activity in the blood plasma was determined by an enzymatic method.

The inhibition (%) of liver injury by each compound is shown in Table 1a.

Experimental Example 2a

Effect on liver injury induced by carbon tetrachloride (CC14)

Experimental method:

0.5 ml/kg of carbon tetrachloride was given to male Fischer ($F_{344}$) rats weighing around 180 g by intraperitoneal injection to induce liver injury. In this test, carbon tetrachloride was diluted to a final concentration of 0.25 ml/ml with olive oil.

Each compound dissolved in distilled water was given by oral administration in a dose of 100 mg/kg one hour before the administration of carbon tetrachloride.

Blood was collected from the rat's tail vein 24 h after the injection of carbon tetrachloride. GPT activity in plasma as an index of the liver injury was determined by an enzymatic method. The inhibition (%) of the liver injury by each compound is shown in Table 2a.

Compound Group (I-b)

Experimental Example 1b

The method was conducted in the same way as shown in Experimental Example 1a except that 400 mg/kg of D-galactosamine was used in its solution in physiological saline and each test compound was administered in a dose of 100 mg/kg in 0.5 % methylcellulose solution. Results are shown in Table 1b.

Experimental Example 2b

The test was conducted in the same manner as shown in Experimental Example 1b except that the test compound was orally administered to the rats in a dose of 100 mg/kg in 0.5% methylcellulose solution. Results are shown in Table 2b.

Compound Group (I-c)

Experimental Examples 1c and 2c

The tests were conducted in the same ways as shown in Experimental Examples 1a and 2a, respectively. Results are shown in Tables 1c and 2c, respectively.

Compound Group (I-d)

Experimental Example 1d

The test was conducted in the same manner as shown in Experimental Example 1a except that each test compound was used in its solution in distilled water or a suspension in 0.5% methylcellulose solution. Results are shown in Table 1d.

Experimental Example 2d

The test was conducted in the same way as shown in Experimental Example 2a except that each test compound was used in a solution in distilled water. Results are shown in Table 2d.

Compound Group (I-e)

Experimental Example 1e

The test was conducted in the same way as shown in Experimental Example 1a except that 400 mg/kg of D-galactosamine was administered and each test compound was used in a dose of 100 mg/kg in a suspension of 0.5 % aqueous methylcellulose solution. Results are shown in Table 1e.

Experimental Example 2e

The test was conducted in the same way as shown in Experimental Example 2a except that each test compound was used in a suspension of 0.5 % aqueous methylcellulose solution. Results are shown in Table 2e.

Compound Group (I-f)

Experimental Example 1f

The test was conducted in the same way as shown in Experimental Example 1a except that 400 mg/kg of D-galactosamine was administered in its physiological saline solution and each test compound was used in an amount of 100 mg/kg in 0.5 % methylcellulose liquid. Results are shown in Table 1f.

Experimental Example 2f

The test was conducted in the same way as shown in Experimental Example 1a except that each test compound was used in an amount of 100 mg/kg in a suspension in 0.5% methylcellulose solution. Results are shown in Table 2f.

Toxicological Test of Compound Groups (I-a) to (I-f)

Male ddy mice being 7 weeks old and weighing around 30 g were used. 800 mg/kg of the respective compounds shown in Tables 1a, 1b, 1c, 1d and 1f and the respective compounds 1, 3, 6 and 7 of Table 1e were administered orally to the mice for 4 days. No mouse died.

TABLE 1a

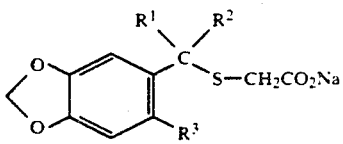

| Compound No. (Example No.) | $R^1$ | $R^2$ | $R^3$ | Inhibition ratio (%) HPT | GPT |
|---|---|---|---|---|---|
| Compound 1 (Example 2) | $-CH_2CH_2CH_3$ | H | H | 88 | 90 |
| Compound 2 (Example 4) | $-CH_3$ | $-CH_3$ | H | 96 | 78 |
| Compound 3 (Example 6) | $-CH_3$ | H | $-CH_3$ | 94 | 81 |
| Compound 4 (Example 8) | $-CH_2CH_3$ | H | $-CH_3$ | 100 | 100 |
| Compound 5 (Example 11) | $-CH_2CH_3$ | H | $-CH_2CH_3$ | 96 | 82 |
| Compound 6 (Example 13) | H | H | $-CH_3$ | 51 | 45 |
| Compound 7 (Example 15) | H | $-(CH_2)_2-$ | | 86 | 56 |

TABLE 1a-continued

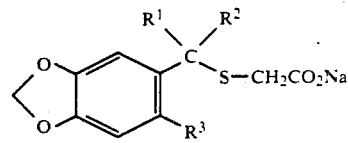

| Compound No. (Example No.) | $R^1$ | $R^2$ | $R^3$ | Inhibition ratio (%) HPT | GPT |
|---|---|---|---|---|---|
| Compound 8 (Example 17) | H | $-(CH_2)_3-$ | | 100 | 92 |

TABLE 2a

| Compound No. | Inhibition ratio (%) GPT |
|---|---|
| Compound 1 | 96 |
| Compound 2 | 88 |
| Compound 3 | 98 |
| Compound 4 | 80 |

TABLE 1b

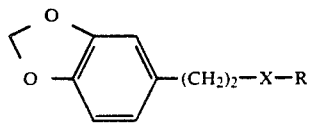

(I-b)

| Compound No. (Example No.) | X | R | Inhibition ratio (%) HPT | GPT |
|---|---|---|---|---|
| Compound 1 (Example 1) | $-S-$ | H | 96 | 91 |
| Compound 2 (Example 10) | $-S-$ | $-CH_2CH_2CH_3$ | 94 | 84 |
| Compound 3 (Example 11) | $-S-$ | $-CH_2CH_2OH$ | 94 | 97 |
| Compound 4 (Example 12) | $-S-$ | $-(CH_2)_3OH$ | 98 | 98 |
| Compound 5 (Example 13) | $-S-$ | $-CH_2-CH(OH)-CH_2OH$ | 65 | 43 |
| Compound 6 (Example 14) | $-S-$ | $-CH_2CH_2OCH_3$ | 93 | 79 |
| Compound 7 (Example 15) | $-S-$ | $-CH_2-$(tetrahydrofuran-2-yl) | 96 | 92 |
| Compound 8 (Example 3) | $-S-$ | $-CH_2COONa$ | 97 | 97 |
| Compound 9 (Example 16) | $-S-$ | $-CH_2CH_2COONa$ | 99 | 100 |
| Compound 10 (Example 17) | $-S-$ | $-(CH_2)_3COONa$ | 99 | 89 |
| Compound 11 (Example 18) | $-S-$ | $-(CH_2)_4COONa$ | 98 | 96 |
| Compound 12 (Example 19) | $-S-$ | $-(CH_2)_3COONa$ | 75* | 69* |
| Compound 13 (Example 20) | $-S-$ | $-CH(CH_3)-CH_2COONa$ | 99 | 99 |
| Compound 14 (Example 21) | $-S-$ | $-CH(COOH)-CH_2COOH$ | 50 | 35 |

TABLE 1b-continued $$\text{(I-b)}$$

(structure: methylenedioxybenzene-(CH$_2$)$_2$-X-R)

| Compound No. (Example No.) | X | R | Inhibition ratio (%) HPT | Inhibition ratio (%) GPT |
|---|---|---|---|---|
| Compound 15 (Example 22) | —S— | —CH(CH$_3$)—COOH | 90 | 73 |
| Compound 16 (Example 23) | —S— | —CH$_2$CONH$_2$ | 94 | 86 |
| Compound 17 (Example 4) | —S— | —CH$_2$CH$_2$—C(=O)—NH$_2$ | 99 | 97 |
| Compound 18 (Example 24) | —S— | —CH$_2$—C(=O)—N(C$_2$H$_5$)$_2$ | 50 | 51 |
| Compound 19 (Example 25) | —S— | —CH$_2$CH$_2$—C(=O)—N(CH$_3$)$_2$ | 90 | 69 |
| Compound 20 (Example 26) | —S— | —CH$_2$CH$_2$—N(CH$_3$)$_2$ | 71 | 43 |
| Compound 21 (Example 2) | —S— | —CH$_2$CH(NH$_2$)—COONa | 93* | 93* |
| Compound 22 (Example 8) | —S— | —(CH$_2$)$_2$—O—C(=O)—(3-pyridyl) | 69 | 67 |
| Compound 23 (Example 9) | —S— | —CH$_2$—C(=O)—N(H)(CH$_2$COOH) | 92 | 77 |
| Compound 24 (Example 27) | —S— | —(CH$_2$)$_2$—C(=O)—N(H)(CH$_2$COOH) | 90 | 86 |
| Compound 25 (Example 5) | —S— | —CH$_2$COOC$_2$H$_5$ | 61 | 34 |
| Compound 26 (Example 6) | O↑—S— | —CH$_3$ | 100 | 100 |
| Compound 27 (Example 28) | O↑—S— | —CH$_2$CH$_2$OH | 65 | 54 |
| Compound 28 (Example 7) | —S(=O)$_2$— | —CH$_3$ | 98 | 95 |

TABLE 1b-continued $$\text{(I-b)}$$

[Structure: benzodioxole ring with -(CH$_2$)$_2$-X-R substituent]

| Compound No. (Example No.) | X | R | Inhibition ratio (%) HPT | GPT |
|---|---|---|---|---|
| Compound 29 (Example 29) | -S(=O)$_2$- | -CH$_2$CH$_2$OH | 84 | 63 |
| Compound 30 (Example 30) | -S(=O)$_2$- | -CH$_2$COOH | 33 | 53 |
| Compound 31 (Example 31) | -S(=O)$_2$- | -CH$_2$CH$_2$COOH | 37 | 26 |
| Compound 32 (Example 32) | -S(=O)$_2$- | -(CH$_2$)$_3$COOH | 26 | 28 |

TABLE 2b

| Compound No. | Inhibition ratio (%) GPT |
|---|---|
| compound 3 | 47 |
| compound 4 | 93 |
| compound 8 | 53 |
| compound 9 | 98 |
| compound 10 | 43 |
| compound 11 | 90 |
| compound 13 | 86 |
| compound 16 | 61 |
| compound 17 | 98 |
| compound 21 | 34 |
| compound 25 | 21 |
| compound 26 | 97 |
| compound 28 | 97 |

TABLE 1c

[Structure: benzodioxole with -CH(R$^2$)-CH(R$^3$)-COONa and R$^1$ substituent]

| Compound No. (Example No.) | R$^1$ | R$^2$ | R$^3$ | Inhibition ratio (%) HPT | GPT |
|---|---|---|---|---|---|
| Compound 1 (Example 2) | -CH$_2$CH$_2$CH$_3$ | H | H | 78 | 77 |
| Compound 2 | -CH$_2$CH$_3$ | H | H | 75 | 78 |

TABLE 1c-continued

[Structure: benzodioxole with -CH(R$^2$)-CH(R$^3$)-COONa and R$^1$ substituent]

| Compound No. (Example No.) | R$^1$ | R$^2$ | R$^3$ | Inhibition ratio (%) HPT | GPT |
|---|---|---|---|---|---|
| Compound 3 (Example 4) | -CH$_3$ | H | H | 89 | 73 |
| Compound 4 (Example 6) | -CH$_2$OCH$_3$ | H | H | 67 | 49 |
| Compound 5 (Example 8) | -CH$_2$OCH$_2$CH$_3$ | H | H | 75 | 73 |
| Compound 6 (Example 10) | -CH$_2$- | H | | 67 | 60 |
| Compound 7 (Example 12) | -CH$_2$CH$_2$O- | H | | 51 | 12 |

TABLE 2c

| Compound No. | Inhibition ratio (%) GPT |
|---|---|
| Compound 3 | 77 |
| Compound 4 | 72 |
| Compound 6 | 94 |
| Compound 7 | 84 |

TABLE 1d

| Compound No. | Structural formula | Inhibition ratio (%) HPT | Inhibition ratio (%) GPT |
| --- | --- | --- | --- |
| Compound 1 | 3,4-methylenedioxyphenyl-CH$_2$CH$_2$SCH$_2$C(=O)CH$_3$ | 100 | 89 |
| Compound 2 | 3,4-methylenedioxyphenyl-CH$_2$CH$_2$SCH$_2$CN | 100 | 88 |
| Compound 4 | 3,4-methylenedioxyphenyl-CH$_2$CH$_2$SC(CH$_3$)(CH$_3$)CO$_2$Na | 91 | 84 |
| Compound 5 | 3,4-methylenedioxyphenyl-CH$_2$CH$_2$SCH$_2$C(=O)CO$_2$H | 24 | 23 |
| Compound 6 | 3,4-methylenedioxyphenyl-CH$_2$CH$_2$SCH$_2$-(4-pyridyl) | 76 | 64 |
| Compound 7 | 3,4-methylenedioxyphenyl-CH$_2$CH$_2$SCH$_2$-(2-pyridyl) | 58 | 37 |
| Compound 8 | 3,4-methylenedioxyphenyl-CH$_2$CH$_2$SCH$_2$-(imidazolyl) | 61 | 28 |
| Compound 10 | 3,4-methylenedioxyphenyl-CH$_2$CH$_2$SCH$_2$CH$_2$-C(=NONa)-C(CH$_3$)=N-O (isoxazole) | 25 | 35 |
| Compound 12 | 2-methyl-1,3-benzodioxol-5-yl-CH$_2$CH$_2$SCH$_2$CO$_2$Na | 85 | 85 |
| Compound 14 | 2,2-dimethyl-1,3-benzodioxol-5-yl-CH$_2$CH$_2$SCH$_2$CO$_2$Na | 85 | 90 |
| Compound 16 | 6-methyl-1,3-benzodioxol-5-yl-CH$_2$CH$_2$SCH$_2$CO$_2$Na | 41 | 25 |

TABLE 1d-continued

| Compound No. | Structural formula | Inhibition ratio (%) HPT | GPT |
|---|---|---|---|
| Compound 18 | 3,4-methylenedioxyphenyl with $CH_2CH_2SCH_2CO_2Na$ and $CH_2CH_3$ | 62 | 60 |
| Compound 20 | 3,4-methylenedioxyphenyl with $CH_2CH_2SCH_2CO_2Na$ and $CH_2CH_2CH_3$ | 93 | 87 |
| Compound 22 | 3,4-methylenedioxyphenyl with $CH_2CH_2SCH_2CH_3$ and $CH_2CH_2CO_2Na$ | 77 | 74 |
| Compound 24 | 3,4-methylenedioxyphenyl-$CH_2C(CH_3)_2SCH_2CO_2Na$ | 59 | 40 |
| Compound 26 | 3,4-methylenedioxyphenyl-$CH_2CH(CH_2CH_3)SCH_2CO_2Na$ | 48 | 53 |
| Compound 28 | 3,4-methylenedioxyphenyl-$CH_2CH_2SCH(CN)CO_2Na$ | 45 | 44 |
| Compound 29 | 3,4-methylenedioxyphenyl-$CH_2CH_2SCH_2CH_2SO_2N(CH_3)_2$ | 75 | 53 |
| Compound 30 | 3,4-methylenedioxyphenyl-$CH_2CH_2S(O)CH_2C(O)CH_3$ | 22 | 46 |
| Compound 31 | 3,4-methylenedioxyphenyl-$CH_2CH_2S(O)CH_2CH_2$ | 92 | 89 |
| Compound 32 | 3,4-methylenedioxyphenyl-$CH_2CH_2S(O)CH(CH_3)CH_2$ | 88 | 80 |
| Compound 33 | 3,4-methylenedioxyphenyl-$CH_2CH_2S(O)CH_2CN$ | 78 | 82 |

TABLE 1d-continued

| Compound No. | Structural formula | Inhibition ratio (%) HPT | GPT |
|---|---|---|---|
| Compound 34 | [3,4-methylenedioxyphenyl]-CH$_2$CH$_2$S(O)$_2$CH$_2$CCH$_2$ (with =O) | 17 | 37 |
| Compound 35 | [3,4-methylenedioxyphenyl]-CH$_2$CH$_2$S(O)$_2$CH$_2$CH$_3$ | 80 | 76 |
| Compound 36 | [3,4-methylenedioxyphenyl]-CH$_2$CH$_2$S(O)$_2$-CH(CH$_3$)$_2$ | 68 | 59 |
| Compound 37 | [3,4-methylenedioxyphenyl]-CH$_2$CH$_2$S(O)$_2$CH$_2$CN | 44 | 52 |

TABLE 2d

| Compound No. | Inhibition ratio (%) GPT |
|---|---|
| compound 1 | 90 |
| compound 2 | 99 |
| compound 16 | 73 |
| compound 18 | 82 |
| compound 26 | 55 |
| compound 28 | 75 |
| compound 33 | 99 |

TABLE 1e

| Test compound No. | Structural formula | Inhibition ratio (%) HPT | GFT |
|---|---|---|---|
| compound 1 (Ex. 1) | [3,4-methylenedioxyphenyl]-(CH$_2$)$_2$S—S(CH$_2$)$_2$OH | 82 | 92 |
| compound 2 (Ex. 2) | [3,4-methylenedioxyphenyl]-(CH$_2$)$_2$S—S(CH$_2$)$_2$-[3,4-methylenedioxyphenyl] | 57 | 54 |
| compound 3 (Ex. 3) | [3,4-methylenedioxyphenyl]-(CH$_2$)$_2$S—S(CH$_2$)$_2$OC(=O)-(3-pyridyl) | 62 | 92 |
| compound 4 (Ex. 4) | [3,4-methylenedioxyphenyl]-(CH$_2$)$_2$S—S(CH$_2$)$_2$OC(=O)-(3-pyridyl)·HCl | 59 | 89 |
| compound 5 (Ex. 5) | [3,4-methylenedioxyphenyl]-(CH$_2$)$_2$S—S(CH$_2$)$_2$OH | 51 | 59 |

TABLE 1e-continued

| Test compound No. | Structural formula | Inhibition ratio (%) HPT | GFT |
|---|---|---|---|
| compound 6 (Ex. 6) | benzodioxole-(CH$_2$)$_2$S—S(CH$_2$)$_2$-phenyl | 58 | 56 |
| compound 7 (Ex. 7) | benzodioxole-(CH$_2$)$_2$S—S(CH$_2$)$_2$OC(=O)-pyridyl | 43 | 72 |
| compound 8 (Ex. 8) | benzodioxole-(CH$_2$)$_2$S—S(CH$_2$)$_2$OC(=O)-pyridyl·HCl | 55 | 87 |
| compound 9 (Ex. 9) | benzodioxole-(CH$_2$)$_2$S—S(CH$_2$)$_3$CH$_3$ | 49 | 53 |
| compound 10 (Ex. 10) | benzodioxole-CH$_2$S—S(CH$_2$)$_2$OC(=O)-pyridyl | 43 | 72 |
| compound 11 (Ex. 11) | benzodioxole-CH$_2$CH(CH$_3$)S—SCH(CH$_3$)CH$_2$-benzodioxole | 68 | 76 |
| compound 12 (Ex. 12) | benzodioxole-CH$_2$CH(CH$_3$)S—S(CH$_2$)$_2$OH | 45 | 63 |

TABLE 2e

| Compound No. | Inhibition ratio (%) GPT |
|---|---|
| compound 1 | 97 |
| compound 3 | 97 |
| compound 4 | 94 |
| compound 5 | 91 |
| compound 6 | 66 |

TABLE 2e-continued

| Compound No. | Inhibition ratio (%) GPT |
|---|---|
| compound 7 | 91 |
| compound 8 | 82 |
| compound 9 | 42 |
| compound 10 | 75 |

TABLE 1f

| Test compound No. | Structural formula | Inhibition ratio (%) HPT | GPT |
|---|---|---|---|
| 1 | benzodioxole-CH(CH$_2$-CH(CH$_3$)-)CHSCH$_2$CO$_2$Na | 100 | 84 |

TABLE 1f-continued

| Test compound No | Structural formula | Inhibition ratio (%) HPT | Inhibition ratio (%) GPT |
|---|---|---|---|
| 2 | benzo[1,3]dioxole with -CH(CH$_2$CH$_2$CH$_2$CH$_3$)SCH$_2$CO$_2$Na | 83 | 76 |
| 3 | benzo[1,3]dioxole with -C(CH$_3$)(CH$_2$CH$_3$)SCH$_2$CO$_2$Na | 100 | 100 |
| 4 | benzo[1,3]dioxole with -CH(CH$_2$C$_6$H$_5$)SCH$_2$CO$_2$Na | 100 | 89 |
| 5 | benzo[1,3]dioxole with -CH(CH$_2$CH$_2$CH$_3$)SCH$_2$CO$_2$Na and CH$_3$ | 67 | 97 |
| 6 | benzo[1,3]dioxole with -CH$_2$SCH$_2$CO$_2$Na and -CH(CH$_3$)$_2$ | 100 | 100 |
| 7 | benzo[1,3]dioxole with -CH(CH$_3$)$_2$ and -CH(C$_6$H$_5$)SCH$_2$CO$_2$Na | 67 | 83 |
| 8 | benzo[1,3]dioxole with -CH$_2$SCH$_2$CO$_2$Na and -CH$_2$C$_6$H$_5$ | 96 | 100 |
| 9 | benzo[1,3]dioxole with -CH(CH$_3$)$_2$ and -CH$_2$CH$_2$SCH$_2$CO$_2$Na | 67 | 88 |
| 10 | benzo[1,3]dioxole with -CH$_2$CH$_2$SCH$_2$CO$_2$Na and -CH$_2$C$_6$H$_5$ | 96 | 100 |

TABLE 1f-continued
| Test compound No. | Structural formula | Inhibition ratio (%) HPT | GPT |
|---|---|---|---|
| 11 | 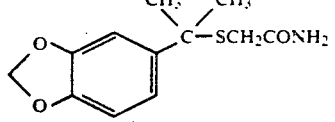 | 68 | 97 |
| 12 | 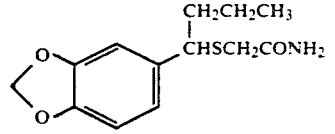 | 76 | 75 |
| 13 | 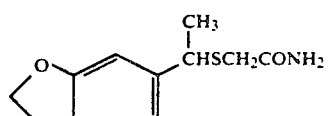 | 17 | 50 |
| 14 | 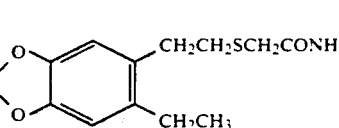 | 32 | 33 |
| 15 | 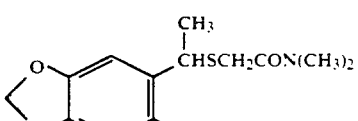 | 50 | 42 |
| 16 | 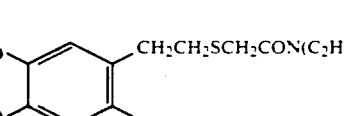 | 76 | 96 |
| 17 | 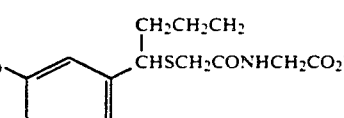 | 70 | 91 |
TABLE 2f
| Test compound No. | Structural formula | Inhibition ratio (%) HPT | GPT |
|---|---|---|---|
| 1 | 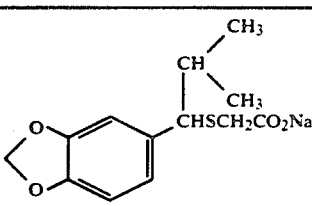 | 100 | 94 |
| 2 | 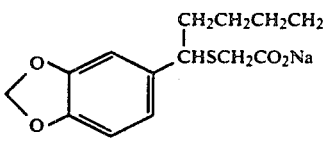 | 100 | 95 |

TABLE 2f-continued

| Test compound No. | Structural formula | Inhibition ratio (%) | |
|---|---|---|---|
| | | HPT | GPT |
| 4 | (structure) | 100 | 94 |
| 8 | (structure) | 75 | 89 |
| 9 | (structure) | 100 | 97 |
| 12 | (structure) | 100 | 92 |
| 17 | (structure) | 75 | 89 |

A symbolic reference to * in Table 1b shows administration of 50 mg/kg.

The compounds of the invention can be prepared by various processes. Typical examples of the processes are described below according to the respective compound groups.

Compound Group (I-a)

Preparation process A

Preparation of compounds of the general formula (I) wherein X represents a group of the formula: —S—

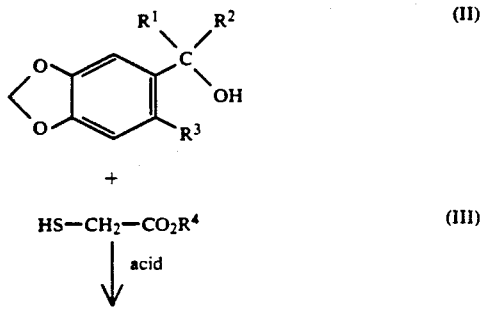

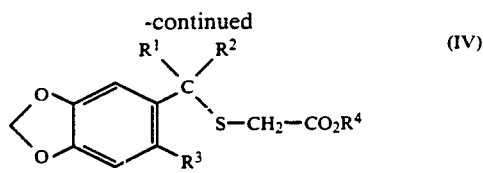

wherein $R^1$, $R^2$ and $R^3$ are as defined above and $R^4$ represents H or a lower alkyl group.

In this process, an alcohol of the general formula (II) is reacted with a thiol of the general formula (III) to obtain an intended compound (IV). This reaction is conducted by an ordinary method without using any solvent or in an organic solvent inert to the reaction selected from the group consisting of aromatic hydrocarbons such as benzene, toluene and xylene, ethers such as ethyl ether, isopropyl ether, tetrahydro-furan and dioxane, halogenated hydrocarbons such as di-chloro-methane, chloroform and carbon tetrachloride, esters such as ethyl acetate, ketones, such as acetone and methyl ethyl ketone, as well as acetonitrile, dimethylformamide and acetic acid under cooling with ice, at room temperature or under heating for several hours. The reaction proceeds easily when an acid such as sulfuric, p-toluenesulfonic or D-10-camphorsulfonic acid is used as the catalyst.

Preparation process B

Preparation of compounds of the general formula (I) wherein X represents a group of the formula: —S—

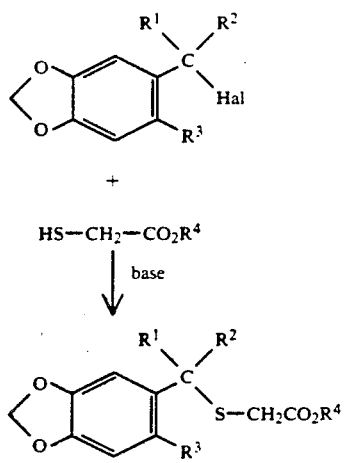

wherein Hal represents a halogen atom and $R^1$, $R^2$, $R^3$ and $R^4$ are as defined above In this process, a halogen compound of the general formula (V) is reacted with a thiol of the general formula (III) to obtain an intended compound (IV).

This reaction is conducted by an ordinary method without using any solvent or in an organic solvent inert to the reaction selected from the group consisting of aromatic hydrocarbons such as benzene, toluene and xylene, ethers such as tetrahydro-furan and dioxane, ketones such as acetone and methyl ethyl ketone, alcohols such as methanol and ethanol, halogenated hydrocarbons such as chloroform and carbon tetrachloride, as well as acetonitrile, dimethylformamide and dimethyl sulfoxide under cooling with ice, at room temperature or under heating for several hours. The reaction proceeds easily when an alkali metal carbonate or hydrogencarbonate such as sodium hydrogen-carbonate, potassium carbonate or sodium carbonate, an alkali hydroxide such as sodium hydroxide or potassium hydroxide, an organic base such as triethylamine, pyridine or diethylaniline, or sodium hydride is used as a dehydrohalogenating agent.

Preparation process C

Preparation of compounds of the general formula (I) wherein X represents a group of the formula: —S—

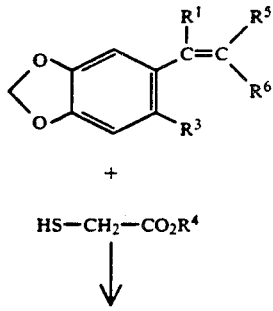

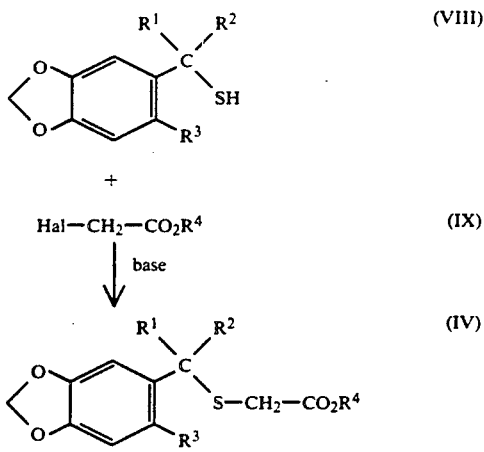

wherein $R^1$ and $R^3$ are as defined above, $R^4$ represents a hydrogen atom or a lower alkyl group, and $R^5$ and $R^6$ each represents a hydrogen atom or an alkyl, aryl, arylalkyl, heteroalkyl or heteroarylalkyl group.

In this process, a compound of the general formula (VI) is reacted with a thiol of the general formula (III) to obtain an intended compound (VII). This reaction is conducted by an ordinary method without using any solvent or in an organic solvent selected from the group consisting of aromatic hydrocarbons such as benzene, toluene and xylene, ethers such as tetrahydrofuran and dioxane, halogenated hydrocarbons such as dichloromethane, chloroform and carbon tetrachloride, ketones such as acetone and methyl ethyl ketone, esters such as ethyl acetate, as well as acetonitrile and dimethylformamide under cooling with ice, at room temperature or by heating under reflux. When the reaction proceeds only slowly, an acid such as sulfuric, p-toluenesulfonic or D-10-camphorsulfonic acid can be used as the catalyst.

The compound (VII) thus obtained is an intended one of the present invention represented by the above general formula (I) wherein X represents —S— and $R^2$ represents

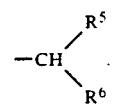

Preparation process D

Preparation of compounds of the general formula (I) wherein X represents of a group of the formula: —S—

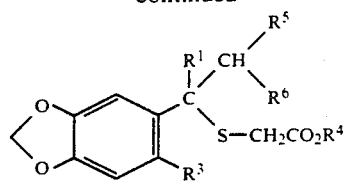

wherein Hal represents a halogen atom and $R^1$, $R^2$, $R^3$ and $R^4$ are as defined above.

In this process, a thiol of the general formula (VIII) is reacted with a halogen compound of the general formula (IX) under the same conditions as those of the preparation process B to obtain an intended compound (IV). Preferred results are obtained when the base shown with reference to the preparation process (B) is used.

The halogen atoms used in the preparation processes B and D include bromine, chlorine and iodine. Usually bromine or chlorine is used.

Preparation process E

Preparation of compounds of the general formula (I) wherein X represents a group of the formula: —S— and $R^4$ represents a hydrogen atom

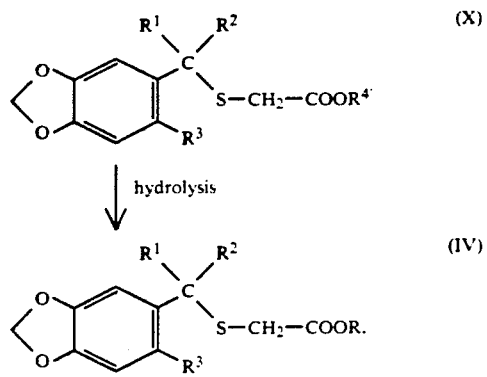

wherein $R^1$, $R^2$ and $R^3$ are as defined above and $R^{4'}$ is the same as $R^4$ but excluding the hydrogen atom, namely, $R^{4'}$ represents a lower alkyl group.

An ester of the general formula (X) which is one of the intended compounds can be hydrolyzed by an ordinary method to obtain an intended carboxylic acid of the general formula (IV)'. In particular, the hydrolysis is conducted by an ordinary method in the presence of a base or acid in a solvent suitably selected from the group consisting of water, methanol, ethanol, hydrous methanol, hydrous ethanol, hydrous tetrahydrofuran, hydrous acetonitrile and hydrous acetone. The bases include alkali metal carbonates such as sodium and potassium carbonates and alkali hydroxides such as sodium and potassium hydroxides. The acids include, for example, hydrochloric and sulfuric acids.

Preparation process F

Preparation of compounds of the general formula (I) wherein X represents a group of the formula:

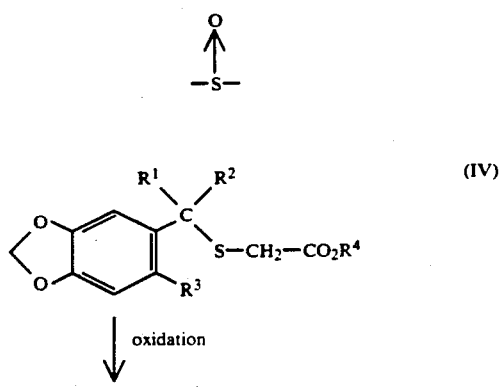

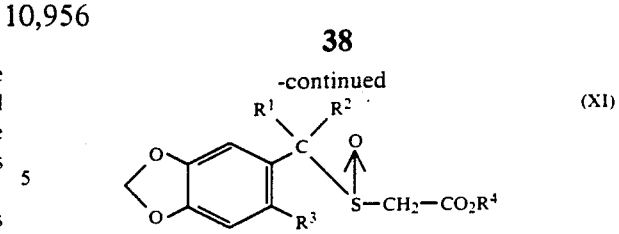

wherein $R^1$, $R^2$, $R^3$ and $R^4$ are as defined above.

In this process, an intended compound (XI) is prepared by oxidizing, for example, an intended compound (IV) prepared by the above-described process. In particular, the compound (IV) is dissolved in a solvent selected from the group consisting of aromatic hydrocarbons such as benzene, toluene and xylene, halogenated hydrocarbons such as dichloromethane, chloroform and carbon tetrachloride, water, alcohols such as methanol and ethanol, ethyl acetate, acetone and acetic acid, and an equimolar amount of an oxidizing agent such as hydrogen peroxide, peracetic acid, m-chloroperbenzoic acid or sodium hypochlorite is added thereto under cooling with dry ice/alcohol or ice/water to conduct the reaction in an ordinary manner and to produce an intended sulfoxide compound (XI).

Preparation process G

Preparation of compounds of the general formula (I) wherein X represents a group of the formula:

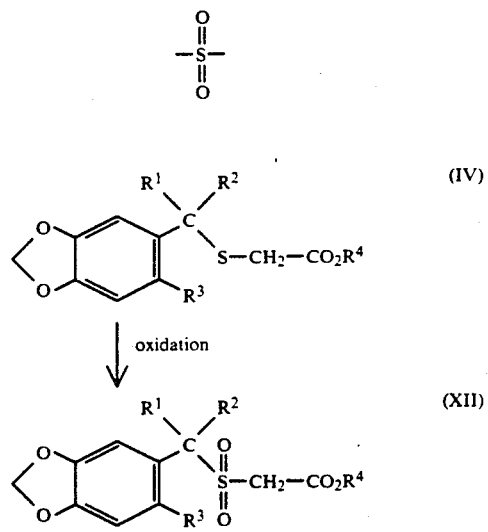

wherein $R^1$, $R^2$, $R^3$ and $R^4$ are as defined above.

In this process, an intended compound (XII) is prepared by oxidizing, an intended compound (IV) prepared by, for example, the above-described process. More particularly, the compound (IV) is dissolved in a solvent selected from the group consisting of aromatic hydrocarbons such as benzene, toluene and xylene, halggenated hydrocarbons such as dichloromethane, chloroform and carbon tetrachloride, water, alcohols such as methanol and ethanol, ethyl acetate, acetone and acetic acid, and at least two equivalents of an oxidizing agent such as hydrogen peroxide, peracetic acid, m-chloroperbenzoic acid, sodium hypochlorite or sodium m-periodate is added thereto under cooling with ice or at room temperature to conduct the reaction and thereby to obtain an intended sulfone compound (XII).

In another preparation process, a sulfoxide compound (XI) prepared by, for example, the preparation process F is dissolved in a solvent such as chloroform and then an oxidizing agent such as m-chloroperbenzoic acid is added thereto to conduct the reaction.

Pharmacologically acceptable salts of the intended compounds (I) which are also intended in the present invention can be produced by, for example, reacting a carboxylic acid compound of the general formula (I) wherein $R^4$ represents a hydrogen atom with an alkali hydrogencarbonate such as $NaHCO_3$ or $KHCO_3$, an alkali carbonate such as $Na_2CO_3$ or $K_2CO_3$ or an alkali hydroxide such as NaOH or KOH to obtain a pharmacologically acceptable salt such as sodium or potassium salt thereof.

Compound Group (I-b)

Preparation process A

Preparation of compounds of the general formula (I) wherein X represents a group of the formula: —S—

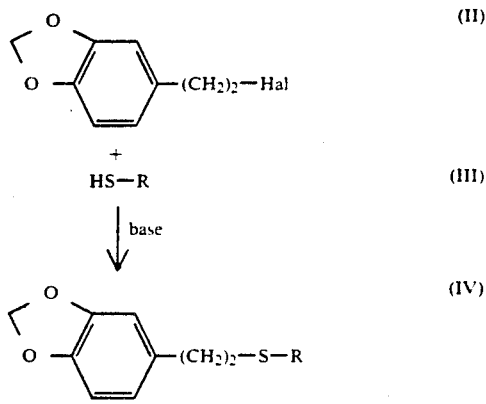

wherein Hal represents a halogen atom and R is as defined above.

In this process, 5-(2-halogenoethyl)-1,3-benzodioxole of the general formula (II) is reacted with a thiol of the general formula (III) to obtain an intended compound (IV).

This reaction is conducted by an ordinary method without using any solvent or in an organic solvent inert to the reaction selected from the group consisting of benzene, ethanol, xylene, tetrahydrofuran, chloroform, carbon tetrachloride, N,N-dimethylformamide, etc. under cooling with ice, at room temperature or under heating for several hours. The reaction is facilitated by using an inorganic base such as sodium hydrogencarbonate, potassium carbonate, sodium carbonate or sodium hydroxide or an organic base such as triethylamine, pyridine, pyrimidine or N,N-diethylaniline as the dehydrohalogenating agent.

Preparation process B

Preparation of compounds of the general formula (I) wherein X represents a group of the formula: —S—

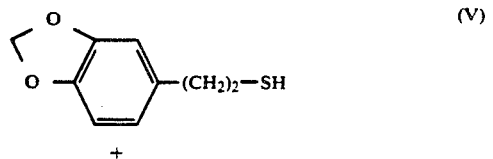

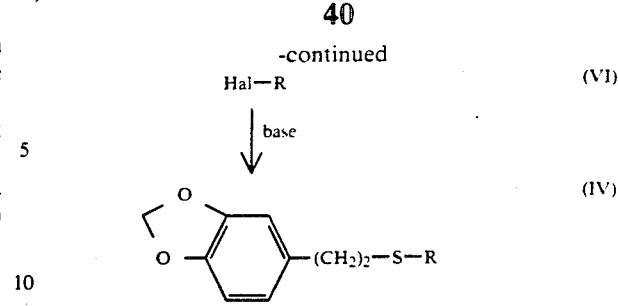

wherein Hal represents a halogen atom and R is as defined above.

In this process, 2-(1,3-benzodioxol-5-yl)ethanethiol (V) is reacted with a halogenating agent of the general formula (VI) under the same conditions as those of the preparation process A to obtain an intended compound (IV). Also in this process, preferred results are obtained when the base as described above with reference to the preparation process A is used. The halogen atoms used in the preparation processes A and B include bromine, chlorine and iodine. Usually bromine or chlorine is used.

Preparation process C

Preparation of compounds of the general formula (I) wherein X represents a group of the formula: —S—

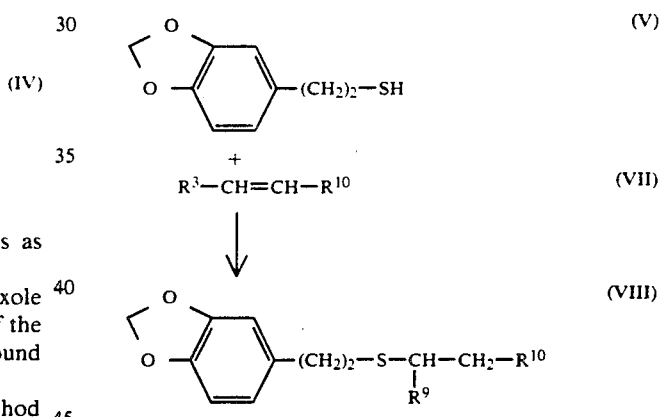

wherein $R^9$ represents a lower alkyl group and $R^{10}$ represents a lower alkyloxycarbonyl, N,N'-bis(lower alkyl)aminocarbonyl or carbamoyl group.

In this process, a thiol (V) is reacted with an unsaturated compound of the general formula (VII) by an ordinary method without using any solvent or in a solvent selected from the group consisting of, for example, benzene, dichloromethane, tetrahydrofuran, N,N-dimethylformamide and ethanol under cooling with ice, at room temperature or by heating under reflux to obtain an intended compound (VIII). When the reaction proceeds only slowly, a catalyst such as piperidine, triethylamine, sodium methylate, Triton B, sulfur or sulfuric acid can be used as the catalyst.

The compound (VIII) thus obtained is an intended one of the present invention represented by the above general formula (I) wherein X represents —S— and R represents

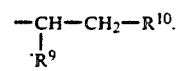

Preparation process D

Preparation of compounds of the general formula (I) wherein X represents a group of the formula: —S—

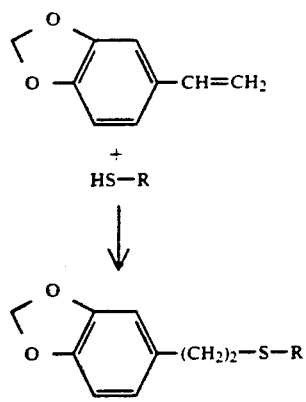

wherein R is as defined above.

In this process, 5-ethenyl-1,3-benzodioxole (IX) is reacted with a thiol of the general formula (III) by an ordinary method without using any solvent or in a solvent such as tetrahydrofuran under cooling with ice, at room temperature or by heating under reflux to obtain an intended compound (IV). When the reaction proceeds only slowly, a peroxide such as benzoyl peroxide, or azobisisobutyronitrile can be used as the catalyst.

Preparation process E

Preparation of compounds of the general formula (I) wherein X represents a group of the formula:

$$\overset{O}{\underset{}{\overset{\uparrow}{-S-}}}$$

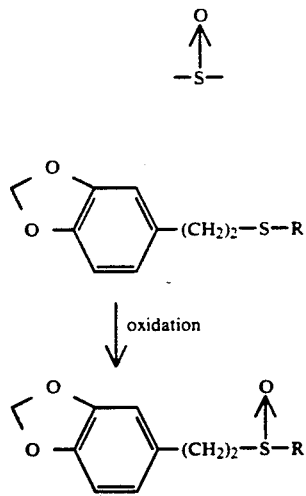

wherein R is as defined above.

In this process, an intended compound (X) is prepared by oxidizing, for example, an intended compound (IV) prepared by the above-described process. Particularly, the compound (IV) is dissolved in a solvent selected from the group consisting of aromatic hydrocarbons such as benzene, toluene and xylene, halogenated hydrocarbons such as dichloromethane, chloroform and carbon tetrachloride, water, alcohols such as methanol and ethanol, ethyl acetate, acetone and acetic acid, and an equimolar amount of an oxidizing agent such as hydrogen peroxide, peracetic acid, m-chloroperbenzoic acid or sodium hypochlorite is added thereto under cooling with dry ice/alcohol or ice/water to conduct the reaction in an ordinary manner and thereby to produce an intended sulfoxide compound (X).

Preparation process F

Preparation of compounds of the general formula (I) wherein X represents a group of the formula:

$$\overset{O}{\underset{\overset{\|}{O}}{\overset{\|}{-S-}}}$$

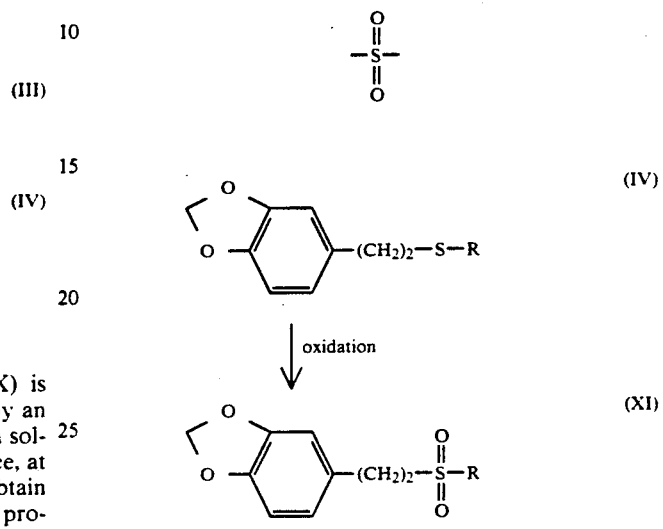

wherein R is as defined above.

In this process, an intended compound (XI) is prepared by oxidizing an intended compound (IV) prepared by the above-described process. More particularly, the compound (IV) is dissolved in a solvent selected from the group consisting of aromatic hydrocarbons such as benzene, toluene and xylene, halogenated hydrocarbons such as dichloromethane, chloroform and carbon tetrachloride, water, alcohols such as methanol and ethanol, ethyl acetate, acetone and acetic acid, and two equivalents of an oxidizing agent such as hydrogen peroxide, peracetic acid, m-chloroperbenzoic acid, sodium hypochlorite or sodium m-periodate is added thereto under cooling with ice or at room temperature to conduct the reaction and thereby to obtain an intended sulfone compound (XI).

In another preparation process, for example, a sulfoxide compound (X) prepared by the preparation process E is dissolved in a solvent such as chloroform and an oxidizing agent such as m-chloroperbenzoic acid is added thereto to conduct the reaction.

Preparation process G

Preparation of compounds of the general formula (I) wherein X represents a group of the formula: —S—

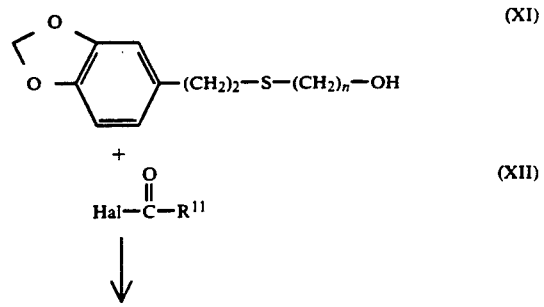

-continued

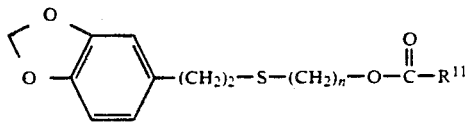
(XIII)

wherein n represents an integer of 1 to 5 and $R^{11}$ represents a lower alkyl, aryl, or heteroaryl group.

In this process, [2-(1,3-benzodioxol-5-yl)ethyl]thio derivative of the general formula (XI) as it is or in the form of a solution in, for example, benzene, dichloromethane, chloroform, tetrahydrofuran or N,N-dimethylformamide is mixed with a base such as pyridine, triethylamine, N,N-dimethylaniline or sodium carbonate as the dehydrohalogenating agent. An acid halide of the general formula: (XII) is added to the mixture to conduct the reaction and thereby to obtain an intended compound (XIII). Pyridine can be used as both the solvent and the dehydrohalogenating agent. The reaction is conducted by cooling with water or by heating under reflux.

Preparation process H

Preparation of compounds of the general formula (I) wherein X represents a group of the formula: —S—

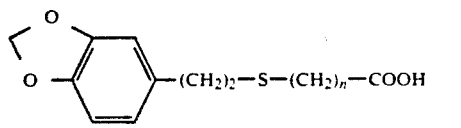
(XIV)

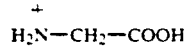

$H_2N-CH_2-COOH$ (XV)

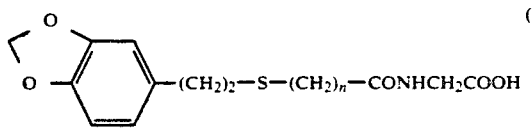
(XVI)

wherein n represents an integer of 1 to 5.

A [2-(1,3-benzodioxol-5-yl)ethyl]thio derivative (XIV) produced by, for example, the above-described process A, B or D is dissolved in a solvent such as benzene, chloroform or dimethylformamide. A chlorinating agent such as thionyl chloride, oxalyl chloride, phosphorus oxychloride or phosphorus pentachloride is added to the solution to conduct the reaction under cooling with ice, at room temperature or by heating under reflux to obtain an acid chloride derived from the compound (XIV). A solution of glycine (XV) in, for example, an aqueous sodium hydrogencarbonate solution, aqueous sodium carbonate solution or aqueous sodium hydroxide solution under stirring under cooling with ice/water to conduct the reaction and thereby to obtain an intended glycinamide (XVI).

The compound (XVI) prepared by this process is an intended compound of the general formula (I) wherein X represents —S— and $R^2$ represents —$(CH_2)_n$—$CONHCH_2COOH$.

Preparation process I

Preparation of compounds of the general formula (I) wherein X represents a group of the formula: —S—

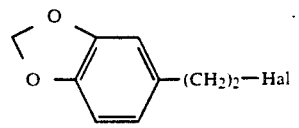
(II)

+

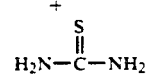
(XVII)

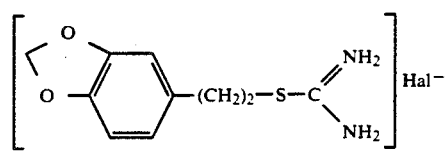
(XVIII)

↓ alkali hydrolysis

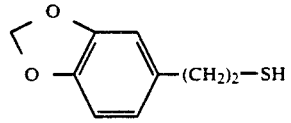
(V)

wherein Hal represents a halogen atom.

A 5-(2-halogenoethyl)-1,3-benzodioxole of the general formula (II) and thiourea of the formula (XVII) are dissolved in a solvent such as methanol or ethanol to conduct the reaction at room temperature or by heating under reflux to obtain a thiuronium salt (XVIII), which is then hydrolyzed in the presence of a base such as sodium hydroxide or potassium hydroxide in a suitably selected solvent such as water, methanol, ethanol, hydrous methanol or hydrous ethanol at room temperature or by heating under reflux to obtain intended 2-(1,3-bnezodioxol-5-yl)ethanethiol (V). The halogen atoms include bromine, chlorine and iodine. Usually bromine or chlorine is used.

Preparation process J

Preparation of compounds of the general formula (I) wherein X represents a group of the formula: —S—

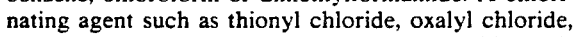
(XIV)

+

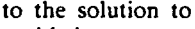
(XIX)

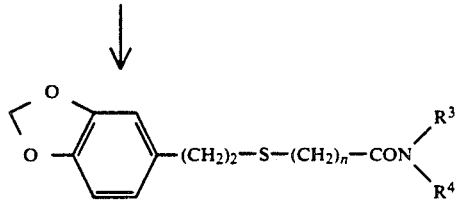
(XX)

wherein n represents an integer of 1 to 5 and $R^3$ and $R^4$ may be the same or different from each other and each represent a hydrogen atom or a lower alkyl group, The carboxylic acid prepared by the preparation process A, B or D or its reactive derivative is reacted with an amino compound of the general formula (XIX) to form an amide which is an intended compound of the formula (XX).

The reactive derivatives of the compound (XIV) include acid halides such as acid chlorides and acid bromides; acid azides; active esters thereof with N-hydroxybenzotriazole and N-hydroxysuccinimides; symmetric acid anhydrides; and mixed acid ahydrides with alkylcarbonic acids and p-toluenesulfonic acid.

When a free carboxylic acid is used as the compound (XIV), the reaction is conducted preferably in the presence of a condensation agent such as dicyclohexylcarbodiimide or 1,1'-carbonyldiimidazole.

The reaction is conducted by using a compound (XIV) or its reactive derivative and a compound (XIX) in equimolar amounts or, alternatively, by using one of them in a small excess amount, in an organic solvent inert to the reaction such as pyridine, tetrahydrofuran, dioxane, ether, benzene, toluene, xylene, methylene chloride, dichloroethane, chloroform, dimethylformamide, ethyl acetate or acetonitrile.

Depending on the kind of the reactive derivative, it is advantageous for conducting the reaction smoothly to add a base such as triethylamine, pyridine, picoline, lutidine, N,N-dimethylaniline, potassium carbonate or sodium hydroxide.

The reaction temperature is not particularly limited, since it varies depending on the kind of the reactive derivative.

Pharmacologically acceptable salts of the intended compounds (I) which are also intended products of the present invention can be prepared by, for example, reacting a carboxylic acid compound of the general formula (I) wherein R represents $-(CH_2)_n-COOH$, an amino acid compound of the general formula (I) wherein R represents

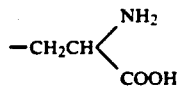

or a glycinamide compound (XVI) wherein R represents $-(CH_2)_n-CONHCH_2COOH$ with an alkali hydrogencarbonate such as sodium hydrogen-carbonate or potassium hydrogencarbonate, an alkali carbonate such as sodium carbonate or potassium carbonate or an alkali hydroxide such as sodium hydroxide or potassium hydroxide to obtain a pharmacologically acceptable salt such as the above-mentioned sodium or potassium salt.

Compound Group (I-c)

Preparation process A preparation of compounds of the general formula (I) wherein $R^4$ represents a hydrogen atom

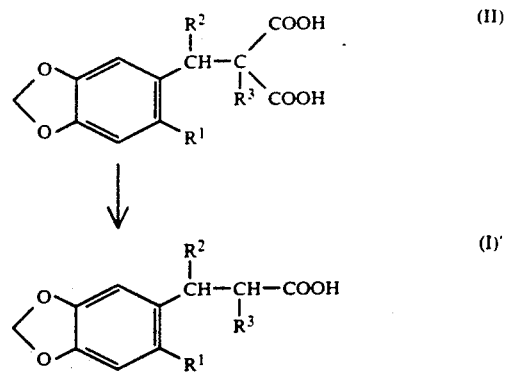

wherein $R^1$, $R^2$ and $R^3$ are as defined above.

In this process, a dicarboxylic acid of the general formula (II) is heated to a temperature of 150° C. or higher in the absence of any solvent to obtain an intended carboxylic acid (I)'.

Preparation process B

Preparation of compounds of the general formula (I) wherein $R^4$ represents a hydrogen atom

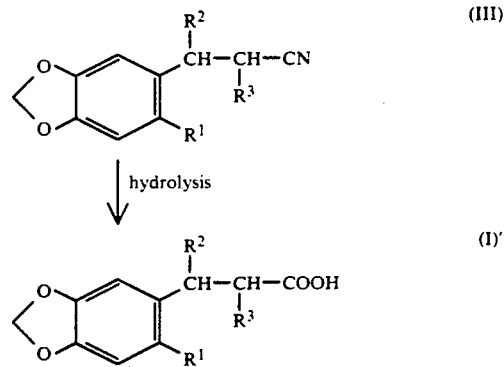

wherein $R^1$, $R^2$ and $R^3$ are as defined above.

In this process, a nitrile of the general formula (III) is hydrolyzed in an ordinary manner to obtain an intended carboxylic acid (I)'.

Particularly, the hydrolysis is conducted by an ordinary method in the presence of a base in a solvent suitably selected from the group consisting of water, alcohols such as methanol, ethanol and ethylene glycol, hydrous alcohols such as hydrous methanol, hydrous ethanol, hydrous ethylene glycol, hydrous diethylene glycol and hydrous ethylene glycol, monoethyl ether, etc. The bases used herein include, for example, potassium hydroxide, sodium hydroxide, and barium hydroxide.

Preparation process C

When $R^1$ in the general formula (I) is a lower alkoxy-lower alkyl group, the intended compound can be prepared also by the following process:

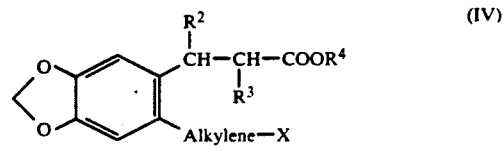

-continued

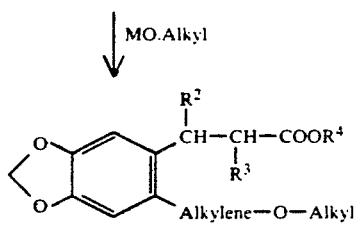
(V)

(VI)

wherein $R^2$, $R^3$ and $R^4$ are as defined above, X represents a halogen atom, M represents an alkali metal atom, "Alkyl" represents a lower alkyl group which is a straight-chain or branched one having 1 to 6 carbon atoms as described above, and "Alkylene" represents an alkylene group derived from the above-mentioned alkyl group.

In this process, a halide of the general formula (IV) is reacted with an alcoholate of the general formula (V) by an ordinary method in an organic solvent selected from the group consisting of, for example, tetrahydrofuran, dimethylformamide, methanol, ethanol and 1-propanol under cooling with ice, at room temperature or under heating to obtain an intended compound (VI). The halogen atoms usable in this process include, for example, bromine, chlorine and iodine atoms. The alkali metal atoms include, for example, sodium and potassium.

The compound (VI) obtained by this process is an intended compound of the present invention which is represented by the general formula (I) wherein $R^1$ represents —Alkylene-O-Alkyl.

Preparation process D

An intended compound of the general formula (I) wherein $R^1$ represents a lower alkoxy-lower alkyl group of the formula: —$CH_2$—O—Alkyl in which "Alkyl" represents a lower alkyl group having 1 to 6 carbon atoms can be produced also by the following process:

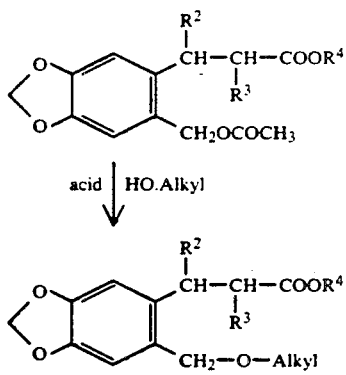
(VII)

(VIII)

(IX)

wherein $R^2$, $R^3$, $R^4$ and "Alkyl" are as defined above.

In this process, an acetoxymethyl compound of the general formula (VII) is reacted with a compound of the general formula (VIII) in the presence of an acid catalyst at room temperature or under heating to obtain an intended compound of the general formula (IX). This reaction is preferably conducted in the presence of a lower alcohol such as methanol, ethanol, 1-propanol or 2-propanol.

The acid catalysts include, for example, hydrochloric, sulfuric, p-toluenesulfonic and D-10-camphorsulfonic acids.

The compound (IX) prepared by this process is an intended compound of the present invention which is represented by the general formula (I) wherein $R^1$ represents —$CH_2$—O—Alkyl.

Preparation process E

A compound of the general formula (I) wherein $R^1$ and $R^3$ form together a ring can be prepared also by the following process:

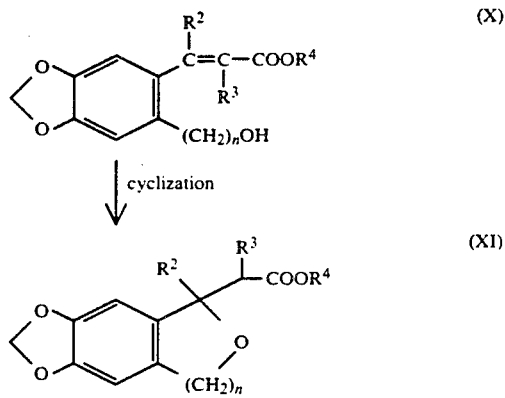
(X)

(XI)

wherein $R^2$, $R^3$ and $R^4$ are as defined above and n represents an integer of 1 to 3.

An acrylic acid derivative of the general formula (X) is subjected to an intramolecular cyclization to obtain an intended compound (XI) of the present invention. This reaction is conducted by an ordinary method without using any solvent or in an organic solvent such as benzene, ethanol, tetrahydrofuran or dimethylformamide under cooling with ice, at room temperature or under heating for several hours. The reaction proceeds easily in the presence of a base such as sodium ethylate, potassium t-butoxide or sodium hydride.

The compound (XI) obtained by the above-mentioned process is one of the intended compounds of the present invention.

Compound Group (I-d)

Preparation process A

Preparation of compounds of the general formula (I) wherein X represents a group of the formula: —S—

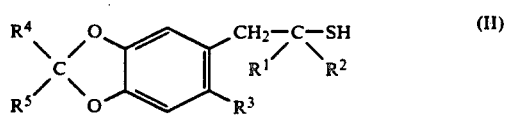
(II)

$$A-Y$$
(III)

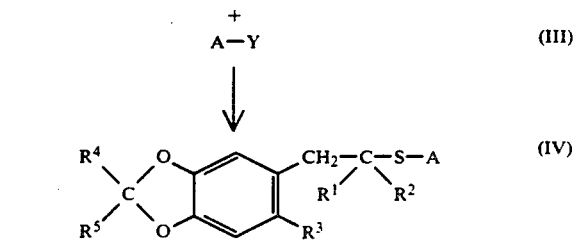
(IV)

wherein Y represents a halogen atom or a methanesulfonyloxy or p-toluenesulfonyloxy group and A, $R^1$, $R^2$, $R^3$, $R^4$ and $R^5$ are as defined above.

In this process, a thiol of the general formula (II) is reacted with a compound of the general formula (III) to form an intended compound (IV). This reaction is conducted by an ordinary method without using any solvent or in an organic solvent inert to the reaction selected from the group consisting of aromatic hydrocarbons such as benzene, toluene and xylene, ethers such as tetrahydrofuran and dioxane, ketones such as acetone and methyl ethyl ketone, alcohols such as methanol and ethanol, halogenated hydrocarbons such as chloroform and carbon tetrachloride, acetonitrile, N,N-dimethylformamide and dimethyl sulfoxide under cooling with ice, at room temperature or under heating for several hours. The reaction proceeds easily when an alkali metal carbonate or hydrogencarbonate such as sodium hydrogencarbonate, potassium carbonate or sodium carbonate, an alkali hydroxide such as sodium hydroxide or potassium hydroxide, or an organic base such as triethylamine, pyridine or diethylaniline is used as the dehydrohalogenating agent, or an agent for removing methanesulfonic or p-toluenesulfonic acid.

Preparation process B

Preparation of compounds of the general formula (I) wherein X represents a group of the formula: —S—

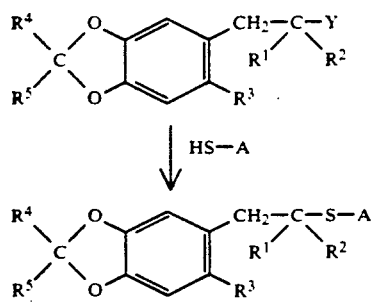

wherein Y represents a halogen atom or a methane-sulfonyloxy or p-toluenesulfonyloxy group and A, $R^1$, $R^2$, $R^3$, $R^4$ and $R^5$ are as defined above.

In this process, a compound of the general formula (V) is reacted with a thiol of the general formula (VI) under the same conditions as those of preparation process A to obtain an intended compound (IV). Also in this process, preferred results are obtained when a base described above with reference to the preparation process A is used.

The halogen atom used in the preparation processes A and B include chlorine, bromine and iodine. Usually bromine or chlorine is used.

Preparation process C

Preparation of compounds of the general formula (I) wherein X represents a group of the formula: —S—

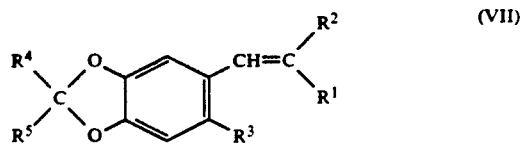

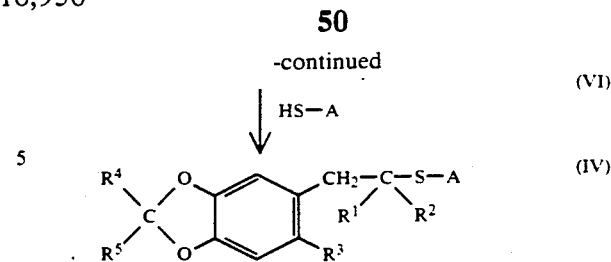

wherein A, $R^1$, $R^2$, $R^3$, $R^4$ and $R^5$ are as defined above.

A compound of the general formula (VII) is reacted with a thiol of the general formula (VI) to obtain an intended compound (IV). This reaction is conducted by an ordinary method without using any solvent or in a solvent selected from the group consisting of aromatic hydrocarbons such as benzene, toluene and xylene, ethers such as tetrahydrofuran and dioxane, halogenated hydrocarbons such as dichloromethane, chloroform and carbon tetrachloride, ketones such as acetone and methyl ethyl ketone, esters such as ethyl acetate, acetonitrile and N,N-dimethylformamide under cooling with ice, at room temperature or by heating under reflux.

When the reaction proceeds only slowly, a peroxide such as benzoyl peroxide or a catalyst such as azobisisobutyronitrile can be added.

Preparation process D

Preparation of compounds of the general formula (I) wherein X represents a group of the formula: —S—

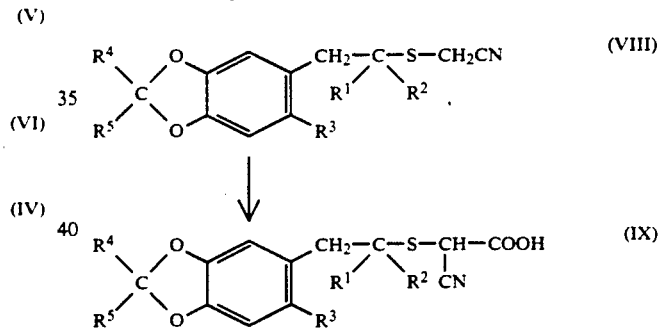

wherein $R^1$, $R^2$, $R^3$, $R^4$ and $R^5$ are as defined above.

A cyano compound of the general formula (VIII) which is also an intended compound is reacted with carbon dioxide in the presence of a base to obtain an intended carboxylic acid of the general formula (IX). In this process, a compound (VIII) as it is or in the form of a solution in an anhydrous ether solvent such as anhydrous ethyl ether, anhydrous tetrahydrofuran or anhydrous ethylene glycol dimethyl ether is reacted with a strong base such as n-butyllithium, phenyllithium, lithium diisopropylamide or sodium amide under cooling with dry ice/alcohol or with ice, and the reaction product is further reacted with carbon dioxide under cooling with dry ice/alcohol or with ice to obtain the compound (IX).

The compound (IX) is an intended one of the present invention represented by the general formula (I) wherein X represents —S—and A represents

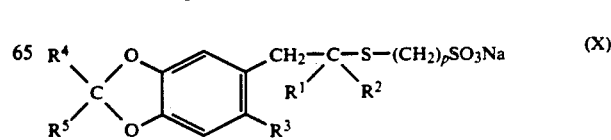

-continued

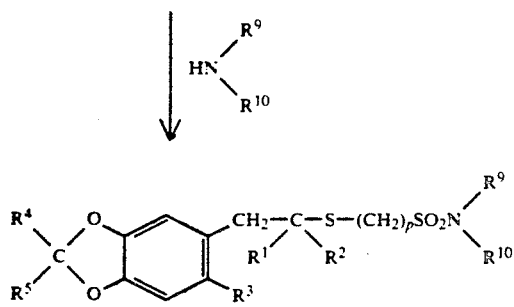

Preparation process E

Preparation of compounds of the general formula (I) wherein X represents a group of the formula: —S—

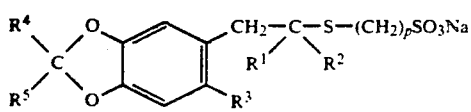

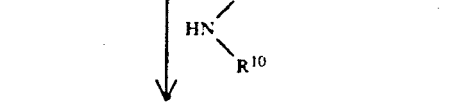

wherein $R^1$, $R^2$, $R^3$, $R^4$, $R^5$, $R^9$, $R^{10}$ and p are as defined above.

A sodium sulfonate of the general formula (X) is suspended in, for example, benzene or chloroform. Then, thionyl chloride or the like is added thereto and the reaction is conducted by heating under reflux to obtain an acid chloride of the compound (X). This product is reacted with an amine (XI) in the presence of a base in the absence of any solvent or in a solvent such as water, methanol, ethanol, benzene, dichloromethane, tetrahydrofuran or N,N-dimethylformamide to obtain an intended compound (XII). The bases usable herein include, for example, the amine (XI) per se, pyridine, N,N-dimethylaniline or triethylamine.

The compound (XII) is an intended one of the present invention represented by the general formula (I) wherein X represents —S—and A represents

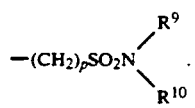

Preparation process F

Preparation of compounds of the general formula (I) wherein X represents a group of the formula:

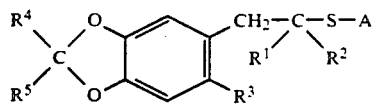

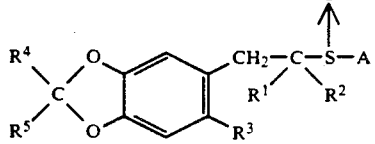

wherein A, $R^1$, $R^2$, $R^3$, $R^4$ and $R^5$ are as defined above.

A compound (IV) which also is an intended compound prepared by, for example, the above-described process is oxidized to obtain an intended compound (XIII). In this process, the compound (IV) is dissolved in a solvent selected from the group consisting of aromatic hydrocarbons such as benzene, toluene and xylene, halogenated hydrocarbons such as dichloromethane, chloroform and carbon tetrachloride, water, alcohols such as methanol and ethanol, ethyl acetate, acetone and acetic acid and then reacted with an equimolar amount of an oxidizing agent such as hydrogen peroxide, peracetic acid, m-chloroperbenzoic acid or sodium hypochlorite by an ordinary method under cooling with dry ice/ alcohol or with ice/water to obtain the intended sulfoxide compound (XIII).

Preparation process G

Preparation of compounds of the general formula (I) wherein X represents a group of the formula:

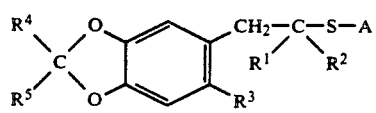

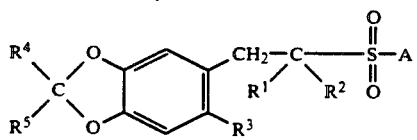

wherein A, $R^1$, $R^2$, $R^3$, $R^4$ and $R^5$ are as defined above.

In this process, an intended compound (IV) obtained by, for example, the above-described process is oxidized to obtain an intended compound (XIV). More particularly, the compound (IV) is dissolved in a solvent selected from the group consisting of aromatic hydrocarbons such as benzene, toluene and xylene, halogenated hydrocarbons such as dichloromethane, chloroform and carbon tetrachloride, water, alcohols such as methanol and ethanol, ethyl acetate, acetone and acetic acid. At least two equivalents of an oxidizing agent such as hydrogen peroxide, peracetic acid, m-chloroperbenzoic acid, sodium hypochlorite or sodium m-periodate is added thereto under cooling with ice or at room temperature to conduct the reaction and thereby to obtain an intended sulfone compound (XIV).

In another process, a sulfoxide compound (XIII) obtained by, for example, the preparation process F is dissolved in a solvent such as chloroform and then an oxidizing agent such as m-chloroperbenzoic acid is added to the solution to conduct the reaction.

Pharmacologically acceptable salts of the intended compounds (I) which are also intended products of the present invention can be prepared by, for example, reacting a compound of the general formula (I) wherein A represents

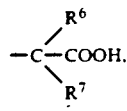

$R^3$ represents —(CH$_2$)$_n$COOH or A represents

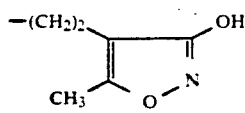

with sodium hydrogencarbonate, potassium hydrogencarbonate, sodium carbonate, potassium carbonate, sodium hydroxide or potassium hydroxide to obtain a pharmacologically acceptable salt such as sodium or potassium salt thereof.

Compound Group (I-e)

Preparation Process A

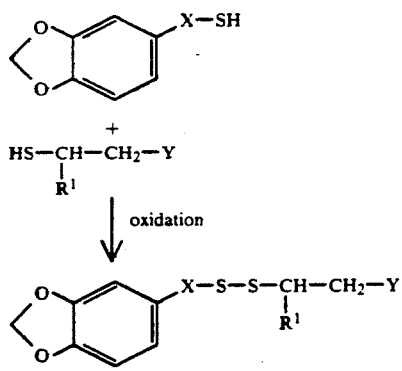

wherein X, R$^1$ and Y are as defined above.

That is, a thiol represented by the general formula (II) is reacted with a thiol represented by the general formula (III) to obtain a compound (I) which is one of the objective compounds according to the present invention.

More precisely, the reaction of a compound (II) with a compound (III) is carried out in the absence of any solvent or in the presence of a solvent inert to the reaction selected from among alcohols such as methanol, ethanol and propanol, acetic acid and an aqueous solution of potassium iodide or the like either under cooling with ice or heating or at a room temperature by using an oxidizing agent such as iodine, hydrogen peroxide, lead dioxide, oxygen, copper sulfate, ferric chloride, potassium permanganate, potassium ferricyanide, sulfuryl chloride, dimethyl sulfoxide, sulfur dioxide or phosphorus pentachloride according to an ordinary method to obtain a compound (I) which is one of the objective compounds.

Preparation Process B

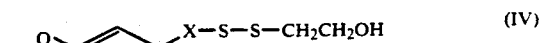

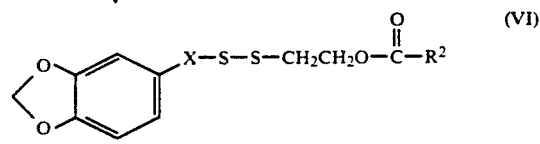

wherein X is as defined above; R$^2$ represents a lower alkyl, aryl or heteroaryl group and Hal represents a halogen atom.

More precisely, the reaction of an alcohol represented by the general formula (IV) with an acid halide represented by the general formula (V) is carried out in the absence of any solvent or in the presence of a solvent such as dichloromethane, chloroform, tetrahydrofuran or N,N-dimethylformamide by using a base such as pyridine, triethylamine, N,N-dimethylaniline, sodium carbonate or sodium hydrogencarbonate as a dehydrohalogenating agent to obtain a compound (VI) which is one of the objective compounds. In the reaction, pyridine can serve as both a solvent and a dehydrohalogenating agent. The reaction may be carried out either under cooling with water or under reflux by heating.

The preparation of pharmacologically acceptable salts of the compounds (I), which are also among the objective compounds according to the present invention, can be carried out by, for example, reacting a compound represented by the general formula (I) wherein Y is

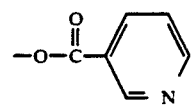

with hydrochloric, sulfuric or hydrobromic acid. Thus, the hydrochloride, sulfate or hydrobromide of the compound (I) is obtained.

Compound Group (I-f)

Preparation Process A

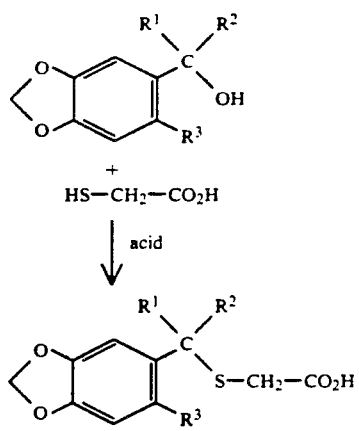

wherein the formulas (II) (IV), $R^1$, $R^2$ and $R^3$ are as defined above.

That is, an alcohol represented by the general formula (II) is reacted with a mercaptoacetic acid represented by the general formula (III) to obtain a compound represented by the general formula (IV) which is one of the objective compounds according to the present invention. This reaction is carried out in the absence of any solvent or in the presence of an organic solvent inert to the reaction selected from among aromatic hydrocarbons such as benzene, toluene and xylene; ethers such as ether, isopropyl ether, tetrahydrofuran and dioxane; halogenated hydrocarbons such as dichloromethane, chloroform and carbon tetrachloride; esters such as ethyl acetate; ketones such as acetone and methyl ethyl ketone; acetonitrile; dimethylformamide and acetic acid either under cooling with ice or heating or at a room temperature for several hours according to an ordinary process. The progress of the reaction is facilitated by using an acid such as sulfonic, p-toluenesulfonic or D-10-camphorsulfonic acid as a catalyst.

Preparation Process B

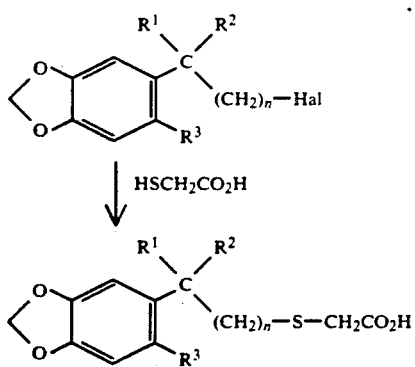

wherein the formulas (V) and (VI), Hal represents a halogen atom or a methanesulfonyloxy or p-toluenesulfonyloxy group and $R^1$, $R^2$, $R^3$ and n are as defined above.

That is, a compound represented by the general formula (V) is reacted with a mercaptoacetic acid represented by the formula (III) to obtain a compound represented by the general formula (VI) which is one of the objective compounds according to the present invention.

More precisely, the above reaction is carried out in the absence of any solvent or in the presence of an organic solvent inert to the reaction selected from among aromatic hydrocarbons such as benzene, toluene and xylene; ethers such as tetrahydrofuran and dioxane; ketones such as acetone and methyl ethyl ketone; alcohols such as methanol and ethanol; halogenated hydrocarbons such as chloroform and carbon tetrachloride; acetonitrile, N,N-dimethylformamide and dimentyl sulfoxide either under cooling with ice or heating or at a room temperature for several hours according to an ordinary process. The progress of the reaction can be facilitated by using an alkali metal carbonate or hydrogencarbonate such as sodium hydrogencarbonate or potassium or sodium carbonate; an alkali hydroxide such as sodium or potassium hydroxide; an organic base such as triethylamine, pyridine or diethylaniline or sodium hydride as a dehydrohalogenating, demethanesulfonating or de-p-toluenesulfonating agent.

In the preparation processes A and B, the halogen atom includes chlorine, bromine, and iodine, among which bromine and iodine are generally used.

Preparation Process C

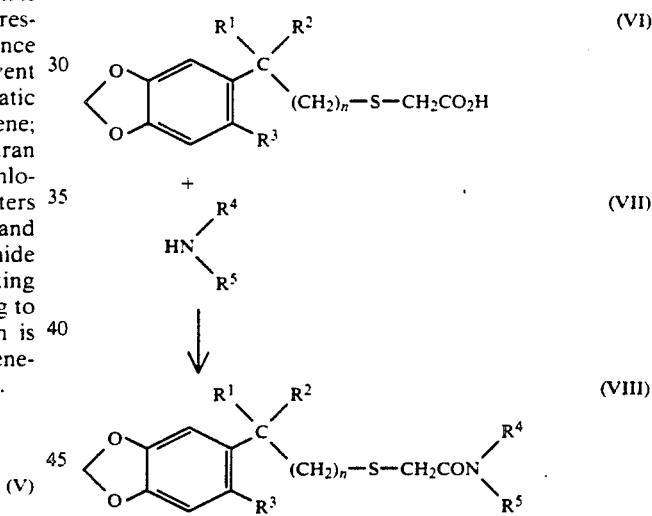

wherein $R^4$ and $R^5$ may be the same or different from each other and each represents a hydrogen atom or a lower alkyl group and $R^1$, $R^2$, $R^3$ and n are as defined above.

That is, a carboxylic acid represented by the general formula (VI) or a reactive derivative thereof, which can be prepared by, for example, the above preparation process A or B, is reacted with an amine represented by the general formula (VII) to obtain a compound represented by the general formula (VIII) which is one of the objective compounds according to the present invention.

The reactive derivative of the compound (VI) includes acid halides such as acid chloride and acid bromide; acid azide; reactive esters thereof with N-hydroxybenzotriazole, N-hydroxysuccinimide or the like; symmetric acid anhydride and mixed acid anhydride thereof with alkylcarbonic acid and p-toluenesulfonic acid.

When a compound (VI) having a free carboxyl group is used, it is preferred to carry out the reaction in the presence of a condensation agent such as dicyclohexyl-carbodiimide or 1,1'-carbonyldiimidazole.

The reaction is carried out by using a compound (VI) or a reactive derivative thereof and a compound (VII) in equimolar amounts or in such amounts that either of then is in slight excess over the other in an organic solvent inert to the reaction selected from among pyridine, tetrahydrofuran, dioxane, ether, benzene, toluene, xylene, methylene chloride, dichloroethane, chloroform, dimethylformamide, ethyl acetate, acetonitrile and the like.

When some kinds of the reactive derivatives are used, the addition of a base such as triethylamine, pyridine, picoline, lutidine, N,N-dimethylaniline, potassium carbonate or sodium hydroxide advantageously serves to make the reaction proceed smoothly The reaction temperature is not particularly limited and varies depending upon the kind of the reactive derivative used.

Preparation Process D

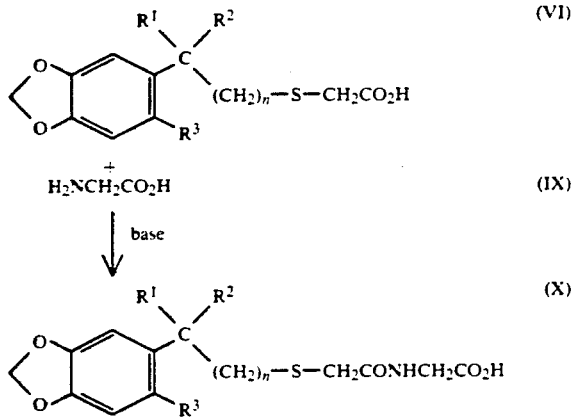

wherein $R^1$, $R^2$, $R^3$ and n are as defined above.

More precisely, a compound (VI), which can be prepared by the preparation process A or B, is dissolved in a solvent such as benzene, chloroform or dimethylfromamide, followed by the addition of thionyl chloride, oxalyl chloride, phosphorus oxychloride or phosphorus pentachloride. The obtained mixture was reacted either under cooling with ice or reflux by heating or at a room temperature to prepare an acid chloride of the compound (VI). A solution of glycine (IX) in an aqueous solution of sodium hydrogencarbonate, sodium carbonate or sodium hydroxide or the like is poured into the obtained reaction mixture under stirring and cooling with ice to carry out the reaction. Thus, a glycinamide (X) which is one of the objective compounds is obtained.

The glycinamide (X) obtained above corresponds to a compound represented by the general formula (I) wherein $R^4$ or $R^5$ is a carboxymethyl group and is thus one of the objective compounds according to the present invention.

The preparation of a pharmacologically acceptable salt of a compound (I), which is also one of the objective compounds according to the present invention, can be carried out by, for example, reacting a carboxylic acid (VI) corresponding to a compound represented by the general formula (I) wherein Y is —$CO_2H$ or a glycinamide (X) corresponding to a compound represented by the general formula (I) wherein $R^4$ or $R^5$ is a carboxymethyl group with an alkali hydrogen-carbonate such as sodium or potassium hydrogen-carbonate, an alkali carbonate such as sodium or potassium carbonate or an alkali hydroxide such as sodium or potassium hydroxide.

EXAMPLES OF THE INVENTION

The invention will be below illustrated in view of examples together with preparation of starting materials for the invention compounds, according to the compound groups (I-a) through (I-f).

Compound Group (I-a)

Preparative Example 1

2-(1,3-Benzodioxol-5-yl)-2-propanol

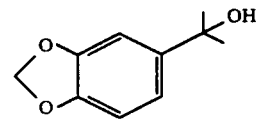

About 600 ml of 1.5 M methyllithium (solution in ether) was added to 500 ml of tetrahydrofuran. A suspension of 93.45 g of 5-acetyl-1,3-benzodioxole in 900 ml of tetrahydrofuran was added thereto under cooling at −20° C. The mixture was stirred under these conditions for 1 h. Water was added to the reaction mixture. The product was extracted with ethyl acetate, washed with a saturated aqueous common salt solution and dried over anhydrous magnesium sulfate. After filtration, the filtrate was concentrated to obtain 97 g of the intended compound in the form of an oil.

$^1$H-NMR(90 MHz, $CDCl_3$) δ;
1.54(s,6H), 1.72(bs,1H), 5.88(s,2H),
6.6~7.0(m,3H)

Preparative Example 2

2-(1,3-Benzodioxol-5-yl) propene

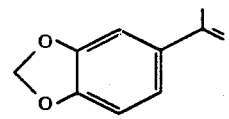

14.52 g of 2-(1,3-benzodioxol-5-yl)-2-propanol was dissolved in 200 ml of benzene. A catalytic amount of p-toluenesulfonic acid monohydrate was added to the solution and the mixture was heated under reflux in a short-neck Kjeldahl flask provided with a Dean-Stark reflux condenser for 2.5 h. The reaction mixture was washed with a saturated aqueous sodium hydrogencarbonate solution and then with a saturated aqueous common salt solution and dried over anhydrous magnesium sulfate. After filtration, the filtrate was concentrated to obtain 14.33 g of the intended compound in the form of an oil.

$^1$H-NMR(90 MHz, $CDCl_3$) δ;
2.08(bs,3H), 4.8~5.0(m,1H), 5.19(bs,
1H), 5.89(s,2H, 6.5~7.0(m,3H)

Preparative Example 3

1-(6-Methyl-1,3-benzodioxol-5-yl)ethanol

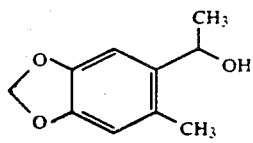

32 ml of 1.4 M solution of methyllithium in diethyl ether was dissolved in 50 ml of anhydrous tetrahydrofuran and the solution was cooled at −40° C. in a nitrogen atmosphere. 5.0 g of solid (6-methyl-1,3-benzodicxol-5-yl) carboxaldehyde was added to the solution and the temperature was elevated to room temperature gradually over 1 h. Water was added to the reaction mixture. After extraction with ether, the organic layer was washed with an aqueous common salt solution. After drying over magnesium sulfate, the solvent was distilled off to obtain a white solid, which was recrystallized from diisopropyl ether/ n-hexane to obtain 2.8 g of the intended compound in the form of white crystals.

mp.: 61°~62° C.
$^1$H-NMR(90 MHz, CDCl$_3$) δ;
1.39(d,J=7Hz,3H), 1.72(bs,1H), 2.22(s, 3H), 4.99(m,1H), 5.83(s,2H), 6.53(s,1H), 6.94(s,1H)

Preparative Example 4

1-(6-Methyl-1,3-benzodioxol-5-yl)-1-propanol

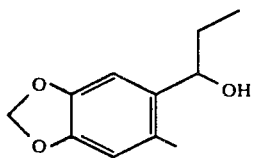

A solution of 2.0 g of (6-methyl-1,3-benzodioxol-5-yl)carboxaldehyde in 15 ml of anhydrous tetrahydrofuran was added dropwise at room temperature to a Grignard reagent prepared from 0.32 g of magnesium ribbon, 20 ml of anhydrous tetrahydrofuran and 1.4 g of bromoethane. The mixture was stirred for 2 h. A saturated ammonium chloride solution was added to the reaction mixture. The solvent was distilled off. After extraction with ethyl acetate followed by drying over magnesium sulfate and concentration under reduced pressure, the residue was purified according to silica gel column chromatography (ethyl acetate/ hexane=2:8) to obtain 2.27 g of the intended compound in the form of white crystals.

mp.; 71°~72° C.
$^1$H-NMR(90 MHz, CDCl$_3$) δ;
0.92(t,J=7Hz,3H), 1.68~1.92(m,2H), 1.80(bs,1H), 2.20(s,3H), 4.72(t,J=7Hz, 1H), 5.82(s,2H), 6.52(s,1H), 6.88(s,1H)

Preparative Example 5

1-(6-Ethyl-1,3-benzodioxol-5-yl)-1-propanol

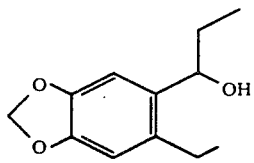

A solution of 3.2 g of (6-ethyl-1,3-benzodioxol-5-yl)carboxaldehyde in 10 ml of anhydrous tetrahydrofuran was added dropwise at room temperature to a Grignard reagent prepared from 0.54 g of magnesium ribbon, 10 ml of anhydrous tetrahydrofuran and 2.4 g of bromoethane. The reaction was conducted at that temperature for 2 h. A saturated aqueous ammonium chloride solution was added to the reaction mixture. The solvent was distilled off. After extraction with ethyl acetate followed by drying over magnesium sulfate and concentration under reduced pressure, 3.9 g of the crude alcohol was obtained in the form of a yellow oil, which was used in the subsequent reaction without purification.

$^1$H-NMR(90 MHz, CDCl$_3$) δ;
0.96(t,J=7Hz,3H), 1.18(t,J=7Hz,3H), 1.72(m,3H), 2.32~2.80(m,2H), 4.76(t,J=7Hz,1H), 5.84(s,2H), 6.58(s,1H), 6.88 (s,1H)

Preparative Example 6

5,6-Methylenedioxyindan-1-ol

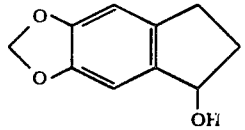

A solution of 30 g of 5,6-methylenedioxyindan-1-one in 120 ml of tetrahydrofuran was added dropwise to a suspension of 2.4 g of lithium aluminium hydride in 160 ml of anhydrous tetrahydrofuran under cooling with ice. The mixture was stirred at room temperature overnight. 2.4 ml of water, then 2.4 ml of 15% aqueous sodium hydroxide solution and finally 7.2 ml of water were added thereto and insoluble substances were filtered off. The filtrate was distilled and the residue was washed with diisopropyl ether to obtain 24.3 of the intended compound in the form of faint brown crystals.

mp.; 92°~94° C.
$^1$H-NMR(90 MHz, CDCl$_3$) δ;
1.76(d,J=7Hz,1H), 1.93(m,1H), 2.28~3.08(m,3H), 5.10(m,1H), 5.92(s,2H), 6.65(s,1H), 6.83(s,1H)

Example 1

[{1-(1,3-benzodioxol-5-yl)butyl}thio]acetic acid

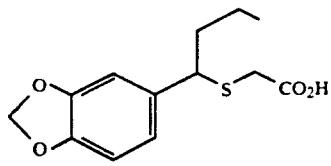

A mixture of 103 g of 1-(1,3-benzodioxol-5-yl)-1-butanol, 73.3 g of mercaptoacetic acid, 0.1 g of D-10-camphorsulfonic acid and 500 ml of benzene was heated under reflux for 2 h. 2,000 ml of ether was added to the reaction mixture. After washing with water, the product was redissolved in 750 ml of 1NNaOH and then in 100 ml thereof. The solution thus obtained was washed with ether and then with chloroform, acidified with concentrated hydrochloric acid and extracted with 800 ml and then 400 ml of ethyl acetate. The extract was washed with water, dried over magnesium sulfate and concentrated under reduced pressure to obtain 132 g of the crude product. It was purified according to silica gel column chromatography (ethyl acetate/ hexane/formic acid=100:900:1) to obtain 127 g of the intended compound in the form of a colorless oil. This oil was crystallized from n-hexane to obtain 115 g of the titled compound as a white crystalline powder. It was found to have a melting point of 59° to 61° C.

$^1$H-NMR(90 MHz, CDCl$_3$) δ;
0.88(m,3HO, 1.12~1.52(m,2H), 1.78~1.94(m,2H), 2.92 and 3.03(ABq,J=15Hz, 2H), 3.92(t,J=7Hz,1H), 5.92(s,2H), 6.68~6.80(m,3H)

Example 2

Sodium[{1-(1,3-benzodioxol-5-yl)butyl}thio]acetate

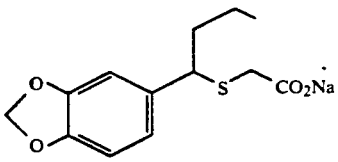

100 g of [{1-(1,3-benzodioxol-5-yl)butyl}thio] acetic acid was dissolved in 500 ml of ethanol. 372 ml of 1N-aqueous sodium hydroxide solution was added thereto. Ethanol and water were removed from the reaction mixture by azeotropic distillation and then ether was added to the residue to solidify it. A precipitate thus formed was recovered by filtration and dried to obtain 102 g of the intended compound in the form of a white powder.

mp.; 193°~207° C. (dec.)
$^1$H-NMR(400 DMSO-d$_6$)δ;
0.82(t,J=7.3Hz,3H), 1.11~1.26(m,2H),
1.59~1.77(m,2H), 2.64 and 2.73 (ABq,J=13.9Hz,2H), 3.87(dd,J=9.2Hz,6.2Hz,1H),
5.97(s,2H), 6.71(dd,J=8.1Hz,1.8Hz,1H),
6.79(d,J=8.1Hz,1H), 6.84(d,J=1.8Hz,1H)
MS(FAB) m/z; 291(MH$^-$)

EXAMPLE 3

[{2-(1,3-benzodioxol-5-yl)-2-propyl}thio]acetic acid

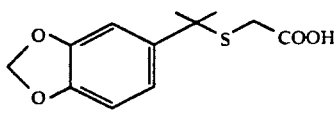

600 ml of benzene, 59.5 g of mercaptoacetic acid and a catalytic amount of D-10-camphorsulfonic acid were added to 97 g of 2-(1,3-benzodioxol-5-yl)-2-propanol and the mixture was heated under reflux for 4 h. The solvent was distilled off and the pH of the residue was adjusted to 10 with 1Naqueous sodium hydroxide solution. After washing with ethyl acetate, 4Nhydrochloric acid was added thereto under cooling with ice to acidify the aqueous layer. After extraction with chloroform, the extract was washed with water and dried over anhydrous magnesium sulfate. It was filtered and the filtrate was concentrated. The crystals thus formed were recrystallized from diisopropyl ether to obtain 62.70 g of the intended compound in the form of colorless crystals.

37.32 g of the intended compound was obtained also from 38.73 of 2-(1,3-benzodioxol-5-yl)propene in the same manner as that described above.

mp.; 78.5°~80° C.
$^1$H-NMR(90 MHz, CDCl$_3$) δ;
1.68(s,6H), 2.99(s,2H), 5.88(s,2H),
6.64(d,J=8.3Hz,1H), 6.86(dd,J=8.3Hz, 2.5Hz,1H), 6.99(d,J=2.5Hz,1H), 8.0~9.0(br,1H)

Example 4

Sodium [{2-(1,3-benzodioxol-5-yl)-2-propyl}thio]acetate

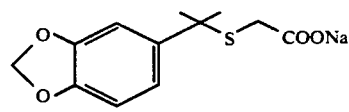

107.62 g of the intended compound in the form of colorless crystals was obtained from 99.88 g of [{2-(1,3-benzodioxol-5-yl)-2-propyl}thio]acetic acid in the same manner as that of Example 2.

mp.; 229.5°~230.5° C.
$^1$H-NMR(400MHz,DMSO-d$_6$) δ;
1.54(s,6H), 2.69(s,2H), 5.98(s,2H),
b 6.80(d,J=8.1Hz,1H), 6.88(dd,J=8.1Hz, 1.8Hz,1H), 7.06(d,J=1.8Hz,1H)
MS(FAB) m/z; 277(MH$^-$)

Example 5

[{1-(6-Methyl-1,3-benzodioxol-5-yl)ethyl}thio]acetic acid

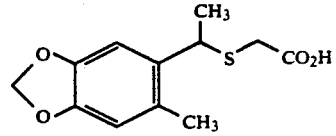

3.7 g of mercaptoacetic acid and a catalytic amount of D-10-camphorsulfonic acid were added to 3.2 g of 1-(6-methyl-1,3-benzodioxol-5-yl)ethanol and the mixture was heated under reflux in 100 ml of benzene for 1 h. The reaction mixture was washed with water and then extracted with a 1 1Nsodium hydroxide solution. The aqueous layer was washed with ethyl acetate, acidified with 1Nhydrochloric acid and extracted with chloroform. The organic layer was dried over magnesium sulfate and the solvent was distilled off to obtain a crystalline residue. After recrystallization from diisopropyl ether, 4.2 g of the intended compound was obtained in the form of white crystals.

mp.; 93.5°~94.5° C.
$^1$H-NMR(90 MHz, CDCl$_3$) δ;
1.51(d,J=7Hz,3H), 2.26(s,3H), 2.92 and
3.12(ABq,J=16Hz,2H), 4.39(q,J=7Hz,1H),
5.85(s,2H), 6.54(s,1H), 6.94(s,1H),
10.12(m,1H)

Example 6

Sodium [{1-(6-methyl-1,3-benzodioxol-5-yl)ethyl}thio] acetate

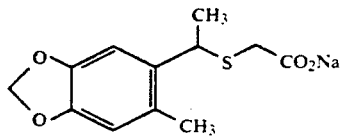

4.0 g of the intended compound in the form of white crystals was obtained from 3.85 g of [{1-(6-methyl-1,3-benzodioxol-5-yl)ethyl}thio]acetic acid in the same manner as that of Example 2.

mp.; 189°-192° C. (dec.)
$^1$H-NMR(400 MHz, DMSO-d$_6$) δ;
1.39(d,J=7.0Hz,3H), 2.24(s,3H), 2.78(s, 2H), 4.28(q,J=7.0Hz,1H), 5.92(m,2H), 6.68(s,1H), 6.92(s,1H)
MS(FAB) m/z; 277(MH$^-$)

Example 7

[{1-(6-Methyl-1,3-benzodioxol-5-yl)-1-propyl}thio] acetic acid

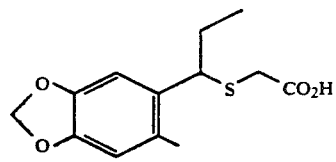

2.27 g of 1-(6-methyl-1,3-benzodioxol-5-yl)-1-propanol, 0.1 g of p-toluenesulfonic acid and 1.52 g of mercaptoacetic acid were dissolved in 80 ml of benzene. The solution was heated under reflux for 12 h while water was removed. The reaction mixture was poured into water. The aqueous layer was made alkaline and washed with ether. The aqueous layer was then acidified and extracted with chloroform. The extract was washed with water, dried over magnesium sulfate and concentrated under reduced pressure to obtain a faint yellow solid. It was purified according to silica gel column chromatography (ethyl acetate/ hexane=2:8) to obtain 2.83 g of the intended compound in the form of white crystals.

mp.; 98°~99° C.
$^1$H-NMR(90 MHz, CDCl$_3$) δ;
0.88(t,J=7Hz,3H), 1.60~2.12(m,2H), 2.24(s,3H), 2.96 and 3.08(ABq,J=14Hz,2H), 4.26(dd,J=9Hz,7Hz,1H), 5.92(s,2H), 6.62 (s,1H), 6.98(s,1H)

Example 8

Sodium [{1-(6-methyl-1,3-benzodioxol-5-yl)-1-propyl}thio]-acetate

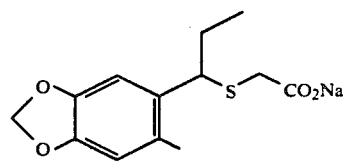

2.9 g of the intended compound in the form of white crystals was obtained from 2.83 g of [{1-(6-methyl-1,3-benzodioxol-5-yl)-1-propyl}thio]acetic acid in the same manner as that of Example 2.

mp. ; 215°~216° C. (dec.)
$^1$H-NMR(400 MHz, DMSO-d$_6$) δ;
0.78(t,J=7Hz,3H), 1.62~1.69(m,1H),
1.78~1.86(m,1H), 2.21(s,3H), 2.71 and
2.73(ABq,J=13.0Hz,2H), 4.07(dd,J=9.2Hz, 5.9Hz,1H), 5.93(m,2H), 6.69(s,1H), 6.86 (s,1H)
MS(FAB) m/z; 291(MH$^-$)

Example 9

Ethyl-[{1-(6-ethyl-1,3-benzodioxol-5-yl)-1-propyl}thio]-acetate

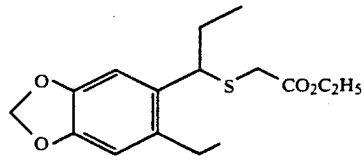

3.9 g of 1-(6-ethyl-1,3-benzodioxol-5-yl)-1-propanol, 0.1 g of p-toluenesulfonic acid and 3.35 g of ethyl mercaptoacetate were dissolved in 80 ml of benzene. The solution was heated under reflux for 12 h while water was removed. Water was added thereto. After extraction with benzene followed by drying over magnesium sulfate and concentration under reduced pressure, the product was purified according to silica gel column chromatography (ethyl acetate/hexane =1:9) to obtain 4.0 g of the intended compound in the form of a colorless, transparent oil.

$^1$H-NMR(90 MHz, CDCl$_3$) δ;
0.92(t,J=7Hz,3H), 1.16(t,J=7Hz,3H),
1.26(t,J=7Hz,3H), 1.50~2.12(m,2H),
2.44~2.80(m,2H), 2.96 and 3.08(ABq,J= 14Hz,2H), 4.16(q,J=7Hz,2H), 4.24(dd,J= 9Hz,7Hz,1H), 5.92(s,2H), 6.64(s,1H),
7.00 (s,1H)

Example 10

[{1-(6-Ethyl-1,3-benzodioxol-5-yl)-1-propyl}thio]acetic acid

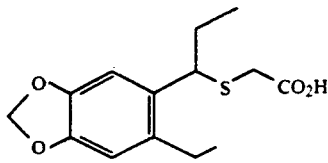

4.0 g of ethyl[1-{(6- ethyl-1,3-benzodioxol-5-yl)--propyl}thio]acetate and 2.6 g of sodium hydroxide were dissolved in a mixture of 20 ml of water and 20 ml of ethanol. The solution was heated under reflux for 2 h. Ethanol was distilled off and the residue was washed with ether. The aqueous layer was acidified and extracted with chloroform. The extract was washed with water, dried over magnesium sulfate and concentrated under reduced pressure. The residue was purified according to silica gel column chromatography (ethyl acetate/hexane =2:8) to obtain 2.8 g of the intended compound in the form of white crystals.

mp.; 88°~89° C.
$^1$H-NMR(90 MHz, CDCl$_3$) δ;
0.92(t,J=7Hz,3H), 1.16(t,J=7Hz,3H),
1.56~2.12(m,2H), 2.24~2.76(m,2H),
2.95 and 3.08(ABq,J=16Hz,2H), 4.20(t,J=7Hz,1H), 5.88(s,2H), 6.58(s,1H), 6.90 (s,1H), 9.72(bs,1H)

EXAMPLE 11

Sodium [{1-(6-ethyl-1,3-benzodioxol-5-yl)-1-propyl}thio]-acetate

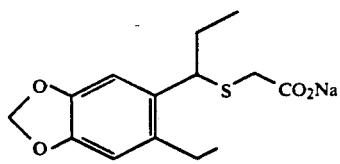

3.0 g of the intended compound in the form of white crystals was obtained from 2.83 g of [{1-(6-ethyl-1,3-benzodioxol-5-yl)-1-propyl}thio]acetic acid in the same manner as that of Example 2.

mp.; 221°~223° C. (dec.)
$^1$H-NMR(400MHz,DMSO-d$_6$) δ;
0.79(t,J=7Hz,3H), 1.09(t,J=7Hz,3H),
1.63~1.70(m,1H), 1.80~1.88(m,1H),
2.47~2.56(m,1H), 2.60~2.67(m,1H),
2.73 and 2.77(ABq,J=13.9Hz,2H), 4.06 (dd, J=8.4Hz,6.2Hz,1H), 5.93(m,2H), 6.69 (s,1H), 6.87(s,1H)
MS(FAB) m/z; 305(MH$^-$)

EXAMPLE 12

[{(6-Methyl-1,3-benzodioxol-5-yl) methyl}thio]acetic acid

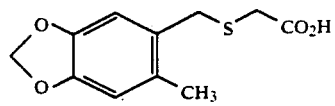

A suspension of 6.0 g of 5-chloromethyl-6-methyl-1,3-benzodioxole, 6.0 g of mercaptoacetic acid and 6.5 g of sodium hydroxide in 130 ml of 50% hydrous ethanol was heated under reflux for 1 h. The reaction mixture was concentrated. Water was added thereto and the mixture was washed with ethyl acetate. The aqueous layer was acidified with 1Nhydrochloric acid. After extraction with chloroform, the extract was dried over magnesium sulfate. The solvent was distilled off and the product was isolated according to silica gel column chromatography (chloroform). The crystals thus obtained were recrystallized from diisopropyl ether to obtain 1.6 g of the intended compound in the form of white crystals.

mp.; 90°~92° C.
$^1$H-NMR(90 MHz, CDCl$_3$) δ;
2.30(s,3H), 3.14(s,2H), 3.76(s,2H),
5.86(s,2H), 6.60(s,1H), 6.70(s,1H)

Example 13

Sodium [{(6-methyl-1,3-benzodioxol-5-yl)methyl}thio]acetate

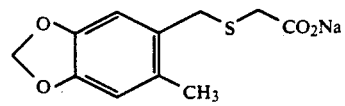

1.7 g of the intended compound in the form of white crystals was obtained from 1.6 g of [{(6-methyl-1,3-benzodicxol-5-yl)methyl}thio]acetic acid in the same manner as that of Example 2.

mp.; 214°~215° C. (dec.)
$^1$H-NMR(400MHz,DMSO-d$_6$) δ;
2.23(s,3H), 2.85(s,2H), 3.63(s,2H),
5.93(s,2H), 6.73(s,1H), 6.81(s,1H)
MS(FAB,Neg) m/z; 239(M-Na$^-$)

Example 14

{(5,6-Methylenedioxyindan-1-yl)thio}acetic acid

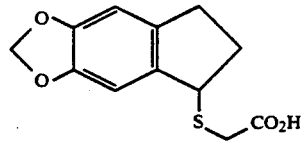

0.94 g of 5,6-methylenedioxyindan-1-yl, 0.98 g of mercaptoacetic acid and a catalytic amount of D-10-camphorsulfonic acid were heated in 30 ml of benzene under reflux for 30 min. The reaction mixture was washed with water and extracted with a 1Naqueous sodium hydroxide solution. The aqueous layer was acidified with 1Nhydrochloric acid and extracted with chloroform. The organic layer was dried over magnesium sulfate. The solvent was distilled off and the product was isolated according to silica gel column chromatography (chloroform) to obtain 1.14 g of the intended compound in the form of faint brown oil.

¹H-NMR(90 MHz, CDCl₃) δ;
2.07~3.09(m,4H), 3.22(s,2H), 4.37(m,1H), 5.88(s,2H), 6.61(s,1H), 6.77(s,1H) 9.72(m,1H)

Example 15

Sodium {(5,6-methylenedioxyindan-1-yl)thio}acetate

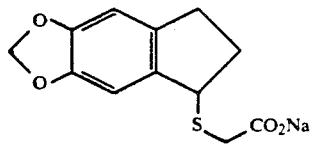

2.3 g of the intended compound in the form of white crystals was obtained from 2.4 g of {(5,6-methylenedioxyindan-1-yl)thio}acetic acid in the same manner as that of Example 2.

mp.; 210°~224° C. (dec.)
¹H-NMR(400MHz,DMSO-d₆) δ;
2.01(m,1H), 2.39(m,1H), 2.67(ddd,J=15.4 Hz,8.4Hz,4.4Hz,1H), 2.84(m,1H), 2.89, 2.89 and 2.94(ABq,J=13.6Hz,2H), 4.28(dd, J=7.3Hz,4.0Hz,1H), 5.96(m,2H), 6.76(s,1H), 6.84(s,1H)
MS(FAB,Neg) m/z; 251(M-Na⁻)

Example 16

{(6,7-Methylenedioxytetralin-1-yl)thio}acetic acid

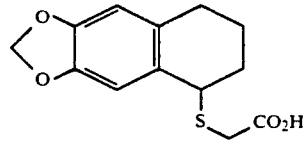

1.2 g of 6,7-methylenedioxy-1-tetralone was added to a suspension of 0.2 g of lithium aluminum hydride in 20 ml of tetrahydrofuran under cooling with ice. The mixture was stirred at room temperature overnight and cooled with ice/water. 0.2 ml of water, then 0.2 ml of a 15% aqueous sodium hydroxide solution and finally 0.6 ml of water were added thereto. Insoluble substances were removed by filtration. The filtrate was concentrated to obtain a crystalline residue. 1.1 g of mercaptoacetic acid and a catalytic amount of D-10-camphosulfonic acid were added to the residue and the mixture was heated in 30 ml of benzene under reflux for 1 h. The reaction mixture was washed with water. After extraction with a 1Naqueous sodium hydroxide solution, the aqueous layer was acidified with 1N hydrochloric acid. After extraction with chloroform, the extract was dried over magnesium sulfate and the solvent was distilled off. The crystalline residue thus obtained was treated according to silica gel column chromatography (chloroform) to obtain 1.4 g of the intended compound in the form of white crystals.

mp.; 138°~139° C.
¹H-NMR(90 MHz, CDCl₃) δ;
1.6~2.2(m,4H), 2.65(m,2H), 3.20 and 3.34(ABq,J=16Hz,2H), 4.18(m,1H), 5.83 (s,2H), 6.45(s,1H), 6.79(s,1H)

Example 17

Sodium {(6,7-methylenedioxytetraolin-1-yl)thio}acetate

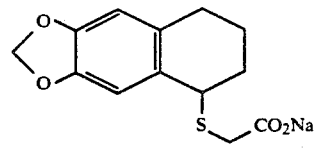

1.3 g of the intended compound in the form of white crystals was obtained from 1.3 g of {(6,7-methylenedioxytetralin-1-yl)thio}acetic acid in the same manner as that of Example 2.

mp.; 180°~184° C. (dec.)
¹H-NMR(400MHz,DMSO-d₆) δ;
1.63(m,1H), 1.85(m,1H), 1.95(m,2H), 2.59(m,2H), 2.89 and 3.04(ABq,J=13.9Hz, 2H), 4.18(m,1H), 5.91(m,2H), 6.55(s,1H), 6.93(s,1H)
MS(FAB) m/z; 289(MH⁻)

Example 18

[{1-(6-Methyl-1,3-benzodioxol-5-yl)ethyl}sulfinyl]acetic acid

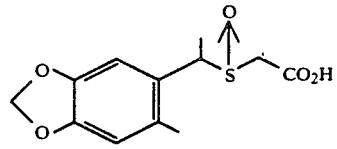

1.7 g of 80% m-chloroperbenzoic acid was added to a solution of 2.0 g of [{1-(6-methyl-1,3-benzodioxol-5-yl)ethyl}thio]acetic acid in 40 ml of chloroform under cooling with ice. The mixture was stirred at room temperature overnight and a crystalline insoluble matter was recovered by filtration and washed with ether to obtain 0.24 g of the intended compound (as a single diastereomer) in the form of white crystals.

mp.; 129°~130° C. (dec.)
¹H-NMR(90 MHz, DMSO₆) δ;
1.53(d,J=7Hz,3H), 2.23(s,3H), 3.13 and 3.54(ABq,J=14Hz,2H), 4.26(q,J=7Hz,1H), 5.92(s,2H), 6.72(s,1H), 6.86(s,1H)

The filtrate obtained by the above-mentioned treatment was concentrated to obtain a crystalline residue, which was washed with benzene. The washing was concentrated to obtain a crystalline residue, which was washed with ether to obtain 1.4 g of the intended compound (as the other diastereomer) in the form of white crystals.

mp.; 111°~112° C. (dec.)
¹H-NMR(90MHz, DMSO-d₆) δ;
1.52(d,J=7Hz,3H), 2.26(s,3H), 3.51 and 3.60(ABq,J=14Hz,2H), 4.27(q,J=7Hz,1H), 5.92(s,2H), 6.73(s,3H)

EXAMPLE 19

[{1-(1,3-Benzodioxol-5-yl)-1-butyl}sulfinyl]acetic acid

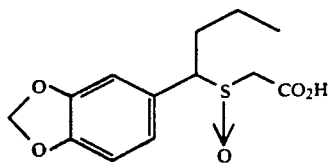

2.0 g of the intended compound (as a diastereomer mixture of 3:1 as determined by NMR) in the form of a colorless oil was obtained from 2.9 g of [{1-(1,3-benzodioxol-5-yl)-1-butyl}thio]acetic acid in the same manner as that of Example 18.

$^1$H-NMR(400MHz, DMSO-d$_6$) δ;
0.86(t,J=7.3Hz,3H×⅔), 0.88(t,J=7.6Hz, 3H×⅓), 1.14~1.33(m,2H), 1.80~2.07 (m,2H), 2.89 and 3.55(ABq,J=14.4Hz,2H× ⅓), 3.40 and 3.43(ABq,J=14.3Hz,2H×⅔), 3.85(dd,J=9.2Hz,7.0Hz,1H×⅓), 4.04(dd, J=11.9Hz, 3.9Hz,1H×⅔), 6.02(s,2H), 6.74 ~6.95(m,3H)

EXAMPLE 20

[{1-(6-Methyl-1,3-benzodioxol-5-yl)ethyl}sulfonyl]acetic acid

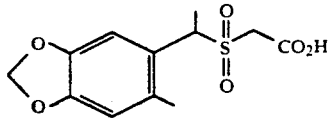

3.4 g of 80% m-chloroperbenzoic acid was added to a solution of 2.0 g of [{1-(6-methyl-1,3-benzodioxol-5-yl)ethyl}thio]acetic acid under cooling with ice. The mixture was stirred at room temperature overnight. Benzene was added thereto and crystals thus formed were recovered by filtration. The crystals were dissolved in ethyl acetate and an insoluble substance was filtered out. The filtrate was concentrated and a crystalline residue thus formed was washed with ether to obtain 0.9 g of the intended compound in the form of white crystals.

mp.; 143°~144° C. (dec.)
$^1$H-NMR(90MHz,DMSO-d$_6$) δ;
1.62(d,J=7Hz,3H), 2.27(s,3H), 3.96 and 4.36(ABq,J=15Hz,2H), 4.92(q,J=7Hz,1H), 5.94(s,2H), 6.74(s,1H), 6.87(s,1H)

Compound Group (I-b)

Example 1 (Compound 1)

2-(1,3-Benzodioxol-5-yl)ethanethiol

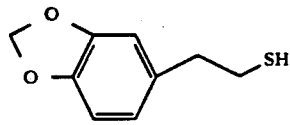

750 g of 5-(2-bromoethyl)-1,3-benzodioxole was dissolved in 1 l of ethanol. 312 g of thiourea was added to the solution and the mixture was heated under reflux on a boiling water bath for 2 h. The reaction mixture was cooled. A solution of 300 g of sodium hydroxide in 1 l of water was added thereto and the mixture was heated under reflux on a boiling water bath for 45 min. After cooling, 3 l of water was added thereto and the product was extracted with 5 l of ethyl acetate. The extract was washed with dilute hydrochloric acid. It was then washed with water until the washing became substantially neutral and dried over anhydrous sodium sulfate. The solvent was distilled off at 40° C. to obtain about 570 g of a faint yellow oil. It was purified according to column chromatography with about 3 kg of silica gel (hexane : benzene=2:1) to obtain 310 g of the intended compound in the form of a colorless oil.

NMR (90 MHz, CDCl$_3$) δ;
1.36(m,1H), 2.6~2.9(m, 4H), 5.87(s,2H), 6.50~6.74(m,3H)

Example 2 (Compound 21)

Sodium 2-amino-3-[{2-(1,3-benzodioxol-5-yl)ethyl}thio]-propionate

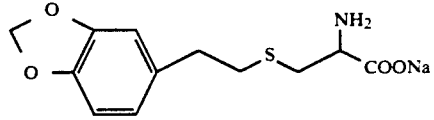

406 g of L-cysteine.HCl.H$_2$O was suspended in a mixture of 1 l of water and 500 ml of ethanol. A solution of 370 g of sodium hydroxide in 1.5 l of water was added to the suspension. 527 g of 5-ethenyl-1,3-benzodioxole and then 500 ml of ethanol were added thereto and the mixture was heated under reflux for 2.5 h to conduct the reaction. Ethanol was distilled off under reduced pressure and the residue was filtered. The filtrate was acidified with acetic acid to form colorless crystals, which were recovered by filtration and recrystallized from 3 l of water to obtain 250 g of 2-amino-3-[{2-(1,3-benzodioxol-5-yl)ethyl}thio]propionic acid in the form of colorless needles.

The crystals were dissolved in a solution of 37 g of sodium hydroxide in 1 l of water. The solution was filtered and the filtrate was concentrated into about a half volume. 1.5 l of ethanol was added thereto to recrystallize the product. 100 g of the intended product was obtained in the form of colorless crystals.

m.p.: 170° to 172° C.
NMR (400 MHz, DMSO-d$_6$) δ;
2.64~2.74(m,5H), 2.91(dd,J=12.8Hz,3.7 Hz,1H), 3.01(m,1H), 3.3(m,2H), 5.95(s, 2H), 6.68(dd,J=8.1Hz,1.8Hz,1H), 6.79(d, J=8.1Hz,1H), 6.83(d,J=1.8Hz,1H)
MS (FAB) m/z; 314(M$^+$+Na), 292 (M$^+$+1)

| Elementary analysis for C$_{12}$H$_{14}$NO$_4$SNa: | | | |
|---|---|---|---|
| | C | H | N |
| calculated (%) | 49.48 | 4.84 | 4.81 |
| found (%) | 49.58 | 4.91 | 4.91 |

Example 3 (compound 8)

Sodium [{2-(1,3-benzodioxol-5-yl)ethyl}thio]acetate

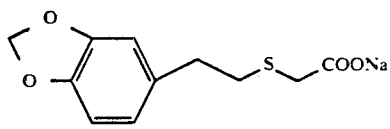

100 g of 2-(1,3-benzodioxol-5-yl)ethanethiol and 75.1 g of bromoacetic acid were dissolved in 1 l of ethanol. A solution of 44 g of sodium hydroxide in 125 ml of water and then 2 l of ethanol were added thereto. The mixture was heated under reflux for 3 h. The reaction mixture was concentrated under reduced pressure. 2.5 l of water was added thereto. The mixture was made alkaline with a 1N sodium hydroxide solution, washed with 35% hydrochloric acid, extracted with ethyl acetate, washed with water four times and dried over sodium sulfate. The solvent was distilled off under reduced pressure to obtain 121 g of [{2-(1,3-benzodioxol-5-yl)ethyl}thio]acetic acid in the form of a faint yellow oil.

NMR (90 MHz, CDCl$_3$) δ;
2.80(s,4H), 3.20(s,2H), 5.85(s,2H),
6.44~6.74(m,3H0, 10.24(bs,1H)
MS (EI) m/z; 240(M$^-$), 135(Base)

A solution of 20.27 g of sodium hydroxide in 200 ml of water was added to the oily product to obtain a solution. After recrystallization from dilute ethanol, 102.5 g of the intended compound was obtained in the form of colorless crystals.

m.p.: 224° to 226° C.
NMR (400 MHz, DMSO-d$_6$) δ;
2.69(m,4H), 2.95(s,2H), 5.95(s,2H),
6.66(dd,J=7.7Hz,1.5Hz,1H), 6.79(d,J=7.7 Hz,1H), 6.81(d,J=1.5Hz,1H)
MS (FAB) m/z; 285(M$^+$+Na), 263(M$^+$+1)

| Elementary analysis for C$_{11}$H$_{11}$O$_4$SNa: | | |
|---|---|---|
| | C | H |
| calculated (%) | 50.38 | 4.23 |
| found (%) | 50.27 | 4.31 |

Example 4 (Compound 17)

3-[{2-(1,3-Benzodioxol-5-yl)ethyl}thio]propionamide

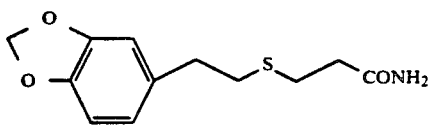

5 g of 2-(1,3-benzodioxol-5-yl)ethanethiol and 4 g of acrylamide were dissolved in 100 ml of ethanol and the solution was heated under reflux to conduct the reaction for 20 h. The reaction mixture was cooled with ice. 100 ml of ethanol was added thereto and crystals thus formed were recovered by filtration to obtain 4.2 g of the intended compound in the form of colorless needles.

m.p.: 103° to 104° C.
NMR (90 MHz, CDCl$_3$) δ;
2.50(m,2H), 2.89(s,4H), 2.73~2.93(m, 2H), 5.6(br,s,2H), 5.91(s,2H), 6.68(m, 3H)

MS (EI) m/z; 253(M$^-$), 149, 136(Base)

Example 5 (Compound 25)

Ethyl [{2-(1,3-benzodioxol-5-yl)ethyl}thio]acetate

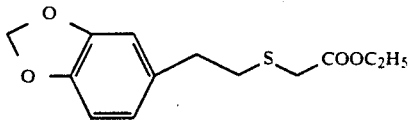

3.24 g of ethyl thioglycolate was added to 6 g of 5-ethenyl-1,3-benzodioxole and the mixture was stirred at room temperature for 14 h. The reaction product was purified according to silica gel column chromatography (benzene : ethyl acetate=40:1) to obtain 5 g of the intended compound in the form of a colorless oil.

NMR (90 MHz, CDCl$_3$) δ;
1.27(t,J=7Hz,3H), 280(s,4H), 3.18(s, 2H), 4.15(q,J=7Hz,2H), 5.86(s,2H), 6.62 (m,3H)
MS (EI) m/z; 268(M$^+$), 149(Base)

Example 6 (Compound 26)

5-[2-(Methylsulfinyl)ethyl]-1,3-benzodioxole

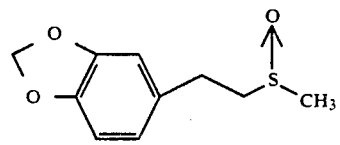

3 g of 5-{2-(methylthio)ethyl}-1,3-benzodioxole was dissolved in 100 ml of chloroform. An equimolar amount of m-chloroperbenzoic acid was added to the solution under stirring under reflux with dry ice/ alcohol to conduct the reaction for 1 h. 300 ml of chloroform and 300 ml of water were added thereto and then sodium carbonate was added to the mixture until the aqueous layer became alkaline. After separation of the layers, the chloroform layer was washed with water twice and dried over sodium sulfate. The solvent was distilled off under reduced pressure. The oily product was purified according to silica gel column chromatography (chloroform : methanol=20:1) to obtain 1.6 g of the intended compound in the form of a colorless oil.

NMR (90 MHz, CDCl$_3$) δ;
2.55(s,3H), 2.74~3.12(m,4H), 5.87(s, 2H), 6.64(m,3H)
MS (EI) m/z; 212(M$^+$), 196, 148(Base)

Example 7 (Compound 28)

5-{2-(Methylsulfonyl)ethyl}-1,3-benzodioxole

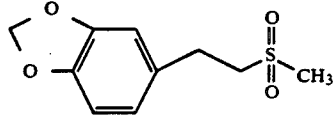

3.5 g of 5-{2-(methylthio)ethyl}-1,3-benzodioxole was dissolved in 100 ml of chloroform. 8.8 g of m-chloroperbenzoic acid was added to the solution under cooling with ice/water to conduct the reaction for 2 h. 300 ml of chloroform and 300 ml of water were added thereto and then sodium carbonate was added to the mixture until the aqueous layer became alkaline. After separation of the layers, the chloroform layer was washed with water twice and dried over sodium sulfate. The solvent was distilled off under reduced pressure. After recrystallization from ethyl acetate/ isopropyl ether, 3 g of the intended compound was obtained in the form of colorless needles.

NMR (90 MHz, CDCl₃) δ;
2.80(s,3H), 2.93~3.36(m,4H), 5.88(s, 2H), 6.65(m,3H)
MS (EI) m/z; 228(M⁺), 148(Base)

Example 8 (Compound 22)

[{2-(1,3-Benzodioxol-5-yl)ethyl}thio]ethyl nicotinate

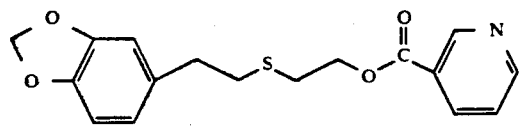

4 g of [{2-(1,3-benzodioxol-5-yl)ethyl}thio]-ethanol prepared in the same manner as that of Example 2 was dissolved in 20 ml of pyridine. 50 ml of benzene was added to the solution. 4.7 g of nicotinic chloride hydrochloride was added thereto under stirring and the mixture was heated on a boiling water bath for 2 h. The reaction mixture was poured into ice/water. 100 ml of water and sodium hydrogen-carbonate were added thereto to make it weakly alkaline. After extraction with ethyl acetate, the ethyl acetate layer was washed with water four times and dried over sodium sulfate. The solvent was distilled off and the residue was purified according to silica gel column chromatography (benzene : ethyl acetate=3:1) to obtain 2 g of the intended compound in the form of a colorless oil.

NMR (90 MHz, CDCl₃) δ;
2.80(s,4H), 2.85(t,J=7Hz,2H), 4.44(t,J=7Hz,2H), 5.86(s,2H), 6.61(m,3H), 7.31 (m,1H), 8.20(m,1H), 8.69(m,1H), 9.13(m,1H)
MS (EI) m/z; 331(M⁺, Base), 148

Example 9 (Compound 23)

N-[2-{(1,3-Benzodioxol-5-yl)ethyl}thio]-1-oxoethyl]-aminoacetic acid

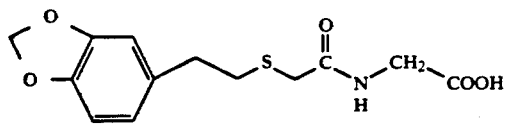

5.3 g of [{2-(1,3-benzodioxol-5-yl)ethyl}thio]-acetic acid prepared in Example 2 was dissolved in 20 ml of benzene. 6.43 ml of thionyl chloride was added to the solution and the mixture was heated under reflux for 2 h to conduct the reaction. The solvent was distilled off under reduced pressure. 3 g of glycine was added to a solution of 1.6 g of sodium hydroxide in 10 ml of water. The reaction product obtained as above was added thereto under stirring under cooling with ice/water. The mixture was stirred at about 10° C. for 15 min and then the reaction was conducted at room temperature for 2 h. Water was added to the reaction mixture, which was acidified with concentrated hydrochloric acid. The precipitates thus formed were recovered by filtration, washed with water and recrystallized repeatedly from dilute ethanol to obtain 3 g of the intended compound in the form of colorless needles.

m.p.: 121.5° to 122.5° C.
NMR (90 MHz, CDCl₃-CD₃OD) δ;
2.84(s,4H), 3.26(s,2H), 3.99(s,2H), 5.92(s,2H), 6.71(m,3H), 7.54(s,1H)
MS (EI) m/z; 297(M⁺), 149(Base), 148

In the following Examples 10 to 27, compounds of the following general formula (I') wherein R was a group shown below were prepared.

Preparation processes A, B, C, D and E were the same as those of Examples 2, 3, 4, 5 and 9, respectively.

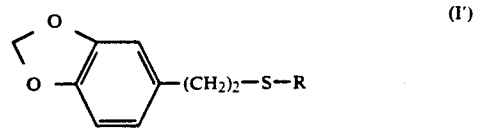

(I')

Example 10 (Compound 2)

R = —CH₂CH₂CH₃ (preparation process B)

NMR (90 MHz, CDCl₃) 67 ;
0.98(t,J=7Hz,3H), 1.4~1.8(m,2H), 2.51 (t,J=7Hz,2H), 2.75(s,4H), 5.91(s,2H), 6.7(m,3H)
MS (EI) m/z; 224(M⁺), 148, 135, 77(Base)

Example 11 (Compound 3)

R = —CH₂CH₂OH (preparation process B)

NMR (90 MHz, CDCl₃) δ;
2.72(t,J=6Hz,2H), 2.78(s,4H), 3.72(q,J=6Hz,2H), 5.92(s,2H), 6.6~6.8(m,3H)
MS (FD) m/z; 226(M⁺)

| Elementary analysis for C₁₁H₁₄O₃S: | | | |
|---|---|---|---|
| | C | H | S |
| calculated (%) | 58.39 | 6.24 | 14.17 |
| found (%) | 58.61 | 6.22 | 13.83 |

Example 12 (Compound 4)

R = —(CH₂)₃OH (preparation process B)

NMR (90 MHz, CDCl₃) δ;
1.59(m,1H), 1.85(m,2H), 2.66(t,J=7Hz, 2H), 2.78(s,4H), 3.76(m,2H), 5.93(s,3H), 6.70(m,3H)
MS (EI) m/z; 240(M⁺), 148(Base), 135

Example 13 (Compound 5)

R = —CH₂—CH—CH₂OH (preparation process A)
          |
          OH

NMR (90 MHz, CDCl₃) δ;
2.02(t,J=6Hz,1H), 2.6~2.9(m,3H), 2.80 (s,4H), 3.4~3.9(m,3H), 5.94(s,2H), 6.70(m,3H)
MS (EI) m/z;
256(M⁺), 149, 135, 91, 77, 65(Base)

Example 14 (Compound 6)

R = —CH$_2$CH$_2$OCH$_3$ (preparation process B)

NMR (90 MHz, CDCl$_3$) δ;
2.68(t,J=7Hz,2H), 2.76(s,4H), 3.33(s,3H), 3.52(t,J=7Hz,2H), 5.87(s,2H), 6.62(m,3H)
MS (EI) m/z;
240(M$^+$), 148, 135, 77(Base)

Example 15 (Compound 7)

R = —CH$_2$— 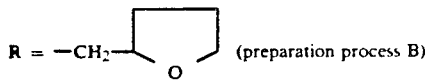 (preparation process B)

NMR (90 MHz, CDCl$_3$) δ;
1.5~2.2(m,4H), 2.46(m,2H), 2.79(s,4H), 2.6~3.1(m,3H), 5.91(s,2H), 6.68(m,3H)
MS (EI) m/z; 266(M$^+$), 149(Base)

Example 16 (Compound 9)

R = —CH$_2$CH$_2$COOH (free form) (process A, B, or D)

m.p.: 63.0° to 64.0° C.
NMR (90 MHz, CDCl$_3$) δ;
2.77(m,4H), 2.50~2.90(m,4H), 5.91(s,2H), 6.67(m,3H), 8.0(br,s1H)
MS (EI) m/z; 254(M$^+$, Base), 148, 135

R = —CH$_2$CH$_2$COONa (preparation process A, B or D)

m.p.: 187° to 189° C.
NMR (400 MHz, d$_6$-DMSO) δ;
2.11(m,2H), 2.62~2.74(m,6H), 5.95(s,2H), 6.68(dd,J=7.7Hz,1.5Hz,1H), 6.79(d,J=7.7Hz,1H), 6.82(d,J=1.5Hz,1H)
MS (FAB) m/z; 299(M$^+$+Na), 277(M$^+$+1)

| Elementary analysis for C$_{12}$H$_{13}$O$_4$SNa; | | |
|---|---|---|
| | C | H |
| calculated (%) | 52.17 | 4.74 |
| found (%) | 52.15 | 4.80 |

Example 17 (Compound 10)

R = —(CH$_2$)$_3$COONa (preparation process B)

NMR (90 MHz, D$_2$O) δ;
1.90(m,2H), 2.30(t,J=7Hz,2H), 2.59(t,J=7Hz,2H), 2.85(s,4H), 5.94(s,2H), 6.80(m,3H)
MS (FAB) m/z; 313(M$^+$+Na), 291(M$^+$+1)

Example 18 (Compound 1)

R = —(CH$_2$)$_4$COONa (preparation process B)

NMR (90 MHz, CDCl$_3$) δ;
1.69(m,4H), 2.46(m,4H), 2.74(s,4H), 5.87(s,3H), 6.61(m,3H), 7.20(br,1H)
MS (Na salt) (FAB) m/z;
327(M$^+$+Na), 305(M$^+$+1)

Example 19 (Compound 12)

R = —(CH$_2$)$_5$COONa (preparation process B)

m.p.: 248° to 251° C.
NMR (90 MHz, D$_2$O ) δ;
1.16~1.70(m,6H), 2.17(m,2H), 2.45(m,2H), 2.66(s,4H), 5.82(s,2H), 6.66(m,3H)
MS (FAB) m/z; 341(M$^+$+Na), 319(M$^+$+1)

Example 20 (Compound 13)

R = —CH—CH$_2$COOH (free form) (preparation process B)
    |
   CH$_3$

NMR (90 MHz, CDCl$_3$) δ;
1.35(d,J=7Hz,3H), 2.57(m,2H), 2.76(s,4H), 3.18(m,1H), 5.86(s,2H), 6.62(m,3H), 7.2(br,1H),

R = —CH—CH$_2$COONa (preparation process B)
    |
   CH$_3$ m.p.: 126° to 128.5° C.
NMR (400 MHz, DMSO-d$_6$) δ;
1.18(d,J=6.6Hz,3H), 1.88(dd,J=14.7Hz,9.9Hz,1H), 2.20(dd,J=14.7Hz,4.4Hz,1H), 2.69(m,4H), 3.14(m,1H), 5.95(s,2H), 6.68(dd,J=8.0Hz,1.8Hz,1H), 6.79(d,J=8.0Hz,1H), 6.82(d,J=1.8Hz,1H)
MS (FAB) m/z; 313(M$^+$+Na), 291(M$^+$+1)

| Elementary analysis for C$_{13}$H$_{15}$O$_4$SNa.½H$_2$O | | |
|---|---|---|
| | C | H |
| calculated (%) | 51.39 | 5.47 |
| found (%) | 51.22 | 5.52 |

Example 21 (Compound 14)

R = —CH—CH$_2$COOH (preparation process D)
    |
   COOH m.p.: 139° to 140° C.
NMR (90 MHz, DMSO-d$_6$) δ;
2.77(br,s,4H), 3.28(br,s,2H), 3.50(m,1H), 5.88(s,2H), 6.69(m,3H),
MS (EI) m/z; 298(M$^+$), 280, 148(Base)

Example 22 (Compound 15)

R = —CH—COOH (preparation process D)
    |
   CH$_3$

NMR (90 MHz, D$_2$O) δ;
1.40(d,J=7 Hz,3H), 2.86(s,4H), 3.43(q,J=7Hz,1H), 5.93(s,2H), 6.80(m,3H)
MS(FAB) m/z; 299M$^+$+1)

Example 23 (Compound 16)

R = —CH$_2$CONH$_2$ (preparation process B)
m.p.: 93.5° to 94.5° C.
NMR (90 MHz, CDCl$_3$) δ;
2.78(s,4H), 3.18(s,2H), 5.6~6.9(br,s,2H), 5.86(s,2H), 6.61(m,3H)
MS (El) m/z; 229(M$^+$), 148(Base)

| Elementary analysis for $C_{11}H_{13}O_3NS$: | | | |
|---|---|---|---|
| | C | H | N | S |
| calculated (%) | 55.21 | 5.48 | 5.85 | 13.40 |
| found (%) | 55.38 | 5.42 | 5.82 | 13.34 |

Example 24 (Compound 18)

$$R = -CH_2-\overset{O}{\underset{\|}{C}}-N\overset{C_2H_5}{\underset{C_2H_5}{\diagdown}} \quad \text{(preparation process B)}$$

NMR (90 MHz, CDCl$_3$) δ;
1.17(q,J=7Hz,6H), 2.86(s,2H), 3.28(s, 2H), 3.37(q,J=7Hz,2H), 3.39(q,J=7Hz,2H), 5.92(s,2H), 6.72(m,3H)
MS (EI) m/z; 295(M$^+$), 148(Base)

Example 25 (Compound 19)

$$R = -CH_2CH_2-\overset{O}{\underset{\|}{C}}-N\overset{CH_3}{\underset{CH_3}{\diagdown}} \quad \text{(preparation process C)}$$

NMR (90 MHz, CDCl$_3$) δ;
2.44~2.85(m,4H), 2.75(s,4H), 2.92(s, 3H), 2.96(s,3H), 5.84(s,2H), 6.61(m,3H)
MS (EI) m/z; 281(M$^+$), 149(Base)

Example 26 (Compound 20)

$$R = -CH_2CH_2-N\overset{CH_3}{\underset{CH_3}{\diagdown}} \quad \text{(preparation process A)}$$

m.p.: 146° to 148° C.
NMR (90 MHz, CDCl$_3$) δ;
2.79(s,6H), 2.84(s,4H), 3.06(m,4H), 5.94(s,2H), 6.72(m,3H)
MS (EI) m/z;
253(M$^+$), 149, 135, 105, 91(Base)

Example 27 (Compound 24)

$$R = -(CH_2)_2-\overset{O}{\underset{\|}{C}}-N\overset{H}{\underset{CH_2COOH}{\diagdown}} \quad \text{(preparation process E)}$$

m.p.: 152° to 153° C.
NMR (90 MHz, CDCl$_3$-CD$_3$OD) δ;
2.53(m,2H), 2.73~2.92(m,6H), 3.94(s, 2H), 5.90(s,2H), 6.69(m,3H), 7.58(s,1H)
MS (EI) m/z; 311(M$^+$), 149(Base), 148

In the following Example 28, compounds of the following general formula (I″) wherein R was a group shown below were prepared.

These compounds were prepared in the same manner as that of Example 6.

$$\text{(I″)}$$

Example 28 (Compound 27)

R=—CH$_2$CH$_2$OH m.p 107° to 108° C.
NMR (90 MHz, CDCl$_3$) δ;
2.8~3.3(m,7H), 4.18(m,2H), 5.94(s,2H), 6.72(m,3H)
MS (FAB) m/z; 243M$^+$+1)

In the following Examples 29 to 32, compounds of the following general formula (I‴) wherein R was a group shown below were prepared.

These compounds were prepared in the same manner as that of Example 7.

$$\text{(I‴)}$$

Example 29 (Compounds 29)

R=CH$_2$CH$_2$OH m.p.: 78° to 80° C.
NMR (90 MHz, CDCl$_3$) δ;
2.37(t,J=6Hz,1H), 2.9~3.5(m,6H), 4.12(m,2H), 5.95(s,2H), 6.72(m,3H)
MS (EI) m/z; 258(M$^+$), 149, 119(Base)

Example 30 (Compound 30)

R=—CH$_2$COOH m.p.: 144.5° to 145° C.
NMR (90 MHz, DMSO-d$_6$-CDCl$_3$) δ;
3.04(m,2H), 3.52(m,2H), 4.07(s,2H), 5.3(br,1H), 5.95(s,2H), 6.86(m,3H)
MS (EI) m/z; 272(M$^+$), 148(Base)

Example 31 (Compound 31)

R=—CH$_2$CH$_2$COOH m.p.: 176.5° to 177.5° C.
NMR (90 MHz, DMSO-D$_6$) δ;
2.60~3.10(m,4H), 3.24~3.50(m,4H), 5.98(s,2H), 6.81(m,2H), 6.92(m,1H), 12.3(br,1H)
MS (EI) m/z; 286(M$^+$, Base)

Example 32 (Compound 32)

R=—(CH$_2$)$_3$COOH m.p.: 153.5° to 155.5° C.
NMR (90 MHz, DMSO-D$_6$) δ;
1.95(m,2H), 2.40(t,J=7Hz,2H), 2.80~3.46(m,6H), 5.96(s,2H), 6.80(m,1H), 6.91(m,1H), 12.5(br,1H)
MS (EI) m/z; 300(M$^+$), 149(Base), 148

Compound Group (I-c)

Example 1

3-(6-Propyl-1,3-benzodioxol-5-yl)propionic acid

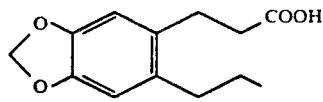

(1) Synthesis of 5-chloromethyl-6-propyl-1,3-benzodioxole

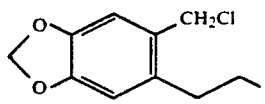

22 g of a 37 % aqueous formaldehyde solution and 20 ml of ethyl acetate were added to 10 ml of concentrated hydrochloric acid. The mixture was heated to 55° C. A solution of 10.9 g of 5-propyl-1,3-benzodioxole in 100 ml of ethyl acetate was added dropwise to the mixture while hydrogen chloride gas was introduced thereinto. The mixture was stirred for 2 h and 45 min. 300 m( of ethyl acetate and 300 ml of water were added thereto. The formed layers were separated. The ethyl acetate layer was washed with water three times and dried over anhydrous sodium sulfate. The solvent was distilled off to obtain 16.1 g of the crude intended compound in the form of a colorless oil.

.$^1$H-NMR(90MHZ, CDCl$_3$) δ:
0.99(t,J=7.2Hz,3H), 1.36~1.86(m,2H),
2.64(t,J=7.2Hz,2H), 4.57(s,2H), 5.95
(s,2H), 6.70(s,1H), 6.83(s,1H)

(2) Synthesis of diethyl (6-propyl-1,3-benzodioxole-5-yl)methylmalonate

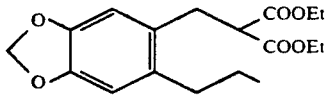

24.3 g of diethyl malonate, 42 g of potassium carbonate, 300 ml of acetone and a catalytic amount of tetrabutylammonium bromide were added to 16.1 g of crude 5-chloromethyl-6-propyl-1,3-benzodioxole and the mixture was heated under reflux for 25 h. The reaction mixture was filtered and the residue was washed with acetone. The washing was combined with the filtrate. The solvent was distilled off. 500 ml of ethyl acetate and 500 ml of water were added thereto and the layers thus formed were separated. The ethyl acetate layer was washed with water three times and dried over anhydrous sodium sulfate. The solvent was distilled off to obtain 16.5 g of the crude intended compound in the form of a colorless oil.

.$^1$H-NMR(90MHz,CDCl$_3$) δ;
0.96(t,J=7.2Hz,3H), 1.22(t,J=7.2Hz,
6H), 1.30~1.80(m,2H), 2.32~2.60(m,
2H), 3.10(d,J=7.2Hz,2H), 3.50(t,J=7.2
Hz,1H), 4.14(q,J=7.2Hz,4H), 5.83(s,
2H), 6.58(s,2H)

(3) Synthesis of (6-propyl-1,3-benzodioxole-5-yl)-methylmalonate

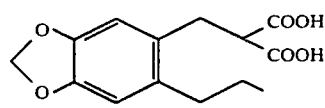

16.5 g of diethyl (6-propyl-1,3-benzodioxole-5-yl)methylmalonate was dissolved in 150 ml of ethanol. 20 g of sodium hydroxide and 50 m( of water were added to the solution and the mixture was heated on a boiling water bath for 30 min. The reaction mixture was concentrated. 300 ml of ethyl acetate and 300 ml of water were added thereto and the layers thus formed were separated. The aqueous layer was acidified with concentrated hydrochloric acid. After extraction with ethyl acetate, the ethyl acetate layer was washed with water three times and then dried over anhydrous sodium sulfate. The solvent was distilled off to obtain 15.2 g of the intended compound in the form of a white powder.

.$^1$H-NMR(90MHz.DMSO-d$_6$) δ;
0.91(t,J=7.2Hz,3H), 1.31~1.66(m,2H),
2.50(t,J=7.2Hz,2H), 2.98(d,J=7.2Hz,
2H), 3.47(t,J=7.2Hz,1H), 5.94(s,2H),
6.74(s,2H), 12.7(bs,2H)

(4) Synthesis of 3-(6-propyl-1,3-benzodioxole-5-yl)-propionic acid

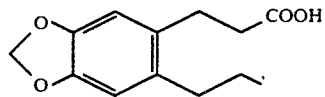

10 g of (6-propyl-1,3-benzodioxole-5-yl)methylmalonic acid was heated at 150° to 160° C. on an oil bath for 1 h. It was then purified according to silica gel column chromatography (chloroform/methanol =20:1) and recrystallized from isopropyl ether to obtain 6.9 g of the intended compound in the form of colorless crystals.

.$^1$H-NMR(90MHz,CDCl$_3$) δ;
0.95(t,J=7.0Hz,3H), 1.28~1.80(m,2H),
2.08~3.00(m,6H), 5.85(s,2H), 6.58(s, 2H)

Example 2

Sodium 3-(6-propyl-1,3-benzodioxole-5-yl)propionate

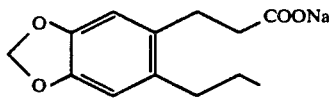

29.2 ml of a 1N aqueous sodium hydroxide solution and 100 ml of ethanol were added to 6.9 g of 3-(6-propyl-1,3-benzodioxole-5-yl)propionic acid to obtain a solution. The solvent was distilled off and ether was added to the residue. A precipitate thus formed was recovered by filtration and dried to obtain 7.5 g of the intended compound in the form of a colorless powder.

° m.p. (° C.); 213~216

.$^1$H-NMR(90MHz,CDCl$_6$) δ; 0.90(t,J=7.4Hz,3H),
1.20~2.71(m,2H), 1.92~2.22(m,2H),
2.26~2.80(m,4H),
5.82(s,2H), 6.57(s,1H), 6.64(s,1H)

.MS(FAB)m/z;281(MNa−), 259(MH−)

Example 3

3-(6-Ethyl-1,3-benzodioxole-5-yl)propionic acid

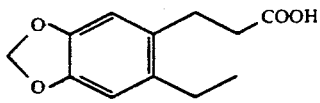

1.42 g of the intended compound in the form of colorless crystals was obtained from 5.4 g of 5-ethyl-1,3-benzodioxole in the same manner as that of Example 1.

.$^1$H-NMR(90MHz,CDCl$_3$) δ;
1.20(t,J=7Hz,3H), 2.32∼3.08(m,6H),
5.84(s,2H), 6.60(s,1H), 6.64(s,1H)

Example 4

Sodium 3-(6-ethyl-1,3benzodioxole-5-yl)propionate

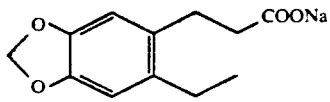

1.53 g of the intended compound in the form of colorless crystals was obtained from 1.42 g of 3-(6-ethyl-1,3-benzodioxole-5-yl)propionic acid in the same manner as that of Example 2.

° m.p (° C.); 202∼204 (dec.)
.$^1$H-NMR(400MHz,DMSO-d$_6$) δ;
1.10(t,J=7Hz,3H), 2.06(t,J=8Hz,2H),
2.51(q,J=7Hz,2H), 2.66(t,J=8Hz,2H),
5.88(s,2H), 6.68(s,1H), 6.71(s,1H)
.MS(FAB)m/z;245(MH−)

EXAMPLE 5

3-(6-Methyl-1,3-benzodioxole-5-yl)propionic acid

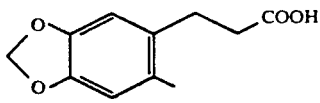

80 g of the intended compound in the form of colorless crystals was obtained from 150 g of 5-methyl-1,3-benzodioxole in the same manner as that of Example 1.

° m.p. (° C.); 129∼132
.$^1$H-NMR(90MHz,CDCl$_3$) δ;
2.20(s,3H), 2.36∼2.98(m,4H), 5.81(s,
2H), 6.56(s,2H), 11.24(bs,1H)

Example 6

Sodium 3-(6-methyl-1,3-benzodioxole-5-yl)propionate

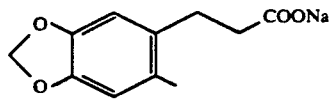

0.59 g of the intended compound in the form of a white powder was obtained from 0.54 g of 3-(6-methyl-1,3-benzodioxole-5-yl)propionic acid in the same manner as that of Example 2.

° m.p. (° C.); 209∼212
.$^1$H-NMR(90MHz,CDCl$_6$) δ;
2.54(s,3H), b 1.86∼2.84(m,4H), 5.80(s,
2H), 6.56(s,1H), 6.63(s,1H)
.MS(FAB)m/z;253(MNa−), 231(MH−)

Example 7

3-(6-Methoxymethyl-1,3-benzodioxole-5-yl)propionic acid

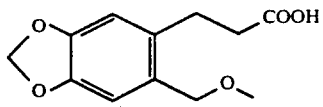

1.6 g of 3-(6-acetoxymethyl-1,3-benzodioxole-5-yl)propionic acid was dissolved in 100 ml of methanol. A catalytic amount of p-toluenesulfonic acid was added to the solution and the mixture was heated under reflux for 4 h and 15 min. The solvent was distilled off from the reaction mixture. A solution of 1 g of sodium hydroxide in the mixture of 5 ml of water and 45 ml of ethanol was added to the residue and the mixture was heated under reflux for 20 min. The reaction mixture was concentrated. 200 ml of ethyl acetate and 200 ml of water were added to the concentrate. The mixture was acidified with concentrated hydrochloric acid. The layers thus formed were separated. The product was washed with water three times and then dried over anhydrous sodium sulfate. The solvent was distilled off to obtain 1.25 g of the intended compound in the form of a white powder.

.$^1$H-NMR(90MHz,CDCl$_3$) δ;
2.24∼3.10(m,4H), 3.34(s,3H), 4.33(s,
2H), 5.86(s,2H), 6.64(s,1H), 6.74(s,1H)

Example 8

Sodium 3-(6-methoxymethyl-1,3-benzodioxole-5-yl)-propionate

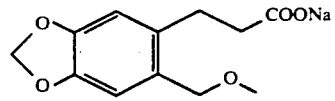

1.3 g of the intended compound in the form of a white powder was obtained from 1.25 g of 3-(6-methoxymethyl-1,3-benzodioxole-5-yl)propionic acid in the same manner as that of Example 2.

° m.p. (° C.); 155∼159
.$^1$H-NMR(90MHz,CDCl$_6$) δ;
1.88∼2.90(m,4H), 3.23(s,3H), 4.28(s,
2H), 5.87(s,2H), 6.71(s,1H), 6.74(s,1H)
.MS(FAB)m/z;283(MNa−), 261(MH−)

Example 9

3-(6-Ethoxymethyl-1,3-benzodioxole-5-yl)propionic acid

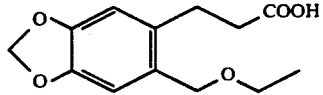

0.6 g of metallic sodium was dissolved in 100 ml of ethanol. 2.0 g of 3-(6-chloromethyl-1,3-benzodioxole-5-yl)propionic acid was added in small portions to the solution. The mixture was heated at 50° C. for 2 h. The solvent was distilled off and the residue was acidified with 1N hydrochloric acid. After extraction with chloroform, the organic layer was dried over magnesium sulfate. The solvent was distilled off. After separation according to silica gel column chromatography (chloroform), 0.73 g of the intended compound in the form of colorless crystals was obtained.

° m.p. (° C.); 97~98
.¹H-NMR(90MHz,CDCl₃) δ;
1.23(t,J=7Hz,3H), 2.61(m,2H), 2.91(m, 2H), 3.51 (q.J=7Hz,2H), 4.38(s,2H), 5.87(s,2H), 6.64(s,1H), 6.76(s,1H)

Example 10

Sodium 3-(6-ethoxymethyl-1,3-benzodioxole-5-yl)propionate

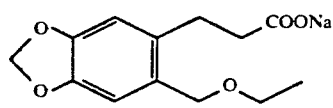

0.7 g of the intended compound in the form of colorless crystals was obtained from 0.71 g of 3-(6-ethoxymethyl-1,3-benzodioxole-5-yl)propionic acid in the same manner as that of Example 2.

° m.p. (° C.); 165~182 (dec.)
.¹H-NMR(400DMSO-d₆) δ;
1.13(t,J=7.0Hz,3H), 2.07(m,2H), 2.68(m, 2H), 3.45(q.J=7.0Hz,2H). 4.36(s,2H), 5.92(s,2H), 6.78(s,1H), 6.81(s,1H)
.MS(FAB)m/z;297(MNa⁻), 275(MH⁻)

Example 11

(5,6-Methylenedioxyindane-2-yl)carboxylic acid

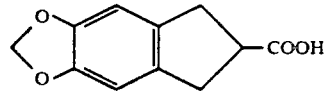

(1) Synthesis of 5,6-methylenedioxyindene

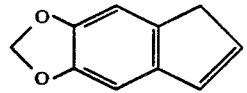

A solution of 10.8 g of 1-hydroxy-5,6-methylenedioxyindane and 15 ml of acetic acid in 100 ml of toluene was heated under reflux for 4 h. Water and a small amount of potassium carbonate were added to the reaction mixture. After extraction with ethyl acetate, the organic layer was washed with water and an aqueous common salt solution and dried over magnesium sulfate. The solvent was distilled off and the residue was treated according to silica gel column chromatography (chloroform/hexane=1:3) to obtain 9.0 g of the intended compound in the form of colorless crystals.

° m.p. (° C.); 85~86
.¹H-NMR(90MHz,CDCl₃) δ;
3.29(m,2H), 5.92(s,2H), 6.43(dt,J=2 Hz and 6Hz,1H), 6.74(m,1H), 6.86(s,1H) 6.95(s,1H)

(2) Synthesis of 5,6-methylenedioxyindane-2-ol

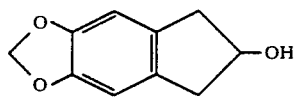

A solution of 9.0 g of 5,6-methylenedioxyindene in 23 ml of tetrahydrofuran was cooled to 0° C. in a nitrogen atmosphere. A solution of 2.2 ml of 10.0 M borane/-methyl sulfide complex in 5 ml of tetrahydrofuran was added dropwise thereto. The temperature of the mixture was elevated from 0° C. to room temperature over 4 h and then 1.8 ml of water was added dropwise thereto. 7.4 ml of a 3 M aqueous sodium hydroxide solution and then 5.5 ml of a 35% aqueous hydrogen peroxide solution were added thereto under cooling with ice and the mixture was stirred at room temperature overnight. The reaction mixture was diluted with ethyl acetate, washed with an aqueous common salt solution and dried over magnesium sulfate. The solvent was distilled off and the residue was crystallized from ethyl acetate to obtain 6.4 g of the intended compound in the form of white crystals.

° m.p. (° C.); 99~100
.¹H-NMR(90MHz,CDCl₃) δ;
1.73(m,1H), 2.79(dd,J=4Hz and 16Hz, 2H), 3.14(dd,J=6Hz and 16Hz.2H), 4.68 (m,1H), 5.91(s,2H), 6.71(s,2H)

(3) Synthesis of 2-cyano-5,6-methylenedioxyindane

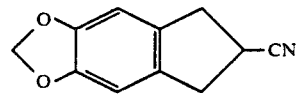

7.45 g of methanesulfonyl chloride was added dropwise to a solution of 5.8 g of 5,6-methylenedioxyindane-2-ol and 9.1 ml of triethylamine in 150 ml of dichloromethane under cooling with ice. The mixture was stirred at 0° C. for 1 h. A mixture of ice and water was added to the reaction mixture and the resulting mixture was washed with a saturated aqueous sodium hydrogencarbonate solution and dried over magnesium sulfate. The solvent was distilled off to obtain 8.0 g of a methanesulfonate, which was subjected to the subsequent reaction without purification.

A mixture of 2.6 g of the methanesulfonate, 1.0 g of sodium cyanide and a solution of a catalytic amount of sodium iodide in 20 ml of dimethylformamide was heated at 80° C. for 6 h. Water was added to the reaction mixture. After extraction with ether, the aqueous layer was washed with water and an aqueous common salt solution and dried over magnesium sulfate. The solvent was distilled off and the residue was separated according to silica gel column chromatography to obtain 0.4 g of the intended compound in the form of colorless crystals.

° m.p. (° C.); 124~125
.¹H-NMR(90MHz,CDCl₃) δ;
3.19(m,5H), 5.87(s,2H), 6.60(s,2H)

(4) Synthesis of (5,6-methylenedioxyindane-2-yl)-carboxylic acid

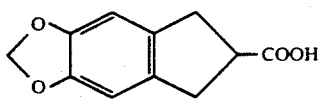

3.9 ml of a 35% aqueous hydrogen peroxide solution was added dropwise to a mixture of 1.4 g of 2-cyano-5,6-methylenedioxyindane, 50 ml of a 30% aqueous potassium hydroxide solution and 50 ml of ethanol. Then the mixture was heated at 60° C. for 2 h and the solvent wad distilled off. Dilute hydrochloric acid was added to the residue. After extraction with chloroform, the organic layer was dried over magnesium sulfate. The solvent was distilled off and the residue was recrystallized from diisopropyl ether to obtain 1.4 g of the intended compound in the form of colorless crystals.

° m.p. (° C.); 168~169
.$^1$H-NMR(90MHz,CDCl$_3$) δ;
3.00~3.44(m,5H), 5.85(s,2H), 6.60(s, 2H), 10.0(bs,1H)

Example 12

Sodium (5,6-methylenedioxyindane-2-yl)carboxylate

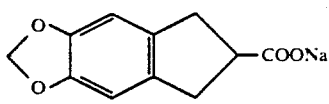

1.5 g of the intended compound in the form of colorless crystals was obtained from 1.4 g of (5,6-methylenedioxyindane-2-yl)carboxylic acid in the same manner as that of Example 2.

° m.p. (° C.); >270
.$^1$H-NMR(400MHz,DMSO-d$_6$) δ;
2.77~3.04(m,5H), 5.89(m,2H), 6.68(s, 2H)
.MS(FAB)m/z;251(MNa−), 229(MH−)

Example 13

(7,8-Dihydro-5H-1,3-dioxolo[4,5-g][2]benzopyran-5-yl)acetic acid

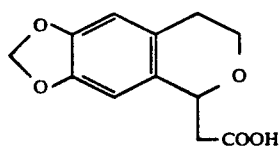

(1) Synthesis of ethyl(7,8-dihydro-5H-1,3-dioxolo-[4,5-g][2]benzopyran-5-yl)acetate

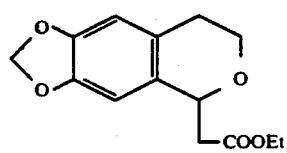

1.3 g of ethyl 3-{6-(2-hydroxyethyl)-1,3-benzodioxol-5-yl}acrylate was dissolved in 30 ml of ethanol. A catalytic amount of sodium ethylate was added to the solution and the mixture was heated under reflux for 2 h. The solvent was distilled off and 1N hydrochloric acid and water were added to the residue. After extraction with ethyl acetate followed by washing with a saturated aqueous common salt solution and drying over anhydrous magnesium sulfate, the solvent was distilled off. The residue was purified according to silica gel column chromatography (hexane/ethyl acetate=85:15) to obtain 0.78 g of the intended compound in the form of a colorless oil.

.$^1$H-NMR(90MHz,CDCl$_3$) δ;
1.27(t,J=7.2Hz,3H), 2.35~3.1(m,4H),
3.5~4.37(m,2H), 4.17(q,J=7.2Hz,2H),
5.09(dd,J=7.2Hz and J=5.6Hz,1H), 5.85 (s,2H), 6.46(s,1H), 6.51(s,1H)

(2) Synthesis of (7,8-dihydro-5H-1,3-dioxolo[4,5-g]-[2]benzopyran-5-yl)acetic acid

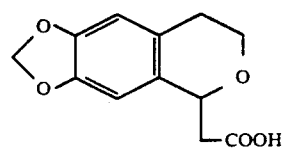

0.78 g of ethyl (7,8-dihydro-5H-1,3-dioxolo[4,5-g]-[2]benzopyran-5-yl)acetate was dissolved in 20 ml of ethanol. A solution of 0.35 g of sodium hydroxide in 4 ml of water was added thereto and the mixture was stirred under heating at 60° C. The solvent was distilled off and water was added to the residue. The mixture was washed with ethyl acetate and acidified with 1N hydrochloric acid. After extraction with chloroform, the extract was washed with a saturated aqueous common salt solution an dried over anhydrous magnesium sulfate. After filtration, the solvent was distilled off and the residue was subjected to silica gel column chromatography (chloroform) to obtain 0.67 g of the intended compound in the form of colorless crystals.

.$^1$H-NMR(90MHz,CDCl$_3$) δ;
2.35~3.20(m,4H), 3.5~3.95(m,1H),
3.92~4.28(m,1H), 4.95~5.25(m,1H),
5.87(s,2H), 6.46(s,1H), 6.52(s,1H), 7.2~8.6(br,1H)

Example 14

Sodium (7,8-dihydro-5H-1,3-dioxolo[b 4,5-g][2]benzopyran-5-yl)acetate

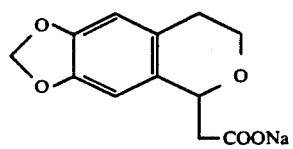

0.69 g of the intended compound in the form of colorless crystals was obtained from 0.66 g of (7,8-dihydro-5H-1,3-dioxolo[4,5-g][2]benzopyran-5-yl)-acetic acid in the same manner as that of Example 2.

° m.p. (° C.); 257.5~258 (dec.)
.$^1$H-NMR(90MHz,DMSO-d$_6$) δ;
2.26(d,J=6.5Hz,2H), 2.3~2.55(m,2H),
3.35~4.05(m,2H), 4.89(t,J=6.5Hz,1H),
5.83(s,1H), 6.52(s,1H), 6.75(s,1H)
.MS(FAB)m/z;281(MNa−), 259(MH−)

Compound Group (I-d)

Preparative Example 1

2-(1,3-Benzodioxol-5-yl)ethanethiol

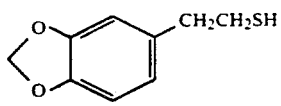

750 g of 5-(2-bromoethyl)-1,3-benzodioxole was dissolved in 1 l of ethanol. 312 g of thiourea was added to the solution and the mixture was heated under reflux on a boiling water bath for 2 h. The reaction mixture was cooled and a solution of 300 g of sodium hydroxide in 1 l of water was added thereto. The resulting mixture was heated under reflux on a boiling water bath for 45 min. After cooling. 3 l of water was added thereto. After extraction with 5 l of ethyl acetate, the extract was washed with dilute hydrochloric acid and then with water until the washing became almost neutral. After drying over anhydrous sodium sulfate followed by distillation of the solvent at 40° C., about 570 g of a faint yellow oil was obtained. This product was purified according to column chromatography (hexane/benzene=2:1) with about 3 kg of silica gel to obtain 310 g of the intended compound in the form of a colorless oil.

$^1$H-NMR (90MHz, CDCl$_3$) δ;1.36 (m,1H) 2.6 ~2.19 (m,4H). 5.87 (s,2H). 6.50~ 6.74 (m,3H)

Preparative Example 2

3-Acetoxy-4-(2-hydroxyethyl)-5-methylisoxazole

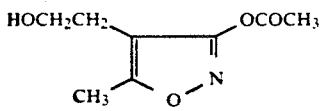

7.8 g of 4-(2-hydroxyethyl)-5-methylisoxazol-3-ol was dissolved in 1 l of tetrahydrofuran. 1.70 g of sodium hydride was added to the solution under cooling with ice. The mixture was stirred at room temperature for 30 min and then cooled again with ice. 4.7 g of acetyl chloride was added thereto and the mixture was stirred at room temperature. The solvent was distilled off and water was added to the residue. After extraction with chloroform, the extract was washed with a saturated aqueous common salt solution and dried over anhydrous magnesium sulfate. After filtration, the solvent was distilled off and the residue was purified according to silica gel column chromatography (chloroform) to obtain 2.96 g of the intended compound in the form of colorless prismatic crystals.

$^1$H-NMR(90MHz,CDCl$_3$) δ;2.30 (s,3H)
2.49 (t,J=6.1Hz,2H), 2.56 (s,3H),
3.76 (t,J=6.1Hz,2H)

Preparative Example 3

5-(2-Hydroxyethyl)-2-methyl-1,3-benzodioxole

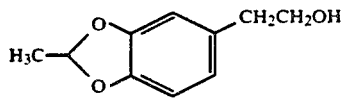

A suspension of 1.0 g of 3,4-dihydroxyphenylacetic acid, 1.4 g of vinyl acetate. 6 mg of mercury oxide (yellow) and 0.03 ml of boron fluoride/ethyl etherate in 9 ml of toluene was stirred at room temperature for 14 h. The reaction mixture was diluted with ethyl acetate and washed with water and an aqueous common salt solution The organic layer was dried over magnesium sulfate and the solvent was distilled off. An oil thus obtained was dissolved in 10 ml of tetrahydrofuran and the solution was added dropwise to a suspension of 0.5 g of lithium aluminum hydride in tetrahydrofuran under cooling with ice. The mixture was stirred at room temperature for 1 h. 0.5 ml of water, then 0.5 ml of a 15% aqueous sodium hydroxide solution and finally 1.5 ml of water were added thereto and an insoluble matter was filtered off. The filtrate was concentrated and treated according to silica gel column chromatography (ethyl acetate/hexane=1:1) to obtain 0.8 g of the intended compound in the form of a colorless oil.

.$^1$H-NMR(90MHz,CDCl$_3$) δ;1.66 (d,J=5Hz,b 3H),
1.74 (m,1H). 2.73 (t,J=6Hz,2H),
3.72 (m,2H), 6.14 (q,J=5Hz,1H),
6.59 (s,3H)

Preparative Example 4

2,2-Dimethyl-5-(2-hydroxyethyl)-1,3-benzodioxole

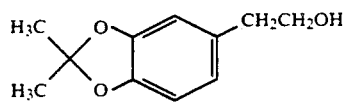

1.7 g of 3,4-dihydroxyphenylacetic acid, a catalytic amount of p-toluenesulfonic acid, 10 ml of acetone and 10 ml of benzene were heated under reflux for 18 h. The reflux solution was dehydrated with Molecular Sieve 4A. The reaction mixture was concentrated and the obtained dark brown oil was dissolved in 20 ml of tetrahydrofuran. The solution was added to a suspension of 0.8 g of lithium aluminum hydride in 30 ml of tetrahydrofuran under cooling with ice. The mixture was stirred at room temperature for 1 h and then cooled with ice/water. 0.8 ml of water, then 0.8 ml of a 15% aqueous sodium hydroxide solution and finally 2.4 ml of water were added thereto and an insoluble substance was filtered off. The filtrate was concentrated and treated according to silica gel column chromatography (ethyl acetate/ n-hexane=1:1) to obtain 1.1 g of the intended compound in the form of a colorless oil.

.$^1$H-NMR(90MHz,CDCl$_3$) δ;1.67 (s,6H),
1.7 (m,1H), 2.73 (t,J=6Hz,2H), 3.75 (bt,J=6Hz,2H),
6.56 (m,3H)

Preparative Example 5

2-(6-Methyl-1,3-benzodioxol-5-yl)ethanol

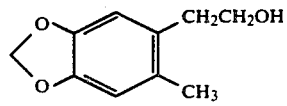

(a) 5-(2-Benzyloxyethyl)-6-bromo-1,3-benzodioxole

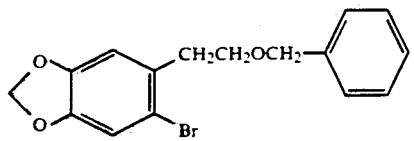

15.0 g of 5-(2-acetoxyethyl)-1,3-benzodioxole was dissolved in 10 ml of carbon tetrachloride. 4.6 g of bromine was added to the solution under cooling with ice. The temperature was elevated to room temperature and the reaction was conducted for 2 h. An aqueous sodium hydrogencarbonate solution was added thereto. After extraction with chloroform, the extract was washed with an aqueous sodium sulfate solution and dried over magnesium sulfate. After concentration under reduced pressure, a crude bromine compound was obtained in the form of brown needles.

This product (non-purified) was added to a solution of 8.6 g of sodium hydroxide in methanol and the reaction was conducted at 60° C. for 1.5 h. Methanol was removed and water was added to the residue. After extraction with ethyl acetate, the extract was washed with water, dried over magnesium sulfate and concentrated under reduced pressure to obtain a yellow oily residue.

This residue (non-purified) was added to a solution of 3.8 g of sodium hydride in 150 ml of dimethylformamide. The mixture was stirred at 60° C. for 30 min and the reaction mixture was cooled to room temperature. 13.7 g of benzyl chloride was added dropwise thereto and the reaction was conducted at 60° C. again for 1 h. The reaction mixture was poured into ice/water. After extraction with ethyl acetate, the extract was dried over magnesium sulfate and concentrated under reduced pressure to obtain crude benzyl ether. After purification according to silica gel column chromatography (ethyl acetate/ hexane=3:97), 12.0 g of the intended compound was obtained in the form of a faint yellow oil.

$^1$H-NMR(90MHz,CDCl$_3$) δ;2.98 (t,J=7Hz, 2H), 3.66 (t,J=7Hz,2H), 4.54 (s,2H), 5.95 (s,2H), 6.82 (s,1H), 7.02 (s,1H), 7.34 (s,5H)

(b) 5-(2-Benzyloxyethyl)-6-methyl-1,3-benzodioxole

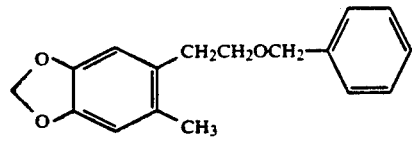

3.0 g of 5-(2-benzyloxyethyl)-6-bromo-1,3-benzodioxole was dissolved in 100 m( of anhydrous ether. 8.5 ml of a 1.6 M solution of n-butyllithium in hexane was added to the solution at −78° C. and the reaction was conducted at −50° C. for 2 h. The reaction mixture was cooled again to −78° C. 6.4 g of methyl iodide was added thereto and the temperature was gradually elevated to room temperature. Methanol and water were added to the reaction mixture. After extraction with ethyl acetate, the extract was dried over magnesium sulfate and concentrated under reduced pressure to obtain a crude methyl compound. After purification according to silica gel column chromatography (ethyl acetate/ hexane=2:98). 1.9 g of the intended compound was obtained in the form of a pale yellow oil.

$^1$H-NMR(90MHz,CDCl$_3$) δ:2.20 (s,3H), 2.82 (t,J=7Hz,2H), 3.58 (t,J=7Hz, 2H), 4.48 (s,2H), 5.82 (s,2H), 6.56 (s,1H), 6.60 (s,1H), 7.44 s,5H)

2-(6-Methyl-1,3-benzodioxol-5-yl)ethanol

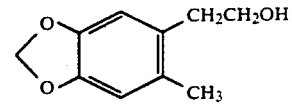

1.9 g of 5-(2-benzyloxyethyl)-6-methyl-1,3-benzodioxole was dissolved in 80 ml of ethanol. 0.2 g of 10% palladium/carbon (containing 50% water) and 4 ml of acetic acid were added thereto and the catalytic reduction was conducted under 3 atm/cm$^2$ for 1 h. After removing palladium/carbon, ethanol was distilled off and the product was purified according to silica gel column chromatography (ethyl acetate/hexane=2:3) to obtain 1.0 g of the intended compound in the form of a faint yellow oil.

$^1$H-NMR(90MHz,CDCl$_3$) δ;1.88 (bs,1H), 2.32 (s,3H), 2.88 (t,J=7Hz,2H), 3.88 (t,J=7Hz,2H), 5.96 (s,2H), 6.76 (bs,2H)

Preparative Example 6

2-(6-Ethyl-1,3-benzodioxol-5-yl)ethanol

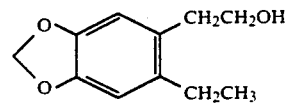

(a) (6-Ethyl-1,3-benzodioxol-5-yl)acetic acid

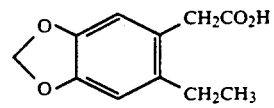

Gaseous hydrogen chloride was introduced into a mixture of 500 ml of concentrated hydrochloric acid, 1 l of ethyl acetate and 900 ml of an aqueous formaldehyde solution. A solution of 600 g of 5-ethyl-1,3-benzodioxole in 300 ml of ethyl acetate was added dropwise thereto at 55° C. and the reaction was conducted for 1 h. Benzene was added thereto and the product was washed with water, dried over magnesium sulfate and concentrated under reduced pressure to obtain a crude chlorine compound in the form of a faint yellow oil.

The crude chlorine compound was dissolved in 4 l of dimethyl sulfoxide. 400 g of thoroughly triturated sodium cyanide was added to the solution at room temperature and the mixture was stirred for 12 h. Water was added thereto. After extraction with ethyl acetate, the extract was washed with water, dried over magnesium sulfate and concentrated under reduced pressure to obtain a crude cyano compound in the form of a brown oil.

A solution of the crude cyano compound prepared as above in 2 l of ethanol was added to a solution of 800 g of sodium hydroxide and the mixture was heated under reflux for 16 h. Ethanol was distilled off from the reaction mixture and water was added to the residue. After washing with ether, the aqueous layer was acidified. After extraction with chloroform, the extract was washed with water, dried over magnesium sulfate and concentrated under reduced pressure.

The solid residue was recrystallized from ethyl acetate to obtain 400 g of the intended compound in the form of colorless crystals.

mp.; 114°~115° C.
$^1$H-NMR (90MHz, CDCl$_3$)δ; 1.16 (t,J=7Hz, 3H), 2.52 (q,J=7Hz,2H), 3.54 (s,2H), 5.84 (s,2H), 6.62 (s,2H)

(b) 2-(6-Ethyl-1,3-benzodioxol-5-yl)ethanol

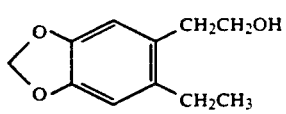

62 g of lithium aluminum hydride was suspended in 1.5 l of anhydrous tetrahydrofuran. A solution of 200 g of (6-ethyl-1,3-benzodioxol-5-yl)acetic acid in 200 ml of tetrahydrofuran was added dropwise to the suspension and the reaction was conducted at room temperature for 12 h. After the completion of the reaction, water was added thereto and the precipitate was filtered off. The filtrate was concentrated under reduced pressure and water was added to the residue. After extraction with ethyl acetate, the extract was washed with water, dried over magnesium sulfate, concentrated under reduced pressure and purified according to silica gel column chromatography (ethyl acetate/hexane=1:4) to obtain 169 g of the intended compound in the form of a faint yellow oil.

.$^1$H-NMR(90MHz,CDCl$_3$) δ;1.16 (t,J=7Hz, 3H), 2.80 (bs,1H), 2.54 (a,J=7Hz, 2H), 2.78 (t,J=7Hz,2H), 3.74 (t, J=7Hz,2H), 5.84 (s,2H), 6.60 (s, 1H), 6.62 (s,1H)

Preparative Example 7

2-(6-Propyl-1,3-benzodioxol-5-yl)ethanol

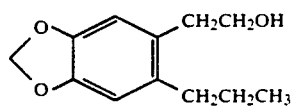

(a) (6-Propyl-1,3-benzodioxol-5-yl)acetonitrile

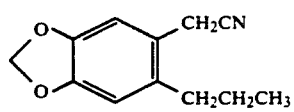

15 g of piperonyl butoxide and 300 ml of concentrated hydrochloric acid were dissolved in 100 ml of benzene and the solution was heated under reflux for 3 h. The reaction mixture was cooled to room temperature and water was added thereto. After extraction with ethyl acetate, the extract was washed with water, dried over magnesium sulfate and concentrated under reduced pressure to obtain 12 g of 6-propyl-5-chloromethyl-1,3-benzodioxole in the form of a faint brown oil.

2.0 g of the product was dissolved in 30 ml of dimethyl sulfoxide. 1.5 g of thoroughly triturated sodium canide was added to the solution and the reaction was conducted at room temperature for 2 h. The reaction mixture was poured into water. After extraction with ethyl acetate, the extract was washed with water, dried over magnesium sulfate, concentrated under reduced pressure and purified according to silica gel column chromatography (ethyl acetate/hexane=7:93) to obtain 1.7 g of the intended compound in the form of colorless needles.

mp.; 66°~67° C.
$^1$H-NMR (90MHz, CDCl$_3$) δ;0.98 (t,J=7Hz, 3H), 1.60 (sext,J=7Hz,2H), 2.52 (t,J=7Hz,2H), 3.64 (s,2H), 5.96 (s,2H), 6.72 (s,1H), 6.84 (s,1H)

(b) 2-(6-Propyl-1,3-benzodioxol-5-yl)ethanol

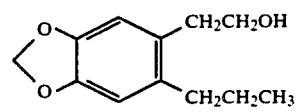

1.7 g of (6-propyl-1,3-benzodioxol-5-yl)-acetonitrile was added to a solution of 1.7 g of potassium hydroxide in 40 ml of 50% hydrous ethanol. The mixture was heated under reflux for 14 h. Ethanol was distilled off from the reaction mixture under reduced pressure and water was added to the residue. After washing with ether, the aqueous layer was acidified. After extraction with chloroform, the extract was washed with water, dried over magnesium sulfate and concentrated under reduced pressure to obtain 2-(6-propyl-1,3-benzodioxol-5-yl)acetic acid.

This product was added to a solution of 0.64 g of lithium aluminum hydride in 20 ml of tetrahydrofuran at 0° C. and the reaction was conducted for 1 h. Water was added to the reaction mixture and a precipitate thus formed was filtered off. The filtrate was concentrated and purified according to silica gel column chromatography (ethyl acetate/hexane=3:7) to obtain 1.4 g of the intended compound in the form of a colorless oil.

$^1$H-NMR (90MHz, CDCl$_3$)δ; 0.96 (t,J=7Hz, 3H), 1.56 (sext,J=7Hz,2H), 2.52 (t,J=7Hz,2H), 2.80 (t,J=7Hz,2H), 3.78 (t,J=7Hz,2H), 5.89 (s,2H) 6.68 (s,2H)

Preparative Example 8

1-(1,3-Benzodioxol-5-yl)-2-methyl-1-propene

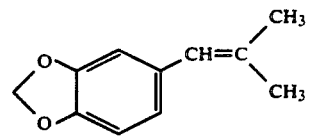

62.5 ml of a 1.6 M solution of butyllithium in hexane was added to 500 ml of anhydrous ether. 38.5 g of isopropyltriphenylphosphonium bromide was added thereto in a nitrogen gas stream and the mixture was stirred for 4 h. 18 g of piperonal was added to the reaction mixture and the resulting mixture was stirred for 5.5 h and then filtered. The filtrate was washed with 1 l of ether, concentrated under reduced pressure and purified according to silica gel column chromatography (hexane/ethyl acetate=10:1) to obtain 13.1 g of the intended compound in the form of a colorless oil.

$^1$H-NMR (90MHz, CDCl$_3$) δ;1.83 (d,J=1Hz,3H), 1.86 (d,J=1Hz,3H), 5.92 (s,2H), 6.15 (m,1H), 6.56~6.82 (m,3H)

Preparative Example 9

2-[{2-(1,3-Benzodioxol-5-yl)ethyl}thio]ethanesulfonyl chloride

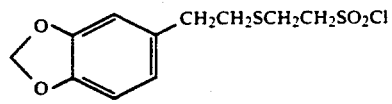

(a) Sodium 2-[{2-(1,3-benzodioxol-5-yl)ethyl}thio]-ethanesulfonate

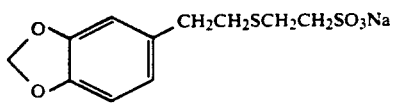

15 g of 2-(1,3-benzodioxol-5-yl)ethanethiol and 17.4 g of sodium 2-bromoethanesulfonate were dissolved in a mixture of 280 ml of ethanol and 120 ml of water. 3.3 g of sodium hydroxide was added to the solution and the mixture was heated under reflux for 1 h. The reaction mixture was concentrated and 500 ml of ethyl acetate and 500 ml of water were added thereto. After separation of the layers, the aqueous layer was acidified with hydrochloric acid. After extraction with n-butanol, the extract was washed with a saturated aqueous common salt solution. The solvent was distilled off to obtain 19 g of a faint yellow residue. This product was dissolved in a solution of 2.94 g of sodium hydroxide in dilute methanol and recrystallized therefrom to obtain 14.7 g of the intended compound in the form of colorless crystals.

$^1$H-NMR (90MHz, DMSO-d$_6$) δ;2.72 (s,8H), 5.94 (s,2H), 6.56~6.88 (m,3H)

(b) 2-[{2-(1,3-Benzodioxol-5-yl)ethyl}thio]-ethanesulfonyl chloride

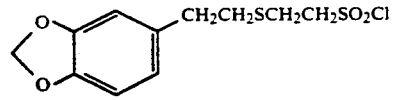

1.9 g of sodium 2-[{2-(1,3-benzodioxol-5-yl)-2-ethyl}thio]ethanesulfonate was suspended in 4 ml of N,N-dimethylformamide. 0.89 g of thionyl chloride was added dropwise to the suspension under cooling with ice/water. The mixture was stirred under cooling with water for 20 min. After adding ice/water and then a mixture of 200 ml of chloroform and 200 ml of water to the reaction mixture, the layers thus formed were separated. The chloroform layer was washed with water and dried over anhydrous sodium sulfate. The solvent was distilled off to obtain 2.1 g of the intended compound in the form of a colorless oil.

$^1$H-NMR (90MHz, CDCl$_3$) δ; 2.83 (s,4H), 2.92~3.15 (m,2H), 3.65~3.94 (m,2H), 5.94 (s,2H), 6.56~6.85 (m,3H)

Example 1

[{2-(1,3-Benzodioxol-5-yl)ethyl}thio]propan-2-one

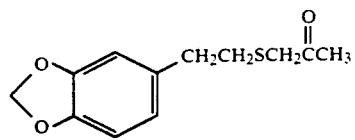

10 g of 2-(1,3-benzodioxol-5-yl)ethanethiol and 5.1 g of 1-chloro-2-propanone were dissolved in 200 ml of 90% ethanol. 2.2 g of sodium hydroxide was added to the solution and the mixture was heated under reflux for 10 min to conduct the reaction. The reaction mixture was concentrated under reduced pressure. 200 ml of ethyl acetate was added thereto to obtain a solution, which was washed with water three times. After drying over anhydrous sodium sulfate, the solvent was distilled off and the residue was purified according to silica gel column chromatography (benzene/ethyl acetate=30:1) to obtain 11.1 g of the intended compound in the form of a colorless oil.

$^1$H-NMR (90MHz, CDCl$_3$) δ;2.25 (s,3H), 2.50~2.90 (m,4H), 3.17 (s,2H), 5.85 (s,2H), 6.40~6.75 (m,3H)
MS m/z; 238 (M$^-$), 149

Example 2

[{2-(1,3-Benzodioxol-5-yl)ethyl}thio]acetonitrile

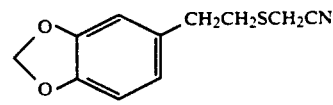

8.5 g of the intended compound in the form of a colorless oil was obtained from 4.2 g of 2-(1,3-benzodioxol-5-yl)ethanethiol and 4.2 g of chloroacetonitrile in the same manner as that of Example 1.

$^1$H-NMR (90MHz, CDCl$_3$) δ;2.76~3.03 (m,4H), 3.22 (s,2H), 5.91 (s,2H), 6.56~6.82 (m,3H)
MS m/z; 221 (M$^-$), 135

Example 3

2-Methyl-2-[{2-(1,3-benzodioxol-5-yl)ethyl}thio]-propionic acid

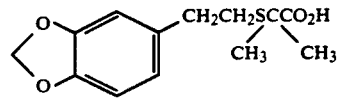

6 g of the intended compound in the form of a colorless oil was obtained from 6 g of 2-(1,3-benzodioxol-5-yl)ethanethiol and 4.6 g of 2-bromo-2-methylpropionic acid in the same manner as that of Example 1.

$^1$H-NMR (90MHz, CDCl$_3$) δ; 1.53 (s,6H), 2,70~2.90 (m,4H), 5.90 (s,2H), 6.52~6.80 (m,3H)

Example 4

Sodium 2-methyl-2-[{2-(1,3-benzodioxol-5-yl)ethyl}-thio]propionate

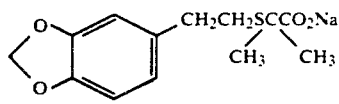

A solution of 0.90 g of sodium hydroxide in 9.0 ml of water was added to 6 g of 2-methyl-2-[{2-(1,3-benzodioxol-5-yl)ethyl}thio3propionic acid to obtain a solution. 100 ml of ethanol was added to the solution and the solvent was distilled off. The residue was washed with ether. After filtration, the product was dried under reduced pressure to obtain 6 g of the intended compound in the form of a white powder.

mp. ;261°~265° C.
$^1$H-NMR (90MHz, DMSO-d$_6$) δ;1.32 (s,6H),
2.52~2.82 (m,4H), 5.90 (s,2H),
6.48~6.80 (m,3H)
MS (FAB) m/z; 313 (MNa$^-$), 291 (MH$^-$)

EXAMPLE 5

2-Oxo-3-[{2-(1,3-benzodioxol-5-yl)ethyl}thio]-propionic acid

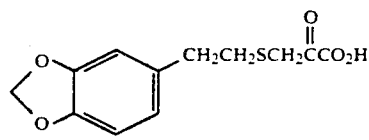

0.21 g of the intended compound was obtained as a keto-enol tautomeric mixture of 2:1 in the form of faint yellow crystals from 0.50 g of 2-(1,3-benzodioxol-5-yl)ethanethiol and 0.43 g of 3-bromopyruvic acid in the same manner as that of Example 1.

mp. ; 131°~132° C.
$^1$H-NMR (90MHz, CDCl$_3$-DMSO-d$_6$) δ;2.40
~3.08 (m,2H÷1H×⅓), 5.87 (s,2H),
6.20 (s,1H×⅔), 6.40~6.84(m,3H),
8.10 (bs,1H)
MS m/z; 268 (M$^-$)

EXAMPLE 6

2-(1,3-Benzodioxol-5-yl)ethyl (pyridin-4-yl)methyl sulfide

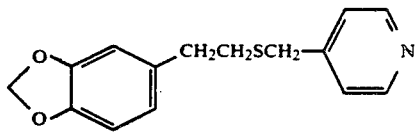

3.30 g of 2-(1,3-benzodioxol-5-yl)ethanethiol was dissolved in 30 ml of ethanol. 1.65 g of sodium hydroxide and then 2.70 g of 4-picolyl chloride hydrochloride were added to the solution and the mixture was heated under reflux at 70° C. for 30 min. The solvent was distilled off and water was added to the residue. After extraction with ethyl acetate, 1N hydrochloric acid was added to the extract. The aqueous layer was acidified, taken up and washed with ethyl acetate. The pH of the aqueous layer was adjusted to 8 with potassium carbonate. After extraction with ethyl acetate, the extract was washed with a saturated aqueous common salt solution and dried over anhydrous magnesium sulfate. After filtration, the solvent was distilled off and the residue was purified according to silica gel column chromatography (ethyl acetate/hexane=1:4) to obtain 2.69 g of the intended compound in the form of a colorless oil.

$^1$H-NMR (90MHz, CDCl$_3$)δ; 2.4~2.87 (m,4H),
3.60 (s,2H), 5.86 (s,2H), 6.35~
6.75 (m,3H), 7.05~7.25(m,2H),
8.25~8.57 (m,2H)
MS (FD) m/z;273 (M$^-$)

Example 7

2-(1,3-Benzodioxol-5-yl)ethyl (pyridin-2-yl)methyl sulfide

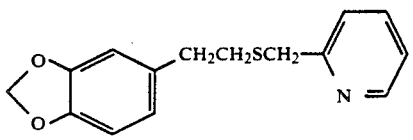

2.3 g of the intended compound in the form of a colorless oil was obtained from 3.0 g of 2-(1,3-benzodioxol-5-yl)ethanethiol and 2.7 g of 2-picolyl chloride hydrochloride in the same manner as that of Example 6. $^1$H-NMR (90MHz, CDCl$_3$) δ; 2.55~2.9 (m,4H),
3.86 (s,2H), 5.91 (s,2H), 6.45
~6.8 (m,3H), 7.0~7.3 (m,1H),
7.33 (bd,J=7.9Hz,1H), 7.61 (td,J
=7.9 and 2.2Hz,1H), 8.51 (bd,J=5.8
Hz,1H)
MS (FD) m/z;273 (M$^-$)

Example 8

2-(1,3-Benzodioxol-5-yl)ethyl (imidazol-4-yl)methyl sulfide

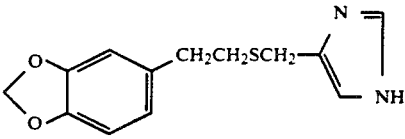

40 ml of thionyl chloride was added to 2.50 g of 4-hydroxyethylimidazole hydrochloride. The mixture was stirred under heating at 70° C. for 1 h. Thionyl chloride was distilled off. 3.39 g of 2-(1,3-benzodioxol-5-yl)ethanethiol, 40 ml of ethanol and 1.50 g of sodium hydroxide were added to the residue and the mixture was stirred under heating at 70° to 80° C. for 1 h. The solvent was distilled off and water was added to the residue. After extraction with chloroform containing 5% of methanol, the extract was dried over anhydrous magnesium sulfate, dried and filtered. The solvent was distilled off and the residue was purified according to silica gel column chromatography (methanol/ chloroform=1:49) to obtain 1.94 g of the intended compound in the form of colorless prismatic crystals.

mp.; 81°~83° C.
$^1$H-NMR (90MHz, CDCl$_3$)δ; 2.45~2.9(m,4H),
3.68(s,2H), 5.84(s,2H), 5.8~6.9
(broad,1H), 6.4~6.75(m,3H), 6.86
(bs,1H), 7.53(bs,1H)

MS m/z;262 (M⁻)

Example 9

4-{2-{2-(1,3-Benzodioxol-5-yl)ethyl}thio]ethyl-5-methylisoxazol-3-ol

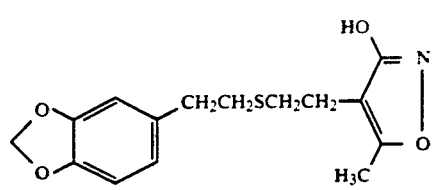

100 ml of tetrahydrofuran and 4.66 g of triethylamine were added to 2.84 g of 3-acetoxy-4-(2-hydroxyethyl)-5-methylisoxazole. 4.39 g of methanesulfonyl chloride was added dropwise thereto at −15° C. and the mixture was stirred at 0° C. or below for 1 h. The solvent was distilled off. After addition of ice/water followed by extraction with chloroform, the extract was washed with 1N hydrochloric acid, water, a saturated aqueous sodium hydrogencarbonate solution and a saturated aqueous common salt solution in this order and then dried over anhydrous magnesium sulfate. The solvent was distilled off and the resulting methanesulfonate was added to a solution comprising 4.19 g of 2-(1,3-benzodioxol-5-yl)ethanethiol, 30 m( of ethanol and 1.53 g of sodium hydroxide and the mixture was stirred under heating at 70° C. The solvent was distilled off and water was added to the residue. After extraction with chloroform containing 5% of methanol, the extract was washed with a saturated aqueous common salt solution and dried over anhydrous magnesium sulfate. After filtration, the filtrate was concentrated, purified according to silica gel column chromatography and recrystallized from ethyl acetate/hexane to obtain 0.96 g of the intended compound in the form of colorless needles.
mp. ;81°~81.5° C.
¹H-NMR (90MHz, CDCl₃) δ;2.25 (s,3H),
2.35~2.85 (m,8H), 5.87 (s,2H),
5.4~6.5 (br,1H), 6.45~6.75 (m, 3H)
MS m/z; 307 (M⁻)

Example 10

Sodium 4-[2-{2-(1,3-benzodioxol-5-yl)ethyl}thio]-ethyl-5-methylisoxazol-3-ol

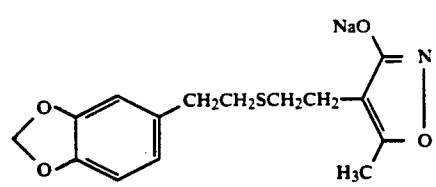

1.01 g of the intended compound in the form of a white powder was obtained from 0.95 g of 4-[2-{2(1,3-benzodioxol-5-yl)ethyl}thio]ethyl-5-methyl-isoxazol-3-ol in the same manner as that of Example 4.
mp.; 144°~152° C. (dec.)
¹H-NMR (90MHz, DMSO-d₆) δ;1.98 (s,3H),
2.1~2.8 (m,4H), 2.68 (bs,4H),
5.88 (s,2H), 6.48~6.9 (m,3H)
MS (FAB) m/z 352 (MNa⁻), 330 (MH⁻)

Example 11

[{2-(2-Methyl-1,3-benzodioxol-5-yl)ethyl}thio]acetic acid

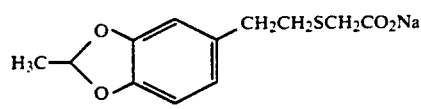

0.97 g of methanesulfonyl chloride was added dropwise to a solution of 0.76 g of 5-(2-hydroxyethyl)-2-methyl-1,3-benzodioxole and 1.2 ml of triethylamine in 10 ml of methylene chloride and the mixture was stirred at room temperature for 30 min. The reaction mixture was diluted with chloroform, washed with cold water, then a saturated sodium hydrogencarbonate solution and finally an aqueous common salt solution and dried over magnesium sulfate. The solvent was distilled off. 0.9 g of mercaptoacetic acid, 10 ml of a 10% sodium hydroxide solution and 10 ml of ethanol were added to the oil (mesylate) thus obtained and the mixture was heated at 80° C. for 30 min. The reaction mixture was concentrated and the aqueous layer was washed with ethyl ether and then acidified with dilute hydrochloric acid. The aqueous layer was extracted with chloroform and dried over magnesium sulfate. The solvent was distilled off and the product was purified according to silica gel column chromatography (methanol/chloroform= 1:99) to obtain 1.0 g of the intended compound in the form of a faint brown oil.
¹H-NMR (90MHz, CDCl₃) δ;1.66 (d,J=5Hz,3H),
2.84 (s,4H), 3.24 (s,2H), 6.20(q,
J=5Hz,1H), 6.63 (m,3H), 9.95 (m,1H)

Example 12

Sodium [{2-(2-methyl-1,3-benzodioxol-5-yl)ethyl}thio]acetate

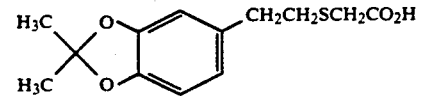

0.7 g of the intended compound in the form of a white powder was obtained from 1.0 g of [{2-(2-methyl-1,3-benzodioxol-5-yl)ethyl}thio]acetic acid in the same manner as that of Example 4.
mp. ;200°~205° C. (dec.)
¹H-NMR (400MHz, DMSO -d₆) δ;1.58 (d,J= 4.8Hz,3H), 2.68 (m,4H), 2.96 (s, 2H), 6.28 (q,J=4.8Hz,1H), 6.62~ 6.75 (m,3H)
MS (FAB) m/z 299 (MNa⁻), 276 (MH⁻)

Example 13

[{2-(2,2-Dimethyl-1,3-benzodioxol-5-yl)ethyl}thio]acetic acid 3.4 g of the intended compound in the form of a colorless oil was obtained from 4.3 g of 2,2-dimethyl-5-(2-hydroxyethyl)-1,3-benzodioxole in the same manner as that of Example 11.

¹H-NMR (90MHz, CDCl₃) δ:1.65 (s,6H),
2.84 (s,4H), 3.25 (s,2H), 6.61(m,
3H), 9.84 (m,1H)

Example 14

Sodium [{2-(2,2-dimethyl-1,3-benzodioxol-5-yl)ethyl}thio]acetate

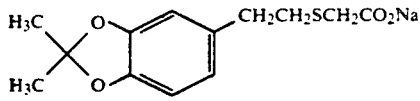

3.3 g of the intended compound in the form of a white powder was obtained from 3.3 g of [{2-(2,2-dimethyl-1,3-benzodioxol-5-yl)ethyl}thio]acetic acid in the same manner as that of Example 4.

mp. ;199°~202° C. (dec.)
¹H-NMR (400MHz, DMSO -d₆) δ;1.60 (s,6H),
2.68 (s,4H), 2.95 (s,2H), 6.60~
6.71 (m,3H)
MS (FAB) m/z 313 (MNa⁻), 291 (MH⁻)

Example 15

[{2-(6-Methyl-1,3-benzodioxol-5-yl)ethyl}thio3acetic acid

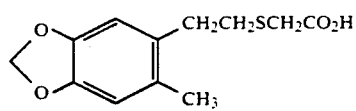

1.5 g of the intended compound in the form of a white powder was obtained from 1.5 g of 2-(6-methyl-1,3-benzodioxol-5-yl)ethanol in the same manner as that of Example 11.

¹H-NMR (90MHz, CDCl₃) δ;2.22 (s,3H),
2.82(s,4H), 3.26 (s,2H), 5.88 (s,
2H), 6.66 (s,2H), 10.56 (bs,1H)

Example 16

Sodium [{2-(6-methyl-1,3-benzodioxol-5-yl)ethyl}thio]acetate

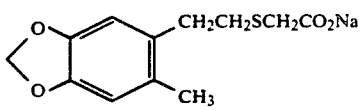

1.6 g of the intended compound in the form of a white powder was obtained from 1.5 g of [{2-(6-methyl-1,3-benzodioxol-5-yl)ethyl}thio]acetic acid in the same manner as that of Example 4.

mp.; 194°~195° C.
¹H-NMR (400MHz, DMSO-d₆) δ;2.17 (s,3H),
2.59~2.63 (m,2H), 2.67~2.72 (m,
2H), 2.96 (s,2H), 5.90 (s,2H),
6.70 (s,1H), 6.75 (s,1H)
MS (FAB) m/z ;277 (MH⁻)

Example 17

[{2-(6-Ethyl-1,3-benzodioxol-5-yl)ethyl}thio]acetic acid

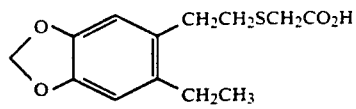

85 g of the intended compound in the form of a white powder was obtained from 169 g of 2-(6-ethyl-1,3-benzodioxol-5-yl)ethanol in the same manner as that of Example 11.

mp. ; 63°~64° C.
¹H-NMR (90MHz, CDCl₃) δ;1.16 (t,J=7Hz,3H),
2.52 (q,J=7Hz,2H), 2.82 (s,4H),
3.24 (s,2H), 5.84 (s,2H), 6.58
(s,1H), 6.60 (s,1H), 9.80 (bs,1H)

Example 18

Sodium [{2-(6-ethyl-1,3-benzodioxol-5-yl)ethyl}thio]acetate

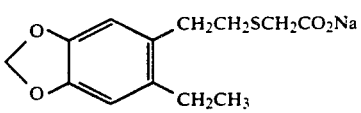

91 g of the intended compound in the form of a white powder was obtained from 85 g of f{2-(6-ethyl-1,3-benzodioxol-5-yl)ethyl}thio]acetic acid in the same manner as that of Example 4.

mp. ; 193~°196° C. (dec.)
¹H-NMR (400MHz, DMSO-d₆) δ;1.10 (t,J=
7Hz,3H), 2.51 (q,J=7Hz,2H), 2.60
~2.65 (m,2H), 2.69~2.74 (m,2H),
2.79 (s,2H), 5.91 (s,2H), 6.71
(s,1H), 6.75 (s,1H)
MS (FAB) m/z ; 291 (MH⁻)

Example 19

[{2-(6-Propyl-1,3-benzodioxol-5-yl)ethyl}thio]acetic acid

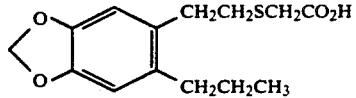

1.4 g of the intended compound in the form of colorless crystals was obtained from 1.4 g of 2-(6-propyl-1,3-benzodioxol-5-yl)ethanol in the same manner as that of Example 11.

mp. ; 72.5°~73.5° C.
¹H-NMR (90MHz, CDCl₃) δ;0.96 (t,J=7Hz,3H),
1.56 (sext,J=7Hz,2H), 2.52 (t,J=
7Hz,2H), 2.84 (s,4H), 3.48 (s,2H),
5.90 (s,2H), 6.64 (s,2H)

Example 20

Sodium [{2-(6-propyl-1,3-benzodioxol-5-yl)ethyl}thio]acetate

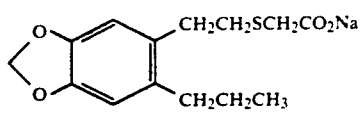

1.5 g of the intended compound in the form of a white powder was obtained from 1.4 g of f{2-(6-propyl-1,3-benzodioxol-5-yl)ethyl}thio]acetic acid in the same manner as that of Example 4.

mp.; 189°~190° C.

$^1$H-NMR(400MHz, DMSO-d$_6$) δ;0.96 (t,J=7 Hz,3H), 1.49 (sext,J=7Hz,2H), 2.46 (t,J=8Hz,2H), 2.62~2.64 (m,2H), 2.69~2.72 (m,2H), 3.00 (s,2H), 5.90 (s,2H), 6.69 (s,1H), 6.75 (s,1H).

MS (FAB) m/z ;305(MH$^-$)

Example 21

3-{6-(2-Ethylthio)ethyl-1,3-benzodioxol-5-yl}propionic acid

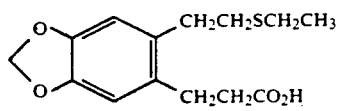

2.2 g of the intended compound in the form of a white powder was obtained from 3.5 g of ethyl 3-{6-(2-methanesulfonyloxy)ethyl-1,3-benzodioxol-5-yl}propionate and 1 g of ethyl mercaptan in the same manner as that of Example 11.

$^1$H-NMR (90MHz, CDCl$_3$) δ;1.28 (t,J=7.2Hz, 3H), 2.50~3.10 (m,10H), 5.99 (s, 2H), 6.75 (s,2H)

Example 22

Sodium 3-{6-(2-ethylthio)ethyl-1,3-benzodioxol-5yl}propionate

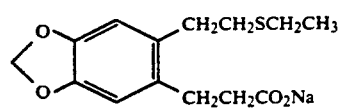

1.9 g of the intended compound in the form of a white powder was obtained from 2.2 g of 3-{6-(2-ethylthio)ethyl-1,3-benzodioxol-5-yl}propionic acid in the same manner as that of Example 4.

mp. ; 218°~222° C.

$^1$H-NMR (90MHz, DMSO-d$_6$) δ;1.20 (t,J=7.2 Hz,3H), 1.94~2.26 (m,2H), 2.28~2.88 (m,8H), 5.84 (s,2H), 6.67 (s,2H)

MS (FAB) m/z ;327 (MNa$^-$), 305 (MH$^-$)

Example 23

[[{2-(1,3-Benzodioxol-5-yl)-1,1-dimethyl}ethyl]thio]acetic acid

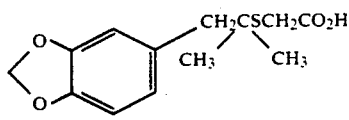

30 ml of benzene was added to a mixture of 5 g of 1-(1,3-benzodioxol-5-yl)-2-methyl-1-propene, 2.6 g of mercaptoacetic acid and a catalytic amount of α,α'-azobisisobutyronitrile. The mixture was refluxed for 2 days. 2.6 g of mercaptoacetic acid was added thereto and the mixture was refluxed for one week. 200 ml of ethyl acetate and 200 ml of water were added to the reaction mixture and the layers thus formed were separated. An aqueous sodium carbonate solution was added to the ethyl acetate layer to extract the intended compound. The aqueous layer was acidified with dilute hydrochloric acid. After extraction with ethyl acetate, the extract was washed with water and dried over anhydrous sodium sulfate. The solvent was distilled off and the residue was purified according to silica gel column chromatography (hexane/ethyl acetate/acetic acid=20:80:1). The product was dissolved in ethyl acetate, washed with water to remove acetic acid and dried over anhydrous sodium sulfate. The solvent was distilled off to obtain 3.33 g of the intended compound in the form of a colorless oil.

$^1$H-NMR (90MHz, CDCl$_3$) δ;1.29 (s,6H), 2.78 (s,2H), 3.29 (s,2H), 5.92 (s,2H), 6.52~6.80 (m,3H)

Example 24

Sodium [[{2-(1,3-benzodioxol-5-yl)-1,1-dimethyl}ethyl]thioacetate

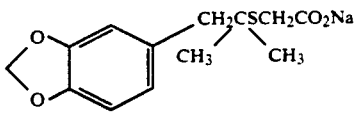

2.1 g of the intended compound in the form of colorless crystals was obtained from 3.33 g of [[{2-(1,3-benzodioxol-5-yl)-1,1-dimethyl}ethyl3thio]acetic acid in the same manner as that of Example 4.

mp. ;206°~210° C.

$^1$H-NMR (90MHz, DMSO-d$_6$) δ;1.14 (s,6H), 2.68 (s,2H), 3.02 (s,2H), 5.94 (s,2H), 6.52~6.88 (m,3H)

MS (FD) m/z ;313(MNa$^-$), 291(MH$^-$)

Example 25

[[1-{(1,3-Benzodioxol-5-yl)methyl}propyl]thio]acetic acid

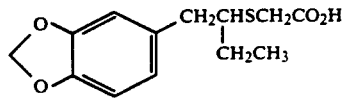

2.2 g of 5-(1-butenyl)-1,3-benzodioxole and 5.4 g of mercaptoacetic acid were heated at 60° C. for 3 h. The reaction mixture was diluted with ethyl acetate, washed with water and an aqueous common salt solution and dried over magnesium sulfate. The solvent was distilled off and the product was separated according to silica gel column chromatography (chloroform) to obtain 1.8 g of the intended compound in the form of a colorless oil.

$^1$H-NMR (90MHz, CDCl$_3$) δ;1.00 (t,J=7Hz,3H), 1.54 (m,2H), 2.69~3.00 (m,3H),
3.14 (s,2H), 5.87 (s,2H), 6.62 (m,3H), 8.7 (m,1H)

Example 26

Sodium [[1-{(1,3-benzodioxol-5-yl)methyl}propyl]thio]-acetate

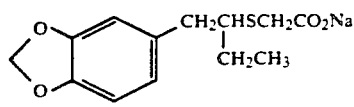

1.7 g of the intended compound in the form of a white powder was obtained from 1.7 g of [[1-{(1,3-benzodioxol-5-yl)methyl}propyl]thio]acetic acid in the same manner as that of Example 4.

mp. ;184°~188° C. (dec);

$^1$H-NMR (400MHz, DMSO -d$_6$) δ;0.89 (t,J= 7.3Hz,3H), 1.31 (m,1H), 1.48 (m, 1H), 2.43~2.59 (m,1H), 2.80~2.90(m,2H), 2.90 and 2.96 (ABq,J=13.2Hz,2H), 5.96 (m,2H), 6,65 (m, 1H), 6.77~6.82 (m,2H)

MS (FAB) m/z ;291(MH$^-$)

Example 27

[{2-(1,3-Benzodioxol-5-yl)ethyl}thio]cyanoacetic acid

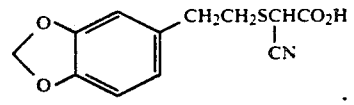

5.0 g of [{2-(1,3-benzodioxol-5-yl)ethyl}thio]-acetonitrile was dissolved in 50 ml of anhydrous ether. 22 ml of a 1.6 M solution of n-butyllithium in hexane was added to the solution at −78° C. The mixture was stirred at −50° C. for 2 h. It was cooled again to −78° C. and 10 g of dry ice was added thereto. The temperature of the mixture was elevated to room temperature. Water was added to the reaction mixture. After extraction with chloroform, the extract was dried over magnesium sulfate and concentrated. The residue was purified according to silica gel column chromatography (chloroform) and recrystallized from ethyl acetate/hexane to obtain 0.70 g of the intended compound in the form of colorless needles.

mp. ;106°~107° C.

$^1$H-NMR (90MHz, DMSO-d$_6$) δ;2.62~3.10 (m,4H), 5.12 (s,1H), 5.90 (s,2H), 6.50~6.86 (m,3H)

MS (FAD) m/z ;265 (MH$^-$)

Example 28

Sodium [{2-(1,3-benzodioxol-5-yl)ethyl}thio]-cyanoacetate

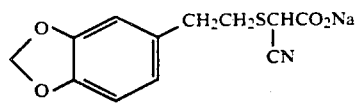

0.59 g of the intended compound in the form of a white powder was obtained from 0.70 g of [{2-(1,3-benzodioxol-5-yl)ethyl}thio]cyanoacetate acid in the same manner as that of Example 4.

mp. ;202°~208° C. (dec.)

$^1$H-NMR (400MHz, DMSO -d$_6$) δ;2.80~2.84 (m,2H), 2.88~2.92 (m,2H), 4.25~4.50 (bs,1H), 5.97 (s,2H), 6.70~6.86 (m,3H)

MS (FAB) m/z ;310 (MNa$^-$)

Example 29

N,N-Dimethyl-2-[{2-(1,3-benzodioxol-5-yl)-2-ethyl}-thio]ethanesulfonamide

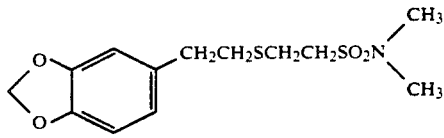

4 g of 2-[{2-(1,3-benzodioxol-5-yl)-2-ethyl}-thio]-ethanesulfonyl chloride was dissolved in chloroform. Gaseous dimethylamine was introduced thereinto under stirring. The chloroform solution was washed with water and dried over anhydrous sodium sulfate. The solvent was distilled off and the residue was purified according to silica gel column chromatography (chloroform). The product was recrystallized from isopropyl ether/ethanol to obtain 3.0 g of the intended compound in the form of colorless crystals.

mp. ;93°~94.5° C.

$^1$H-NMR (90MHz, CDCl$_3$) δ;2.75 (s,4H), 2.83 (s,6H), 2.68~3.19 (m,4H), 5.86(s, 2H), 6.48~6.76 (m,3H)

MS m/z ;317 (M$^-$), 149, 135

EXAMPLE 30

[{2-(1,3-Benzodioxol-5-yl)ethyl}sulfinyl]propan-2-one

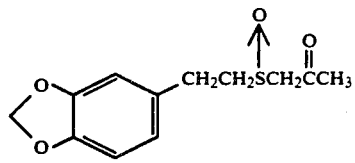

4 g of [{2-(1,3-benzodioxol-5-yl)ethyl}thio3-propan-2-one was dissolved in 70 m( of chloroform. 3.2 g of 90% m-chloroperbenzoic acid was added to the solution under cooling with ice/water. The mixture was stirred for 40 min. 150 ml of chloroform and an aqueous sodium carbonate solution were added to the reaction mixture. After separation of the layers thus formed, the chloroform layer was washed with water three times and dried over anhydrous sodium sulfate. The solvent was distilled off and the residue was recrystallized from isopropyl ether to obtain 3.5 g of the intended compound in the form of colorless crystals.

mp. ;82°~84.5° C.
¹H-NMR (90MHz, CDCl₃) δ:2.32 (s,3H), 2.99 (s,4H), 3.65 and 3.77 (ABq,J=13.5Hz,2H), 5.89 (s,2H), 6.50~6.77 (m,3H)
MS (FAB) m/z ;255 (MH⁻), 149

Example 31

5-{2-(Ethylsulfinyl)ethyl}-1,3-benzodioxole

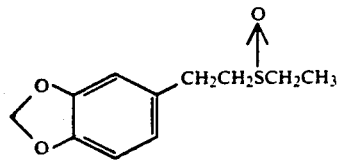

3.0 g of the intended compound in the form of colorless crystals was obtained from 4 g of 5-(2-ethylthio)ethyl-1,3-benzodioxole in the same manner as that of Example 30.

mp.; 60.5°~61.5° C.
¹H-NMR (90MHz, CDCl₃) δ;1.33 (t,J=7.2Hz, 3H), 2.71 (q,J=7.2Hz,2H), 2.72~3.18 (m,4H), 5.92 (s,2H), 6.54~6.83 (m,3H)
MS (FAB) m/z ;227 (MH⁻)

Example 32

5-{2-(1-Methylethylsulfinyl)ethyl}-1,3-benzodioxole

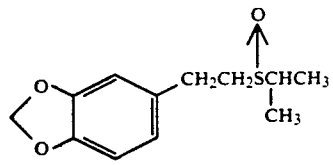

3.7 g of the intended compound in the form of colorless oil was obtained from 4 g of 5-{2-(1methylethyl)thio}ethyl-1,3-benzodioxole in the same manner as that of Example 30.
¹H-NMR (90MHz, CDCl₃) δ:1.24 (d,J=5.4Hz, 3H), 1.31 (d,J=5.4Hz,3H), 2.45~3.27 (m,5H), 5.88 (s,2H), 6.53~6.78 (m,3H)
MS (FAB) m/z; 241 (MH⁻), 149

Example 33

[{2-(1,3-Benzodioxol-5-yl)ethyl}sulfinyl]acetonitrile

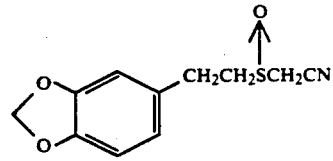

3.0 g of the intended compound in the form of colorless crystals was obtained from 3 g of [{2-(1,3-benzodioxol-5-yl)ethyl}thio]acetonitrile in the same manner as that of Example 30.

mp.; 57°~59.5° C.
¹H-NMR (90MHz, CDCl₃) δ;2.76~3.34 (m,4H), 3.53 and 3.69 (ABq,J=16.4Hz,2H), 5.90 (s,2H), 6.52~6.79 (m,3H)
MS (FAB) m/z ;238 (MH⁻), 149

Example 34

[{2-(1,3-benzodioxol-5-yl)ethyl}sulfonyl]propan-2-one

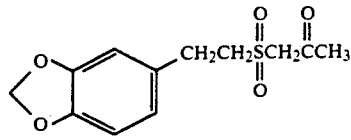

4 g of [{2-(1,3-benzodioxol-5-yl)ethyl}thio]-propan-2-one was dissolved in 70 m( of chloroform. 8.1 g of 90% m-chloroperbenzoic acid was added to the solution under cooling with ice/water and the mixture was stirred for 2 h. 150 ml of chloroform and an aqueous sodium carbonate solution were added to the reaction mixture. After separation of the layers thus formed, the chloroform layer was washed with water three times and dried over anhydrous sodium sulfate. The solvent was distilled off and the residue was recrystallized from ethyl acetate/ isopropyl ether to obtain 4.1 g of the intended compound in the form of colorless crystals.

mp. ;97°~99° C.
¹H-NMR (90MHz, CDCl₃) δ;239 (s,3H), 2.88~3.47 (m,4H), 3.92 (s,2H), 5.89 (s,2H), 6.50~6.77 (m,3H)
MS (FAB) m/z; 270 (M⁻), 149

Example 35

5-{2-(Ethylsulfonyl)ethyl}-1,3-benzodioxole

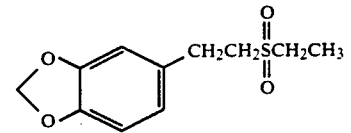

3.5 g of the intended compound in the form of colorless crystals was obtained from 4 g of 5-(2-ethylthio)ethyl-1,3-benzodioxole in the same manner as that of Example 34.

mp. ;90°~91° C.
¹H-NMR (90MHz, CDCl₃) δ;1.38 (t,J=7.4Hz, 3H), 2.92 (q,J=7.4Hz,2H), 3.00~3.22 (m,4H), 5.93 (s,2H), 6.57~6.18 (m,3H)
MS (FAB) m/z ;243 (MH⁻), 149

Example 36

5-{2-(1-Methylethylsulfonyl)ethyl}-1,3-benzodioxole

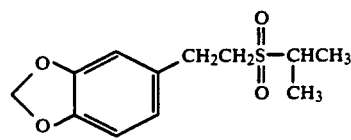

4.0 g of the intended compound in the form of colorless crystals was obtained from 4 g of 5-[2-(1-methylethyl)thio}ethyl-1,3-benzodioxole in the same manner as that of Example 34.

mp. ;83°~85° C.

¹H-NMR (90MHz, CDCl₃) δ;1.39 (d,J=6.8Hz, 6H), 2.82~3.27 (m,5H), 5.90 (s, 2H), 6.44~6.78 (m,3H)
MS m/z ;256 (MH⁻), 149

Example 37

[{2-(1,3-Benzodioxol-5-yl)ethyl}sulfonyl]acetonitrile

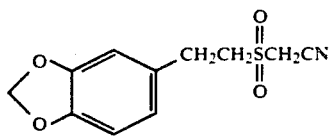

2.95 g of the intended compound in the form of colorless crystals was obtained from 3 g of [{2-(1,3-benzodioxol-5-yl)ethyl}thio]acetonitrile in the same manner as that of Example 34.
mp. ;93°~95° C.
¹H-NMR (90MHz, CDCl₃) δ:2.95~3.30 (m,2H), 3.33~3.67 (m,2H), 3.75 (s,2H),
5.91 (s,2H), 6.56~6.88 (m,3H)
MS m/z ;253 (M⁻), 149

Compound Group (I-e)

Preparative Example 1

2-(1,3-Benzodioxol-5-yl)ethanethiol

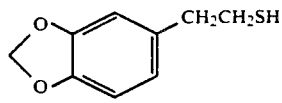

750 g of 5-(2-bromoethyl)-1,3-benzodioxole was dissolved in 1 l of ethanol, followed by the addition of 312 g of thiourea. The mixture was heated under reflux on a boiling water bath for 2 hours and cooled, followed by the addition of a solution of 300 g of sodium hydroxide in 1 l of water. The obtained mixture was heated under reflux on a boiling water bath for 45 minutes and cooled, followed by the addition of 3 l of water. The obtained mixture was extracted with 5 l of ethyl acetate. The extract was washed with dilute hydrochloric acid and then with water until the washings became neutral, dried over anhydrous sodium sulfate and distilled at 40° C. to remove the solvent. About 570 g of a yellow oil was obtained. This oil was purified by silica gel column chromatography (hexane/benzene=2:1) to obtain 310 g of the title compound as a colorless oil.
¹H-NMR (90MHz, CDCl₃) δ;
1.36(m,1H), 2.6~2.9(m,4H), 5.87(s,2H), 6.50~6.74(m,3H)

Preparative Example 2

3-(1,3-Benzodioxol-5-yl)propanethiol

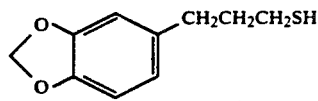

25 g of thioacetic acid was added to 53.5 g of safrole in portions, while stirring the mixture at a room temperature or under cooling with ice/water. The reaction was carried out for 30 minutes. A solution of 20 g of sodium hydroxide in a mixture comprising 100 ml of water and 200 ml of ethanol was added to the reaction mixture The obtained mixture was heated under reflux for 20 minutes, cooled, neutralized with dilute sulfuric acid and extracted with 1 l of benzene. The extract was washed with water and the benzene layer was dried over anhydrous sodium sulfate and purified by silica gel column chromatography (hexane) to obtain 42.8 g of the title compound as a colorless oil.
¹H-NMR (90MHz, CDCl₃) δ;
1.20~1.46(m,1H), 1.68~2.10(m,2H), 2.34~2.78(m,4H), 5.84(s,2H), 6.44~6.75(m,3H)

Preparative Example 3

2-(1,3-Benzodioxol-5-yl)-1-methylethanethiol

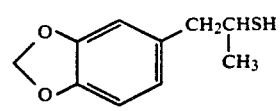

5 g of anhydrous tin chloride was added to 100 g of safrole. Hydrochloric acid gas was passed though the mixture under cooling with ice for 1.5 hours. 2 l of ethyl acetate was added to the reaction mixture, followed by the dissolution. The obtained mixture was washed with water twice, dried over anhydrous sodium sulfate and distilled to remove the solvent. The residue was purified by silica gel column chromatography (hexane/benzene=10:1) to obtain 41.7 g of 5-(2-chloropropyl)-1,3-benzodioxole as a colorless oil. This oil was dissolved in 150 ml of ethanol, followed by the addition of 48 g of thiourea. The obtained mixture was heated under reflux for 7 days, cooled and filtered. A solution of 12.8 g of sodium hydroxide in 100 ml of water was added to the filtrate. The obtained mixture was heated under reflux for 2 hours, cooled and acidified with dilute sulfuric acid. 1 l of benzene and 1 l of water were added to the mixture to carry out the phase separation. The benzene layer was washed with water twice, dried over anhydrous sodium sulfate and distilled to remove the solvent. The residue was purified by silica gel column chromatography (hexane/benzene=10:1) to obtain 8.5 g of the title compound as a colorless oil.
¹H-NMR (90MHz, CDCl₃) δ;
1.32(d,J=6Hz,3H), 1.54(d,J=6Hz,1H), 2.61~2.84(m,2H), 2.90~3.35(m,1H), 5.86(s,2H), 6.46~6.76(m,3H)

Example 1 (Compound 1)

2-[{2-(1,3-Benzodioxol-5-yl)ethyl}dithio]ethanol

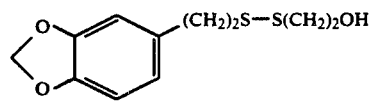

35 g of 2-(1,3-benzodioxol-5-yl)ethanethiol and 75 g of 2-mercaptoethanol were dissolved in 150 ml of ethanol, followed by the addition of 43 g of iodine. The obtained mixture was stirred at a room temperature for 30 minutes, followed by the addition of 2 l of ethyl acetate and 2 l of water. The mixture was separated into two phases. The ethyl acetate layer was washed with water twice, then with 1 l of a 1% aqueous solution of sodium hydrogensulfite twice and finally with water thrice, dried over anhydrous sodium sulfate and filtered. The filtrate was distilled to remove the solvent.

The residue was purified by silica gel column chromatography (benzen/ethyl acetate=10:1) to obtain 11.5 g of the title compound as a colorless oil.

¹H-NMR (90MHz, CDCl₃) δ;
1.98(t,J=7Hz,1H), 2.85(t,J=7Hz,2H), 2.91 (s,4H), 3.89(q,J=7Hz,2H),5.92(s,2H), 6.55 ~6.84(m,3H)
MS m/z; 258(M⁻), 149

Example 2 (Compound 2)

Bis{2-(1,3-benzodioxol-5-yl)ethyl}disulfide

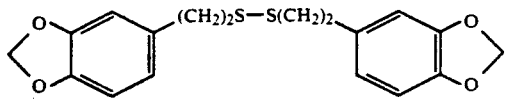

2 g of the title compound was prepared from 3 g of 2-(1,3-benzodioxol-5-yl)ethanethiol as a colorless oil according to the same procedure as that described in Example 1.

mp.: 76° to 78° C.
¹H-NMR (90MHz, CDCl₃) δ;
2.87(s,8H), 5.90(s,4H),6.51~6.81(m,6H)
.MS m/z: 362(M⁻), 149

Example 3 (Compound 3)

2-[{2-(1,3-Benzodioxol-5-yl)ethyl}dithio]ethyl nicotinate

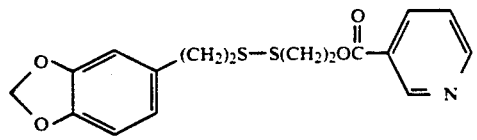

4 g of the 2-[{2-(1,3-benzodioxol-5-yl)ethyl}-dithio] ethanol prepared in Example 1 was dissolved in a mixture comprising 20 ml of pyridine and 50 ml of benzene to obtain a solution. 4 g of nicotinyl chloride hydrochloride was added to the solution. The obtained mixture was heated under reflux for 2 hours and poured into ice/water. The obtained mixture was weekly basified with sodium hydrogencarbonate. Ethyl acetate was added to the mixture to carry out the phase separation. The ethyl acetate layer was washed with water five times, dried over anhydrous sodium sulfate and distilled to remove the solvent. The residue was purified by silica gel column chromatography (hexane/ethyl acetate=3:1) to obtain 5.4 g of the title compound as a colorless oil.

¹H-NMR (90MHz, CDCl₃) δ;
2.92(s,4H),3.06(t,J=7Hz,2H), 4.62(t,J= 7Hz,2H), 5.92(s,2H), 6.40~6.86(m,3H), 7.30 ~7.50(m,1H), 8.20~8.41(m,1H), 8.68~8.85 (m,1H), 9.14~9.34(m,1H)
MS m/z; 363(M⁻), 149

Example 4 (Compound 4)

2-[{2-(1,3-Benzodioxol-5-yl)ethyl}dithio]ethyl nicotinate hydrochloride

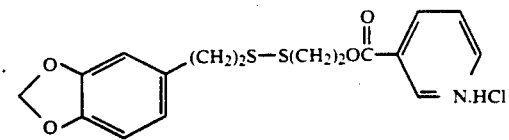

2.5 g of the 2-[{2-(1,3-benzodioxol-5-yl)dithio]ethyl nicotinate prepared in Example 3 was dissolved in 20 ml of ethyl acetate, followed by the addition of a solution of hydrochloric acid in ethyl acetate. The mixture was distilled to remove the solvent. The residue was dissolved in a methanol/ ethanol mixture, followed by the filtration. The filtrate was concentrated and recrystallized from an ethanol/isopropyl ether mixture to obtain 2.5 g of the title compound as a colorless crystal.

m.p.: 113° to 122° C.
¹H-NMR (90MHz, DMSO-d₆) δ; 2.66~3.00(m,4H), 3.11(t,J=7Hz,2H), 4.53 (t,J=7Hz,2H), 5.90(s,2H), 6.48~6.92(m,3 H), 7.62~7.91(m,1H), 8.36~8.60(m,1H), 8.78~9.02(m,1H), 9.02~9.24(m,1H)
MS m/z; 363, 149

| Elemental analysis: as C₁₇H₁₇NS₂.HCl | | | | |
|---|---|---|---|---|
| | C | H | N | Cl |
| calculated (%) | 51.06 | 4.54 | 3.50 | 8.87 |
| found (%) | 51.05 | 4.51 | 3.59 | 8.84 |

Example 5 (Compound 5)

2-[{3-(1,3-Benzodioxol-5-yl)propyl}dithio]ethanol

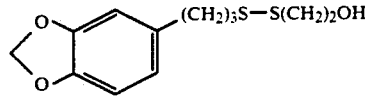

8.4 g of the title compound was prepared from 27.8 g of 3-(1,3-benzodioxol-5-yl)propanethiol and 5.5 g of 2-mercaptoethanol as a colorless oil according to the same procedure as that described in Example 1.

¹H-NMR (90MHz, CDCl₃) δ;
1.72~2.14(m,3H), 2.48~2.72(m,4H), 2.80 (t,J=7Hz,2H), 3.84(q,J=7Hz,2H), 5.85(s,2 H), 6.44~6.74(m,3H)
MS m/z; 272(M⁻), 135

Example 6 (Compound 6)

3-(1,3-Benzodioxol-5-yl)propyl phenethyl disulfide

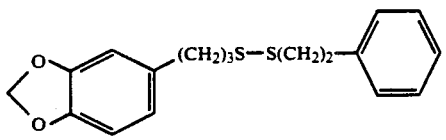

1.5 g of the title compound was prepared from 5 g of 3-(1,3-benzodioxol-5-yl)propanethiol and 5 g of phenethyl mercaptan as a colorless oil according to the same procedure as that described in Example 1.

$^1$H-NMR (90MHz, CDCl$_3$) δ;
1.70~2.20(m,2H), 2.50~2.8(m,4H), 2.92 (s,4H), 5.85(s,2H), 6.44~6.78(m,3H), 7.00 ~7.52(m,5H)
MS m/z; 332(M$^-$)

Example 7 (Compound 7)

2-[{3-(1,3-Benzodioxol-5-yl)propyl}dithio]ethyl nicotinate

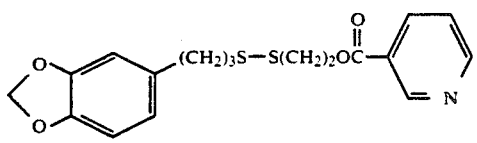

56.1 g of the title compound was prepared from 50 g of the 2-[{3-(1,3-benzodioxol-5-yl)propyl}dithio]ethanol and 50 g of nicotinyl chloride hydrochloride as a colorless oil according to the same procedure as that described in Example 3.

$^1$H-NMR (90MHz, CDCl$_3$) δ;
1.72~2.12(m,2H), 2.65(q,J=7Hz,4H), 3.00 (t,J=7Hz,2H), 4.56(t,J=7Hz,2H), 5.85(s,2 H), 6.42~6.70(m,3H), 7.20~7.40(m,1H), 8.10~8.30(m,1H), 8.58~8.78(m,1H), 9.06 ~9.22(m,1H)
MS m/z; 377(M$^-$)

Example 8 (Compound 8)

2-[{3-(1,3-Benzodioxol-5-yl)propyl}dithio]ethyl nicotinate hydrochloride

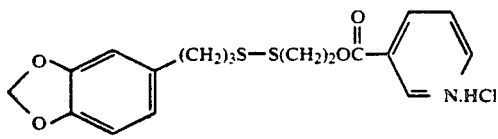

48.5 g of the title compound was prepared from 46.1 g of 2-[{3-(1,3-benzodioxol-5-yl)propyl}dithio]ethyl nicotinate as a colorless crystal according to the same procedure as that described in Example 4.
m.p.: 105° to 110° C.

$^1$H-NMR (90MHz, DMSO-d$_6$) δ; 1.68~2.08(m,2H), 2.71(q,J=7Hz,4H), 3.13 (t,J=7Hz,2H), 4.58(t,J=7Hz,2H), 5.96(s,2 H), 6.54~6.87(m,3H), 7.69~7.90(m,1H), 8.44~8.64(m,1H), 8.87~9.02(m,1H), 9.12 ~9.24(m,1H)
MS m/z; 377

| Elemental analysis: as C$_{18}$H$_{19}$O$_4$NS$_2$.HCl | | | | |
|---|---|---|---|---|
| | C | H | N | Cl |
| calculated (%) | 52.23 | 4.87 | 3.38 | 8.56 |
| found (%) | 52.32 | 4.80 | 3.47 | 8.58 |

Example 9 (Compound 9)

3-(1,3-Benzodioxol-5-yl)propyl nonyl disulfide

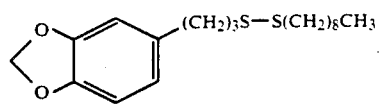

6.2 g of the title compound was prepared from 10 g of 3-(1,3-benzodioxol-5-yl)propanethiol and 5 g of nonyl mercaptan as a colorless oil according to the same procedure as that described in Example 1.

$^1$H-NMR (90MHz, CDCl$_3$) δ;
0.74~1.02(m,3H), 1.08~1.48(bs,14H), 1.80 ~2.12(m,2H), 2.50~2.76(m,6H), 5.86(s,2H), 6.46~6.75(m,3H)
MS m/z; 354(M$^-$)

Example 10 (Compound 10)

2-[{(1,3-Benzodioxol-5-yl)methyl}dithio]ethyl nicotinate

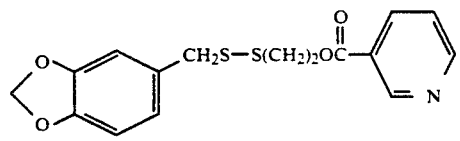

2.8 g of the title compound was prepared from 2 g of 2-[{(1,3-benzodioxol-5-yl)methyl}dithio]ethanol and 2.2 g of nicotinyl chloride hydrochloride as a colorless oil according to the same procedure as that described in Example 3.

$^1$H-NMR (90MHz, CDCl$_3$) δ;
2.76(t,J=7Hz,2H), 3.82(s,2H), 4.45(t,J =7Hz,2H), 5.89(s,2H), 6.52~6.91 (m,3H), 7.12~7.42(m,1H), 8.10~8.34(m,1H), 8.64 ~8.87(m,1H), 9.07~9.28(m,1H)
MS m/z; 349(M$^-$)

Example 11 (Compound 11)

Bis{2-(1,3-benzodioxol-5-yl)-1-methylethyl}disulfide

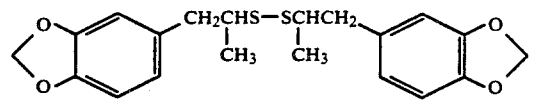

3.5 g of the title compound was prepared from 4 g of 2-(1,3-benzodioxol-5-yl)-1-methylethanethiol as a colorless oil according to the same procedure as that described in Example 1.

$^1$H-NMR (90MHz, CDCl$_3$) δ;
1.24(d,J=7Hz,6H), 2.32~2.71(m,2H), 2.72 ~3.16(m,4H), 5.91(s,4H), 6.48~6.82(m,6 H)
MS m/z; 390(M$^-$)

Example 12 (Compound 12)

2-[{2-(1,3-Benzodioxol-5-yl)-1-methylethyl}dithio]ethanol

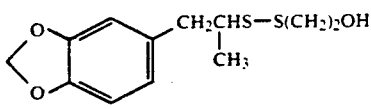

5.0 g of the title compound was prepared from 8.4 g of 2-(1,3-benzodioxol-5-yl)-1-methylethanethiol and 2.24 g of 2-mercaptoethanol as a colorless oil according to the same procedure as that described in Example 1.

$^1$H-NMR (90MHz, CDCl$_3$) δ;
1.27(d,J=7Hz,3H), 1.80~2.20(br,1H), 2.40~2.80(m,1H), 2.68~3.25(m,4H), 3.60~4.10(br,2H), 5.90(s,2H), 6.50~6.88(m,3H)
MS m/z; 272(M$^-$)

Compound Group (I-f)

Preparative Example 1

2-(1,3-Benzodioxol-5-yl)-2-propanol

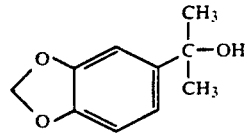

About 600 ml of a 1.5 M solution of methyllithium in ether was added to 500 ml of tetrahydrofuran to obtain a mixture. A suspension of 93.45 g of 5-acetyl-1,3-benzodioxole in 900 ml of tetrahydrofuran was added to the mixture, while keeping it at −20° C. by cooling and the obtained mixture was stirred as such for one hour. Water was added to the reaction mixture and the obtained mixture was extracted with ethyl acetate. The organic layer was washed with a saturated aqueous solution of common salt and dried over anhydrous magnesium sulfate. The resulting mixture was filtered and the filtrate was concentrated to obtain 97 g of the title compound as an oil.

$^1$H-NMR (90MHz, CDCl$_3$) δ;
1.54(s,6H), 1.72(bs,1H), 5.88(s,2H), 6.6~7.0(m,3H)

Preparative Example 2

2-(1,3-Benzodioxol-5-yl)propene

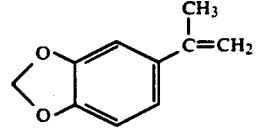

14.52 g of 2-(1,3-benzodioxol-5-yl)-2-propanol was dissolved in 200 ml of benzene, followed by the addition of a catalytic amount of p-toluenesulfonic acid monohydrate. The obtained mixture was heated under reflux in a short-neck Kjeldahl flask fitted with a Dean-Stark reflux condenser for 2.5 hours. The reaction mixture was washed with a saturated aqueous solution of sodium hydrogencarbonate and a saturated aqueous solution of common salt successively, dried over anhydrous magnesium sulfate and filtered. The filtrate was concentrated to obtain 14.33 g of the title compound as an oil.

$^1$H-NMR (90MHz, CDCl$_3$) δ; 2.08(bs,3H), 4.8~5.0(m,1H), 5.19(bs, 1H), 5.89(s,2H), 6.5~7.0(m,3H)

Preparative Example 3

1-(6-Methyl-1,3-benzodioxol-5-yl)ethanol

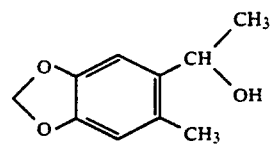

32 ml of a 1.4 M solution of methyllithium in diethyl ether was dissolved in 50 ml of anhydrous tetrahydrofuran. The obtained solution was cooled to −40° C. in a nitrogen atmosphere, followed by the addition of 5.0 g of solid (6-methyl-1,3-benzodioxol-5-yl)carboxaldehyde. The mixture was heated to a room temperature over a period of one hour, followed by the addition of water. The obtained mixture was extracted with ether and the obtained organic layer was washed with an aqueous solution of common salt, dried over magnesium sulfate and distilled to remove the solvent. The obtained white solid was recrystallized from diisopropyl ether/n-hexane to obtain 2.8 g of the title compound as a colorless crystal.

m.p.: 61° to 62° C.
$^1$H-NMR (90MHz, CDCl$_3$) δ;
1.39(d,J=7Hz,3H), 1.72(bs,1H), 2.22(s, 3H), 4.99(m,1H), 5.83(s,2H), 6.53(s,1H), 6.94(s,1H)

Preparative Example 4

1-(6-Methyl-1,3-benzodioxol-5-yl)-1-propanol

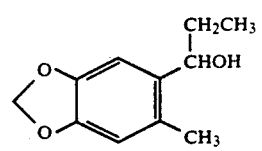

A solution of 2.0 g of (6-methyl-1,3-benzodioxol-5-yl)-carboxaldehyde in 15 ml of anhydrous tetrahydrofuran was dropwise added at a room temperature to a Grignard reagent prepared from 0.32 g of magnesium ribbon, 20 ml of anhydrous tetrahydrofuran and 1.4 g of bromoethane, followed by stirring for 2 hours. A saturated aqueous solution of ammonium chloride was added to the reaction mixture and the obtained mixture was distilled to remove the solvent. The residue was extracted with ethyl acetate and the organic layer was dried over magnesium sulfate and concentrated in a vacuum. The residue was purified by silica gel column chromatography (ethyl acetate/hexane=2:8) to obtain 2.27 g of the title compound as a colorless crystal.

m.p.: 71° to 72° C.
$^1$H-NMR (90MHz, CDCl$_3$) δ;
0.92(t,J=7Hz,3H), 1.68~1.92(m,2H), 1.80(bs,1H), 2.20(s,3H), 4.72(t,J=7Hz, 1H), 5.82(s,2H), 6.52(s,1H), 6.88(s,1H)

Preparative Example 5

1-(6-Ethyl-1,3-benzodioxol-5-yl)-1-propanol

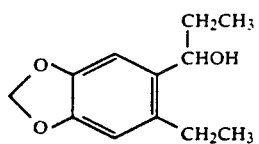

A solution of 3.2 g of (6-ethyl-1,3-benzodioxol-5-yl)-carboxaldehyde in 10 ml of anhydrous tetrahydrofuran was dropwise added at a room temperature to a Grignard reagent prepared from 0.54 g of magnesium ribbon, 10 ml of anhydrous tetrahydrofuran and 2.4 g of bromoethane to carry out the reaction at the same temperature for 2 hours. A saturated aqueous solution of ammonium chloride was added to the reaction mixture. The obtained mixture was distilled to remove the solvent and the residue was extracted with ethyl acetate. The organic layer was dried over magnesium sulfate and concentrated in a vacuum to obtain 3.9 g of a crude alcohol as a yellow oil. This oil was used as such in the subsequent reactions.

$^1$H-NMR (90MHz, CDCl$_3$) δ;
0.96(t,J=7Hz,3H), 1.18(t,J32 7Hz,3H), 1.72(m,3H), 2.32~2.80(m,2H), 4.76(t,J=7Hz,1H), 5.84(s,2H), 6.58(s,1H), 6.88(s,1H)

Preparative Example 6

2-(1,3-Benzodioxol-5-yl)-2-butanol

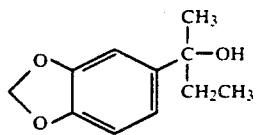

15 ml of tetrahydrofuran and a catalytic amount of iodine were added to 340 mg of magnesium ribbon to obtain a mixture. 1.59 g of bromoethane was gradually added to the mixture in a stream of nitrogen in such a way that the reaction system was mildly refluxed. The resulting mixture was heated under reflux for 30 minutes and cooled, followed by the addition of a solution of 2 g of 5-acetyl-1,3-benzodioxole in tetrahydrofuran. The obtained mixture was stirred at a room temperature for 20 minutes, followed by the addition of a saturated aqueous solution of ammonium chloride and water. The obtained mixture was extracted with ethyl acetate. The organic layer was washed with a saturated aqueous solution of common salt, dried over anhydrous magnesium sulfate and filtered. The filtrate was distilled to remove the solvent. 2.27 g of the title compound was obtained as a crude oil.

Preparative Example 7

5-Chloromethyl-6-isopropyl-1,3-benzodioxole

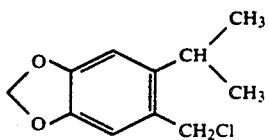

A mixture comprising 30 g of 37% formalin, 13 ml of concentrated hydrochloric acid and 100 ml of ethyl acetate was heated to 55° C., while passing hydrochloric acid gas through the mixture. A solution of 7.5 g of 5-isopropyl-1,3-benzodioxole in 20 ml of ethyl acetate was dropwise added to the resulting mixture and the obtained mixture was stirred as such for 2.5 hours and cooled, followed by the addition of benzene. The obtained mixture was washed with water, dried over anhydrous magnesium sulfate and filtered. The filtrate was concentrated to obtain 10.22 g of the title compound as a crude oil.

$^1$H-NMR(90MHz, CDCl$_3$) δ;
1.18(d,J=7.2Hz,6H), 3.31(sept,J=7.2Hz,1H), 5.88(s,2H), 6.70(s,1H), 6.91(s,1H)

Preparative Example 8

5-Bromo-6-isopropyl-1,3-benzodioxole

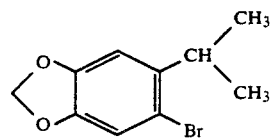

2.94 g of 5-isopropyl-1,3-benzodioxole was dissolved in 30 ml of carbon tetrachloride to obtain a solution. A solution of 3.15 g of bromine in 5 ml of carbon tetrachloride was dropwise added to the solution at a temperature of −5° to 5° C. The obtained mixture was stirred at 10° C. for 8.5 hours. Nitrogen gas was passed through the resulting mixture, followed by the addition of a saturated aqueous solution of sodium hydrogencarbonate and an aqueous solution of sodium thiosulfate. The obtained mixture was extracted with chloroform and the organic layer was washed with a saturated aqueous solution of common salt, dried over anhydrous sodium sulfate and filtered. The filtrate was concentrated to obtain 4.38 g of the title compound as a crude oil.

$^1$H-NMR(90MHz, CDCl$_3$) δ;
1.18(d,J=7.2Hz,6H), 3.31(sept,J=7.2Hz,1H), 5.88(s,2H), 6.70(s,1H), 6.91(s,1H)

Preparative Example 9

5-(6-Isopropyl-1,3-benzodioxole)carboxaldehyde

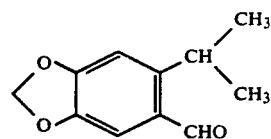

7.8 ml of a 1.6 M solution of n-butyllithium in hexane was added to a solution of 2.34 g of 5-bromo-6-isopropyl-1,3-benzodioxole (crude oil) in 50 ml of anhydrous ether at −40° C. The obtained mixture was heated to −10° C. and cooled again to −50° C, followed by the addition of 4.48 ml of N,N-dimethylformamide. The obtained mixture was heated under stirring to raise the temperature thereof to 0° C. slowly. Then, the resulting mixture was acidified with 1 N hydrochloric acid, stirred for 30 minutes and extracted with ethyl acetate. The organic layer was washed with a saturated aqueous solution of common salt, dried over anhydrous magnesium sulfate and filtered. The filtrate was distilled to remove the solvent. The residue was purified by silica

Preparative Example 10

α-(6-Isopropyl-1,3-benzodioxol-5-yl)benzyl alcohol

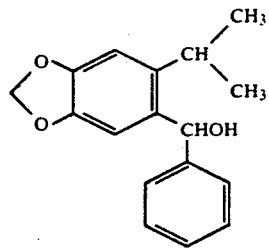

8.1 ml of a 2.0 M solution of phenyllithium in a cyclohexane/diethyl ether (7:3) mixture was added to a solution of 2.08 g of 5-(6-isopropyl-1,3-benzodioxol-5-yl)carboxaldehyde in anhydrous ether at −60° C. The obtained mixture was stirred overnight in such a way that the temperature thereof rose to a room temperature slowly. Ice/water was added to the resulting mixture and the obtained mixture was extracted with ethyl acetate. The organic layer was washed with a saturated aqueous solution of common salt, dried over anhydrous magnesium sulfate and filtered. The filtrate was distilled to remove the solvent. The residue was purified by silica gel column chromatography (ethyl acetate/hexane=2:98) to obtain 2.49 g of the title compound as a colorless prismatic crystal.

$^1$H-NMR(90MHz, CDCl$_3$) δ;
1.03(d,J=6.8Hz,3H), 1.18(d,J=6.8Hz,3H), 2.03(d,J=1.8Hz,1H), 3.18(m,1H), 5.86(s,2H), 6.05(d,J=1.8Hz,1H), 6.72(s,1H), 6.84(s,1H), 7.05~7.4(m,5H)

Preparative Example 11

5-Cyanomethyl-6-isopropyl-1,3-benzodioxole

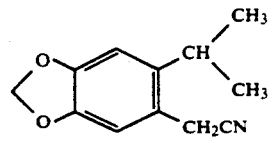

6.9 g of 5-chloromethyl-6-isopropyl-1,3-benzodioxole was dissolved in 100 ml of dimethyl sulfoxide, followed by the addition of 3.12 g of sodium cyanide. The obtained mixture was stirred at a room temperature for 3 hours and distilled to remove the solvent. Ethyl acetate was added to the residue and the obtained mixture was washed with water and a saturated aqueous solution of common salt successively, dried over anhydrous magnesium sulfate and filtered. The filtrate was concentrated to obtain 6.26 g of the title compound as a crude oil.

$^1$H-NMR(90MHz, CDCl$_3$) δ;
1.21(d,J=7.2Hz,6H), 2.96(sept,J=7.2Hz,1H), 3.60(s,2H), 5.88(s,2H), 6.73(bs,2H)

gel column chromatography (hexane) to obtain 1.40 g of the title compound as a colorless oil.

$^1$H-NMR(90MHz, CDCl$_3$) δ;
1.28(d,J=6.5Hz,6H), 3.84(sept,J=6.5Hz,1H), 5.96(s,2H), 6.81(s,1H), 7.23(s,1H)

Preparative Example 12

(6-Isopropyl-1,3-benzodioxol-5-yl)acetic acid

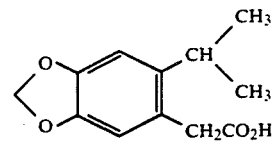

6.22 g of 5-cyanomethyl-6-isopropyl-1,3-benzodioxole (crude oil) was dissolved in 120 ml of ethanol, followed by the addition of 40 ml of water and 12.24 g of sodium hydroxide. The obtained mixture was stirred for 20 hours, while keeping the temperature of an oil bath at 100° C. The reaction mixture was concentrated, followed by the addition of water. The obtained mixture was washed with ethyl acetate. The aqueous layer was acidified with concentrated hydrochloric acid and extracted with chloroform. The organic layer was washed with a saturated aqueous solution of common salt, dried over anhydrous magnesium sulfate and filtered. The filtrate was concentrated to obtain 6.31 g of the title compound as a crude crystal.

$^1$H-NMR(90MHz,CDCl$_3$) δ;
1.17(d,J=6.5Hz,6H), 2.99(sept,J=6.5Hz,1H), 3.58(s,2H), 5.85(s,2H), 6.60(s,1H), 6.72(s,1H)

Preparative Example 13

2-(6-Isopropyl-1,3-benzodioxol-5-yl)ethanol

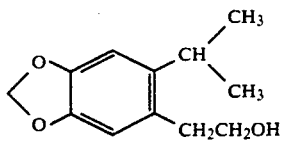

A solution of 6.25 g of (6-isopropyl-1,3-benzodioxol-5-yl)acetic acid (crude crystal) in 30 ml of tetrahydrofuran was dropwise added to a suspension of 1.6 g of lithium aluminum hydride in 40 ml of tetrahydrofuran under cooling with ice. The obtained mixture was stirred overnight. 1.6 ml of water, 1.6 ml of a 15% aqueous solution of sodium hydroxide and 4.8 ml of water were added to the resulting mixture successively under cooling with ice. The obtained mixture was filtered and the filtrate was concentrated. The residue was purified by silica gel column chromatography to obtain 4.51 g of the title compound as a colorless oil.

$^1$H-NMR(90MHz,CDCl$_3$) δ;
1.19(d,J=6.8Hz,6H), 1.3~1.6(br,1H), 2.82(t,J=6.8Hz,2H), 3.10(sept,J=6.8Hz,1H), 3.5~3.9((br,2H), 5.84(s,2H), 6.59(s,1H), 6.72(s,1H)

Preparative Example 14

(6-Benzyl-1,3-benzodioxol-5-yl)acetic acid

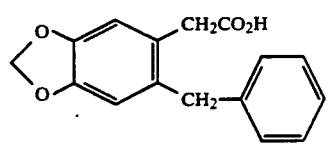

6.0 g of 5-benzyl-1,3-benzodioxole was dissolved in 100 ml of ethyl acetate to obtain a solution. This solution was dropwise added at 55° C. to a mixture comprising 10 ml of concentrated hydrochloric acid, 20 ml of ethyl acetate and 22 g of 37% formalin into which hydrogen chloride gas had been bubbled. The reaction was carried out at the same temperature for 1.5 hours. The reaction mixture was washed with water four times, dried over magnesium sulfate and cencentrated in a vacuum to obtain 10.6 g of a crude chloro derivative as a pale yellow oil.

7.1 g of the crude chloro derivative (unpurified) was dissolved in 50 ml of dimethyl sulfoxide, followed by the addition of 2.0 g of well-ground sodium cyanide. The reaction was carried out for 2 hours. Water was added to the reaction mixture, followed by the extraction with chloroform. The organic layer was washed with water twice, dried over magnesium sulfate and concentrated in a vacuum to obtain 4.4 g of a crude cyano derivative as a yellow oil.

This cyano derivative and 7 g of sodium hydroxide were dissolved in a mixture comprising 20 ml of ethanol and 20 ml of water. The obtained solution was heated under reflux for 20 hours. After the completion of the reaction, the reaction mixture was distilled in a vacuum to remove the ethanol, followed by the addition of 200 ml of water. The obtained mixture was washed with ether. The aqueous layer was acidified with 6 N hydrochloric acid and extracted with chloroform. The organic layer was washed with a saturated aqueous solution of common salt, dried over magnesium sulfate and concentrated in a vacuum to obtain a brown solid. This solid was recrystallized from ethyl acetate to obtain 1.83 g of the title compound as a pale yellow needle.

m.p.: 116° to 117° C.
$^1$H-NMR(90MHz,CDCl$_3$) δ;
3.48(s,2H), 3.88(s,2H), 5.86(s,2H),
6.56(s,1H), 6.64(s,1H), 6.80~7.40(m, 5H), 8.40~10.0(bs,1H)

Preparative Example 15

2-(6-Benzyl-1,3-benzodioxol-5-yl)ethanol

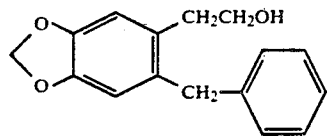

A solution of 1.82 g of (6-benzyl-1,3-benzodioxol-5-yl)acetic acid in 22 ml of anhydrous tetrahydrofuran was dropwise added at 0° C. to a suspension of 0.38 g of lithium aluminum hydride in anhydrous tetrahydrofuran. The obtained mixture was warmed to a room temperature to carry out the reaction for 4 hours, followed by the addition of water. The mixture was filtered to remove the precipitate. The filtrate was concentrated in a vacuum to obtain a yellow oil residue. This residue was purified by silica gel column chromatography (ethyl acetate/hexane=2:8) to obtain 1.42 g of the title compound as a colorless crystal.

m.p.: 64° to 65° C.
$^1$H-NMR(90MHz,CDCl$_3$) δ;
2.76(t,J=7Hz,2H), 3.64(m,2H), 3.90(s, 2H), 5.86(s,2H), 6.56(s,1H), 6.66(s,1H), 6.80~7.34(m,5H)

Example 1

[{1-(1,3-Benzodioxol-5-yl)butyl}thio3acetic acid

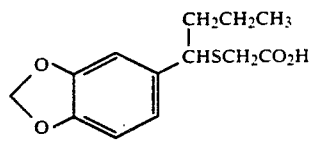

A mixture comprising 103 g of 1-(1,3-benzodioxol-5-yl)-1-butanol, 73.3 g of mercaptoacetic acid, 0.1 g of D-10-camphorsulfonic acid and 500 ml of benzene was heated under reflux for 2 hours, followed by the addition of 2000 ml of ether. The obtained mixture was washed with water and extracted with 750 ml and then 100 ml of 1 N sodium hydroxide successively. The extracts were combined, washed with ether and chloroform successively, acidified with concentrated hydrochloric acid and extracted with ethyl acetate (800 ml and 400 ml). The extracts were combined, washed with water, dried over magnesium sulfate and concentrated in a vacuum to obtain 132 g of a crude product. This crude product was purified by silica gel chromatography (ethyl acetate/hexane/formic acid =100:900:1) to obtain 127 g of a colorless oil. This oil was crystallized from n-hexane to obtain 115 g of the title compound as a white crystalline powder.

m.p.: 59° to 61° C.
$^1$H-NMR(90MHz,CDCl$_3$) δ;
0.88(m,3H), 1.12~1.52(m,2H), 1.78~1.94(m,2H), 2.92 and 3.03(ABq,J=15Hz, 2H), 3.92(t,J=7Hz,1H), 5.92(s,2H), 6.68~6.80(m,3H)

Example 2

[{1-(1,3-Benzodioxol-5-yl)-1-methylethyl}thio]acetic acid

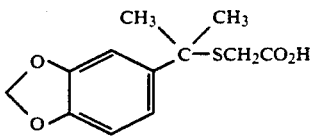

600 ml of benzene, 59.5 g of mercaptoacetic acid and a catalytic amount of D-10-camphorsulfonic acid were added to 97 g of 2-(1,3-benzodioxol-5-yl)-2-propanol. The obtained mixture was heated under reflux for 4 hours and distilled to remove the solvent. The pH of the residue was adjusted to 10 with a 1N aqueous solution of sodium hydroxide. The resulting mixture was washed with ethyl acetate. 4N hydrochloric acid was added to the mixture under cooling with ice to acidify the aqueous layer. The resulting mixture was extracted with chloroform. The organic layer was washed with water, dried over anhydrous magnesium sulfate and filtered. The filtrate was concentrated to obtain a crude crystal. This crude crystal was recrystallized from diisopropyl ether to obtain 62.70 g of the title compound as a colorless crystal.

The above procedure was repeated except that 38.73 g of 2-(1,3-benzodioxol-5-yl) propene was used instead of the corresponding propanol to obtain 37.32 g of the title compound.

m.p.: 78.5° to 80° C.
$^1$H-NMR(90MHz,CDCl$_3$) δ;

1.68(s,6H), 2.99(s,2H), 5.88(s,2H),
6.64(d,J=8.3Hz,1H), 6.86(dd,J=8.3Hz,
2.5Hz,1H), 6.99(d,J=2.5Hz,1H), 8.0~
9.0(br,1H)

Example 3

[{1-(6-Methyl-1,3-benzodioxol-5-yl)ethyl}thio]acetic acid

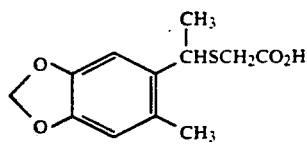

3.7 g of mercaptoacetic acid and a catalytic amount of D-10-camphorsulfonic acid were added to 3.2 g of 1-(6-methyl-1,3-benzodioxol-5-yl)ethanol, followed by the addition of 100 ml of benzene. The obtained mixture was heated under reflux for one hour, washed with water and extracted with a 1N aqueous solution of sodium hydroxide. The aqueous layer was washed with ethyl acetate, acidified with 1 N hydrochloric acid and extracted with chloroform. The organic layer was dried over magnesium sulfate and distilled to remove the solvent. The obtained crystalline residue was recrystallized from diisopropyl ether to obtain 4.2 g of the title compound as a colorless crystal.

m.p.: 93.5° to 94.5° C.
$^1$H-NMR(90MHz,CDCl$_3$) δ;
1.51(d,J=7Hz,3H), 2.26(s,3H), 2.92 and
3.12(ABq,J=16Hz,2H), 4.39(q,J=7Hz,1H),
5.85(s,2H), 6.54(s,1H), 6.94(s,1H),
10.12(m,1H)

Example 4

[{1-(6-Methyl-1,3-benzodioxol-5-yl)propyl}thio]acetic acid

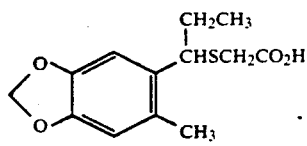

2.27 g of 1-(6-methyl-1,3-benzodioxol-5-yl)-1propanol, 0.1 g of p-toluenesulfonic acid and 1.52 g of mercaptoacetic acid were dissolved in 80 ml of benzene to obtain a solution. This solution was heated under reflux for 12 hours, while removing generated water. The reaction mixture was poured into water. The aqueous layer was basified and washed with ether. The aqueous layer was acidified and extracted with chloroform. The organic layer was washed with water, dried over magnesium sulfate and concentrated in a vacuum to obtain a pale yellow solid. This solid was purified by silica gel column chromatography (ethyl acetate/hexane=2:8) to obtain 2.83 g of the title compound as a white crystal.

m.p.: 98° to 99° C.
$^1$H-NMR(90MHz,CDCl$_3$) δ;
0.88(t,J=7Hz,3H), 1.60~2.12(m,2H), 2.24(s,3H),
2.96 and 3.08(ABq,J=14Hz,2H),
4.26(dd,J=9Hz,7Hz,1H), 5.92(s,2H), 6.62 (s,1H),
6.98(s,1H)

Example 5

[{1-(6-Ethyl-1,3-benzodioxol-5-yl)propyl}thio]acetic acid

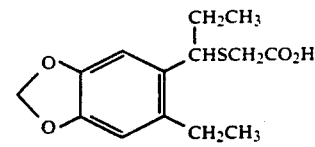

4.0 g of ethyl [{1-(6-ethyl-1,3-benzodioxol-5-yl)propyl}thio]acetate and 2.6 g of sodium hydroxide were dissolved in a mixture comprising 20 ml of water and 20 ml of ethanol. The obtained solution was heated under reflux for 2 hours and distilled to remove the ethanol. The residue was washed with ether. The aqueous layer was acidified and extracted with chloroform. The extract was washed with water, dried over magnesium sulfate and concentrated in a vacuum. The residue was purified by silica gel column chromatography (ethyl acetate/hexane=2:8) to obtain 2.8 g of the title compounds as a colorless crystal.

m.p 88° to 89° C.
$^1$H-NMR(90MHz,CDCl$_3$) δ; 0.92(t,J=7Hz,3H),
1.16(t,J=7Hz,3H), 1.56~2.12(m,2H),
2.24~2.76(m,2H), 2.95 and 3.08(ABq,J=16Hz,2H),
4.20(t,J=7Hz,1H), 5.88(s,2H), 6.58(s,1H), 6.90 (s,1H),
9.72(bs,1H)

Example 6

[{(6-Methyl-1,3-benzodioxol-5-yl)methyl}thio]acetic acid

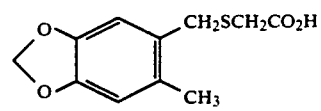

A suspension of 6.0 g of 5-chloromethyl-6-methyl-1,3-benzodioxole, 6.0 g of mercaptoacetic acid and 6.5 g of sodium hydroxide in 130 ml of 50% aqueous ethanol was heated under reflux for one hour and concentrated, followed by the addition of water. The mixture was washed with ethyl acetate. The aqueous layer was acidified with 1N hydrochloric acid and extracted with chloroform. The organic layer was dried over magnesium sulfate and distilled to remove the solvent. The residue was chromatographed over a silica gel column and eluted with chloroform to obtain a crude crystal. This crude crystal was recrystallized from diisopropyl ether to obtain 1.6 g of the title compound as a colorless crystal.

m.p.: 90° to 92° C.
$^1$H-NMR(90MHz,CDCl$_3$) δ;
2.30(s,3H), 3.14(s,2H), 3.76(s,2H),
5.86(s,2H), 6.60(s,1H), 6.70(s,1H)

Example 7

[{1-(1,3-Benzodioxol-5-yl)-2-methylpropyl}thio]acetic acid

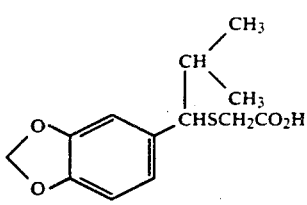

A mixture comprising 2 g of 1-(1,3-benzodioxol-5-yl)-2-methyl-1-propanol, 1.3 g of mercaptoacetic acid, a catalytic amount of p-toluenesulfonic acid and 50 ml of benzene was heated under reflux for 5.5 hours, followed by the addition of ethyl acetate. The mixture was washed with water and extracted with a 2N aqueous solution of sodium hydroxide. The aqueous layer was washed with chloroform, acidified with dilute hydrochloric acid and extracted with ethyl acetate. The extract was washed with water, drided over anhydrous magnesium sulfate and concentrated in a vacuum to obtain a residue. This residue was purified by silica gel column chromatography (chloroform/methanol =20:1) to obtain 2.14 g of the title compound as a colorless oil.

$^1$H-NMR(90MHz,CDCl$_3$) δ;
0.81(d,J=7.0Hz,3H), 1.09(d,J=7.0Hz,3H), 1.80~2.23(m,1H), 2.88 and 3.01(ABq,J= 15.1Hz,2H), 3.73(d,J=9.0Hz,1H), 5.89(s, 2H), 6.61-6.89(m,3H), 8.18~8.69(bs, 1H)

Example 8

Sodium [{1-(1,3-benzodioxol-5-yl)-2-methylpropyl}thio]acetate

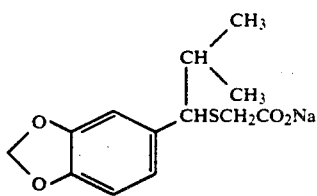

3.99 ml of a 2N aqueous solution of sodium hydroxide was added to 2.14 g of [{1-(1,3-benzodioxol-5-yl)-2-methyl-1-propyl}thio]acetic acid to obtain a solution, followed by the addition of ethanol. The mixture was distilled to remove the solvent. Ether was added to the obtained residue to generate a precipitate. This precipitate was separated by filtration and dried to obtain 2.2 g of the title compound as a white powder.

m.p.: 243° to 250° C. (decomp.)
$^1$H-NMR(90MHz, DMSO-d$_6$) δ;
0.75(d,J=7.0Hz,3H), 1.01(d,J=7.0Hz,3H), 1.61~2.221 (m,1H), 2.62 and 2.70(ABq,J= 13.5Hz,2H), 3.63(d,J=8.3Hz,1H), 5.97(s, 2H), 6.50~7.02(m,3H)
MS(FAB) m/z; 313(MNa$^-$)

Example 9

[{1-(1,3-Benzodioxol-5-yl)pentyl}thio]acetic acid

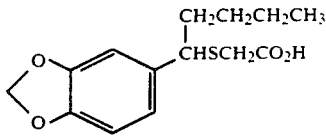

2.0 g of the title compound was obtained as a colorless oil from 2g of 1-(1,3-benzodioxol-5-yl)-1-pentanol according to the same procedure as that described in Example 7.

$^1$H-NMR(90MHz,CDCl$_3$) δ; 0.70~0.98(m,3H), 1.04~1.54(m,4H), 1.60~2.02(m,2H), 2.90 and 3.02(ABq,J= 14.4Hz,2H), 3.88(t,J=7Hz,1H), 5.90(s, 2H), 6.62~6.90(m,3H), 6.62~7.34(bs, 1H)

Example 10

Sodium [{1-(1,3-benzodioxol-5-yl)pentyl}thio]acetate

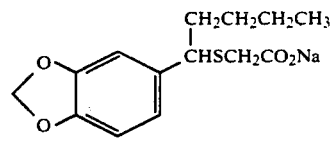

1.9 g of the title compound was prepared from 2.0 g of [{1-(1,3-benzodioxol-5-yl)pentyl}thio]acetic acid as a white power according to the same procedure as that described in Example 8.

m.p.: 232° to 242° C. (decomp.)
$^1$H-NMR(90MHz, DMSO-d$_6$) δ;
0.62~0.80(m,3H), 0.94~1.38(m,4H), 1.54~1.88(m,2H), 2.67 and 2.75(ABq,J= 13.3Hz,2H), 3.83(t,J=7.0Hz,1H), 5.97(s, 2H), 6.60~6.90(m,3H)
MS (FAB) m/z; 327(MNa$^-$)

Example 11

[{1-(L,3-Benzodioxol-5-yl)-1-methylpropyl}thio]acetic acid

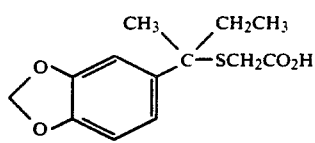

50 ml of benzene, 1.29 g of mercaptoacetic acid and a catalytic amount of p-toluenesulfonic acid - monohydrate were added to 2.27 g of 2-(1,3-benzodioxol-5-yl)-2-butanol (crude oil). The obtained mixture was heated under reflux for 11 hours and cooled, followed by the addition of benzene. The obtained mixture was washed with water, followed by the addition of a 1N aqueous solution of sodium hydroxide. The alkaline layer was separated, washed with ethyl acetate, acidified with concentrated hydrochloric acid and extrated with chloroform. The organic layer was washed with water, dried over anhydrous magnesium sulfate and filtered. The filtrate was distilled to remove the solvent. The residue was purified by silica gel column chromatography (chloroform) to obtain 1.11 g of the title compound as a colorless oil.

$^1$H-NMR(90MHz,CDCl$_3$) δ: 0.82(d,J=7.2Hz,3H), 1.66(s,3H), 1.7~2.1(m,2H), 5.90(s,2H), 6.65(d,J=7.9Hz, 1H), 6.82(dd,J=7.9Hz and 1.8Hz,1H), 6.96(d,J=1.8Hz,1H), 7.4~8.6(br,1H)

Example 12

Sodium [{1-(1,3-benzodioxol-5-yl)-1-methylpropyl}thio]acetate

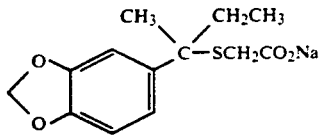

1.00 g of the title compound was obtained from 1.04 g of [{1-(1,3-benzodioxol-5-yl)-1-methylpropyl}thio]acetic acid as a white powder according to the same procedure as that described in Example 8.

m.p.: >280° C.

$^1$H-NMR(90MHz, DMSO-d$_6$) δ; 0.72(bt,J=7.2Hz,3H), 1.52(s,3H), 1.6~2.1(m,2H), 2.70(ABq,J=13.3Hz, Δν=20.5), 5.97(s,2H), 6.5~7.1(m,3H)

MS(FAB) m/z; 313(MNa$^-$), 291(MH$^-$)

Example 13

[[1-{1-(1,3-Benzodioxol-5-yl)-2-phenyl}ethyl]thio]acetic acid

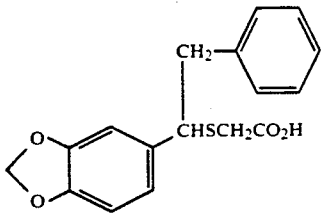

5.5 g of the title compound was obtained from as a colorless needle according to the same procedure as that described in Example 7.

m.p.: 99° to 100° C.

$^1$H-NMR(90MHz,CDCl$_3$) δ; 2.92 and 3.04(ABq,J=14.4Hz,2H), 2.88~3.36(m,2H), 4.20(t,J=7.2Hz,1H), 5.90(s, 2H), 6.48~6.76(m,2H), 6.84(s,1H), 6.88~7.36(m,5H), 9.50~10.00(br,1H)

Example 14

Sodium [[1-{1-(1,3-benzodioxol-5-yl)-2-phenyl}ethyl]thio]acetate

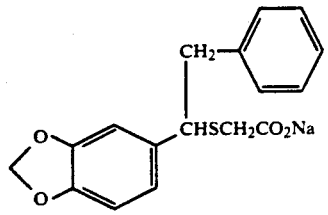

1.7 g of the title compound was obtained from 2.0 g of [[1-{1-(1,3-benzodioxol-5-yl)-2-phenyl}ethyl]thio]acetic acid as a white powder according to the same procedure as that described in Example 8.

m.p.: 201° to 215° C. (decomp.)

$^1$H-NMR(90MHz,CDCl$_3$) δ; 12.71 and 2.79(ABq,J=13.9Hz,2H), 3.00 (dd,J=9.2Hz and 13.7Hz,1H), 3.12(dd,J=6.2Hz and 13.9Hz,1), 4.19(dd,J=6.2Hz and 9.5Hz,1H), 5.95(m,2H), 6.64(dd,J=1.5Hz and 8.1Hz,1H), 6.72(d,J=7.7Hz,1H), 6.865(d,J=1.8Hz,1H), 7.08~7.19(m,5H)

MS(FAB) m/z;339(MH$^-$)

Example 15

[{1-(6-Methyl-1,3-benzodioxol-5-yl)butyl}thio]acetic acid

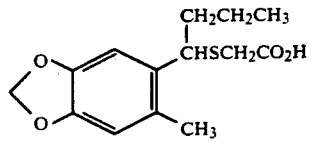

A solution of 5.0 g of (6-methyl-1,3-benzodioxol-5-yl)-carboxaldehyde in 20 ml of tetrahydrofuran was dropwise added at a room temperature to a Grignard reagent prepared from 0.86 g of magnesium ribbon, 10 ml of tetrahydrofuran and 4.4 g of 1-bromopropane. The obtained mixture was stirred at a room temperature for one hour, followed by the addition of a saturated aqueous solution of ammonium chloride The obtained mixture was extracted with ether. The organic layer was washed with an aqueous solution of common salt, dried over magnesium sulfate and distilled to remove the solvent. 5.6 g of (6-methyl-1,3-benzodioxol-5-yl)-butan-1-ol was obtained.

m.p.: 65.5° to 66.5° C. (isopropyl ether/petroleum ether)

$^1$H-NMR(90MHz,CDCl$_3$) δ; 0.92(m,3H), 1.16~1.80(m,5H), 2.21(s, 3H), 4.83(m,1H), 5.85(s,2H), 6.55(s,1H), 6.92(s,1H)

This product was used in the following reaction without being purified.

A solution of 5.6 g of (6-methyl-1,3-benzodioxol-5-yl)butan-1-ol, 4.8 g of mercaptoacetic acid and a catalytic amount of D-10-camphorsulfonic acid in 60 ml of benzene was heated under reflux for 3 hours, followed by the addition of ethyl acetate. The obtained mixture was washed with water and extracted with a 1N aqueous solution of sodium hydroxide. The aqueous layer was washed with ethyl acetate, acidified with 1N hydrochloric acid and extracted with chloroform. The organic layer was dried over magnesium sulfate and distilled to remove the solvent. The obtained residue was chromatographed over silica gel column and eluted with chloroform to obtain a colorless crystal. This crystal was recrystallized from isopropyl ether/hexane to obtain 4.1 g of the title compound as a colorless prismatic crystal.

m.p.: 77.5° to 78° C.

$^1$H-NMR(90MHz,CDCl$_3$) δ; 0.88(m,3H), 1.10~1.50(m,2H), 1.60~1.90(m,2H), 2.22(s,3H), 2.89 and 3.05 (ABq,J=16Hz,2H), 4.26(t,J=7Hz,1H), 5.86 (s,2H), 6.52(s,1H), 6.89(s,1H)

Example 16
Sodium [{1-(6-methyl-1,3-benzodioxol-5-yl)butyl}thio3acetate 3.2 g of the title compound was prepared from 3.0 g of [{1-(6-methyl-1,3-benzodioxol-5-yl)butyl}thio]acetic acid as a white powder according to the same procedure as that described in Example 8.

m.p.: 233° to 236° C. (decomp.)
$^1$H-NMR(400MHz,DMSO-d$_6$) δ;
0.82(t,J=7.3Hz,3H), 1.12~1.27(m,2H), 1.58~1.68(m,1H), 1.70~1.79(m,1H), 2.21(s,3H), 2.67 and 2.71(ABq,J=13.9Hz, 2H), 4.15(dd,J=6.2Hz and 8.8Hz,1H), 5.93 (m,2H), 6.67(s,1H), 6.87(s,1H)
MS(FAB) m/z; 327(MNa$^-$), 305(MH$^-$)

Example 17
[{(6-Isopropyl-1,3-benzodioxol-5-yl)methyl}thio]acetic acid

A suspension of 3.3 g of 5-chloromethyl-6-isopropyl-1,3-benzodioxole (crude oil) in 10 ml of ethanol was added to a liquid mixture comprising 2.1 g of mercaptoacetic acid, 3 g of sodium hydroxide, 25 ml of ethanol and 25 ml of water to carry out the reaction at 80° C. for 40 minutes. The reaction mixture was concentrated, followed by the addition of water. The obtained mixture was washed with ethyl acetate. Concentrated hydrochloric acid was added to the mixture to acidify the aqueous layer, followed by the extraction with chloroform. The extract was washed with water, dried over anhydrous magnesium sulfate and filtered. The filtrate was distilled to remove the solvent. The residue was purified by column chromatography to obtain 2.45 g of the title compound as a colorless prismatic crystal.

m.p.: 83° to 84° C.
1.21(d,J=7.2Hz ,6H), 3.16(s,2H), 3.18 (sept,J=7.2Hz,1H), 3.82(s,2H), 5.90(s, 2H), 6.68(s,1H), 6.72(s,1H), 6.6~8.0 (br,1H)

Example 18
Sodium [{(6-isopropyl-1,3-benzodioxol-5-yl)methyl}thio3acetate 2.01 g of the title compound was prepared from 2.03 g of [{(6-isopropyl-1,3-benzodioxol-5-yl)methyl}thio]acetic acid as a white powder according to the same procedure as that described in Example 8.

m.p.: 213° to 215° C. (decomp.)
$^1$H-NMR(90MHz, DMSO-d$_6$) δ;
1.13(d,J=6.8Hz,6H), 2.87(s,2H), 3.20 (sept,J=6.81 Hz,1H), 3.66(s,2H), 5.87(s, 2H), 6.74(s,1H), 6.76(s,1H)
MS(FAB) m/z; 313(MNa$^-$), 291(MH$^-$)

Example 19
{α-(6-Isopropyl-1,3-benzodioxol-5-yl)benzyl}thio]acetic acid 1.2 g of α-(6-isopropyl-1,3-benzodioxol-5-yl)benzyl alcohol was dissolved in 10 ml of benzene, followed by the addition of 490 mg of mercaptoacetic acid and a catalytic amount of p-toluenesulfonic acid monohydrate. The obtained mixture was heated under reflux for one hour and cooled, followed by the addition of benzene. The mixture was washed with water, followed by the addition of a 1N aqueous solution of sodium hydroxide. The alkaline layer was separated, acidified with concentrated hydrochloric acid and extracted with chloroform. The extract was washed with water, dried over anhydrous magnesium sulfate and filtered The filtrate was distilled to remove the solvent. The residue was purified by silica gel column chromatography (hexane/chloroform=3:7) to obtain 1.42 g of the title compound as a colorless prismatic crystal.

m.p.: 113.5° to 114.5° C.
$^1$H-NMR(90MHz,CDCl$_3$) δ;
1.05(d,J=6.8 Hz,3H), 1.22(d,J=7.2Hz,3H), 3.10(s,2H), 3.28(m,1H), 5.73(s,1H), 5.7 ~6.0(m,2H), 6.68(s,1H), 6.98(s,1H), 7.05~7.60(m,5H)

Example 20
Sodium [{α-(6-isopropyl-1,3-benzodioxol-5-yl)benzyl}thio]acetate 1.21 g of the title compound was prepared from o 1.28 g of [{α-(6-isopropyl-1,3-benzodioxol-5-yl)benzyl}thio]acetic acid as a white powder according to the same procedure as that described in Example 8.

m.p.: 199° to 203° C. (decomp.)
$^1$H-NMR(90NHz,DMSO-d$_6$) δ;
0.93(d,J=6.8Hz,3H), 1.14(d,J=6.8Hz,3H),
2.78(s,2H), 3.0~3.7(m,1H), 5.68(s,2H),
5.8~6.05(m,2H), 6.76(s,1H), 6.94(s,
1H), 7.05~7.45(m,5H)
MS(FAB) m/z; 389(MNa$^-$)

Example 21

[{(6-Benzyl-1,3-benzodioxol-5-yl)methyl}thio3acetic acid

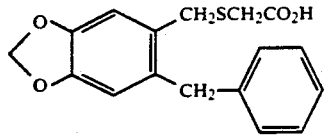

0.93 g of the title compound was prepared from 3.5 g of 6-benzyl-5-chloromethyl-1,3-benzodioxole as a colorless crystal according to the same procedure as that described in Example 17.
m.p.: 99.5° to 100.5° C.
$^1$H-NMR(90MHz,CDCl$_3$) δ;
3.10(s,2H), 3.72(s,2H), 3.98(s,2H),
5.86(s,2H), 6.54(s,1H), 6.76(s,1H),
6.92~7.35(m,5H), 8.00~8.80(br,1H)

Example 22

Sodium [{(6-benzyl-1,3-benzodioxol-5-yl)methyl}thio]acetate

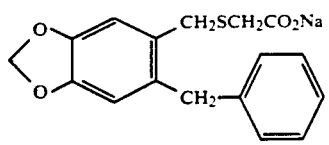

0.95 g of the title compound was prepared from 0.93 g of [{(6-benzyl-1,3-benzodioxol-5-yl)methyl}thio3acetic acid as a white powder according to the same procedure as that described in Example 8.
m.p.: 195° to 205° C. (decomp.)
$^1$H-NMR(400MHz,DMSO-d$_6$) δ;
2.86(s,2H), 3.65(s,2H), 4.00(s,2H),
5.94(s,2H), 6.64(s,1H), 6.87(s,1H),
7.16~7.18(m,3H), 7.25~7.29(m,2H)
MS(FAB) m/z;339(MH$^-$)

Example 23

[{2-(6-Isopropyl-1,3-benzodioxol-5-yl)ethyl}thio]acetic acid

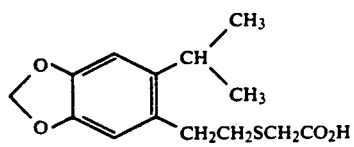

2.41 g of 2-(6-isopropyl-1,3-benzodioxol-5-yl)ethanol was dissolved in 50 ml of methylene chloride, followed by the addition of 3.51 g of triethylamine. 3.31 g of methanesulfonyl chloride was dropwise added to the obtained mixture at −10° C. The obtained mixture was stirred at −10° C. for 40 minutes, followed by the addition of ice/water. The obtained mixture was acidified with 1N hydrochloric acid and extracted with methylene chloride. The extract was washed with water and a saturated aqueous solution of common salt successively, dried over anhydrous magnesium sulfate and filtered. The filtrate was concentrated to obtain a methanesulfonate derivative as a crude oil.

A solution of this derivative in 15 ml of ethanol was dropwise added to a mixture comprising 1.60 g of mercaptoacetic acid, 2.3 g of sodium hydroxide, 15 ml of ethanol and 15 ml of water. The obtained mixture was stirred at 80° to 90° C. for 2 hours and concentrated, followed by the addition of water. The mixture was washed with ethyl acetate, acidified with concentrated hydrochloric acid and extracted with chloroform. The extract was washed with water, dried over anhydrous magnesium sulfate and filtered. The filtrate was distilled to remove the solvent. The residue was purified by silica gel column chromatography (chloroform) to obtain 2.72 g of the title compound as a colorless prismatic crystal.
m.p.: 75.5° to 76° C.
$^1$H-NMR(90MHz,CDCl$_3$) δ;
1.18(d,J=7.2Hz,6H), 2.81(bs,4H), 3.04 (sept,J=7.2Hz, 1H), 3.24(s,2H), 5.83(s, 2H), 6.56(s,1H), 6.69(s,1H), 8.1~9.0 (br,1H)

Example 24

Sodium [{2-(6-isopropyl-1,3-benzodioxol-5-yl)ethyl}thio]acetate

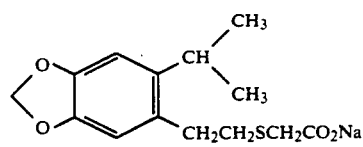

2.45 g of the title compound was prepared from 2.36 g of [{2-(6-isopropyl-1,3-benzodioxol-5-yl)ethyl}thio]acetic acid as a white powder according to the same procedure as that described in Example 8.
m.p.: 213° to 215° C. (decomp.)
$^1$H-NMR(90MHz, DMSO-d$_6$) δ;
1.12(d,J=6.8Hz,6H), 2.45~2.85(m,4H),
2.96(s,2H), 3.04(sept,J=6.8Hz,1H), 5.86
(s,2H), 6.66(s,1H), 6.74(s,1H)
MS(FAB) m/z;327(MNa$^-$), 305(MH$^-$)

Example 25

[{2-(6-Benzyl-1,3-benzodioxol-5-yl)ethyl}thio]acetic acid

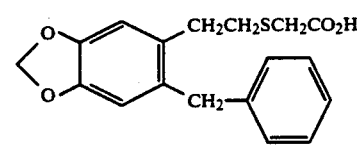

0.93 g of the title compound was prepared from 1.4 g of 2-(6-benzyl-1,3-benzodioxol-5-yl)ethanol as a colorless transparent oil according to the same procedure as that described in Example 23.
$^1$H-NMR(90MHz, CDCl$_3$) δ;
2.44~2.96(m,4H), 3.14(s,2H), 3.90(s, 2H), 5.88(s,2H), 6.56(s,1H), 6.64(s,1H), 6.76~7.36(m,5H)

Example 26

Sodium [{2-(6-benzyl-1,3-benzodioxol-5-yl}ethyl}thio]acetate

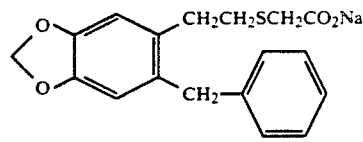

1.0 g of the title compound was prepared from 0.93 g of [{2-(6-benzyl-1,3-benzodioxol-5-yl)ethyl}thio]acetic acid as a white powder according to the same procedure as that described in Example 8.
m.p.: 185° to 205° C. (decomp.)
$^1$H-NMR(400MHz,DMSO-d$_6$) δ;
2.50~2.54(m,2H), 2.66~2.70(m,2H),
2.89(s,1H), 3.90(s,1H), 5.93(s,1H),
6.69(s,1H), 6.80(s,1H), 7.12~7.18(m,3H), 7.25~7.28(m,2H)
MS(FAB) m/z;353(MH$^-$)

Example 27

[{1-(1,3-Benzodioxol-5-yl)-1-methylethyl}thio]acetamide

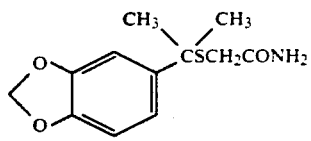

500 mg of [{1-(1,3-benzodioxol-5-yl)-1-methylethyl}thio]acetic acid was dissolved in 10 ml of benzene, followed by the addition of 0.79 ml of thionyl chloride. The obtained mixture was stirred at a room temperature for 15 hours and distilled to remove the solvent. 3.5 ml of tetrahydrofuran was added to the residue. The obtained mixture was dropwise added to 30 ml of aqueous ammonia. The mixture was stirred at a room temperature for 30 minutes and extracted with chloroform. The extract was washed with a saturated aqueous solution of common salt, dried over anhydrous magnesium sulfate and filtered. The filtrate was distilled to remove the solvent. The residue was purified by silica gel column chromatography (ethyl acetate/hexane =4:6) to obtain 240 mg of the title compound as a colorless needle.
m.p.: 70° to 71.5° C.
$^1$H-NMR(90MHz, CDCl$_3$) δ;
1.67(s,6H), 2.95(s,2H), 5.2~5.7(bs,1H),
5.90(s,2H), 6.2~6.7(bs,1H), 6.68(d,J=7.9Hz,1H), 6.87(dd,J=7.9Hz and 1.8Hz,1H), 6.99(d,J=1.8Hz,1H)
MS(FAB) m/z; 507(2MH$^-$),254(MH$^-$)

Example 28

N-Methyl-[{1-(1,3-benzodioxol-5-yl)butyl}thio]acetamide

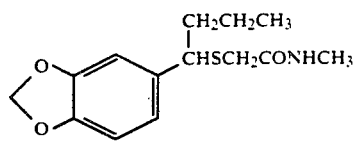

2.5 g of the title compound was prepared from 2.7 g of [{1-(1,3-benzodioxol-5-yl)butyl}thio]acetic acid by using a 40% aqueous solution of methylamine as a colorless oil according to the same procedure as that described in Example 27.
$^1$H-NMR(90MHz, CDCl$_3$) δ;
0.87(m,3H), 1.10~1.50(m,2H), 1.67~1.93(m,2H), 2.72(d,J=5Hz,3H), 3.00(s,2H), 3.62(t,J=1H), 5.88(s,2H),
6.50~6.73(m,3H), 6.58(m,1H)
MS m/z;281(M$^-$)

Example 29

[{1-(1,3-Benzodioxol-5-yl)butyl}thio]acetamide

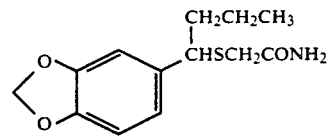

1.8 g of the title compound was prepared from 2.7 g of [{1-(1,3-benzodioxol-5-yl)butyl}thio]acetic acid as a white powder according to the same procedure as that described in Example 27.
m.p.: 91° to 92° C. (ethyl acetate/isopropyl ether)
$^1$H-NMR(90MHz, CDCl$_3$) δ;
0.88(m,3H), 1.11~1.50(m,2H), 1.68~1.94(m,2H), 2.93 and 3.02(ABq,J=17Hz,2H), 3.68(t,J=7Hz,1H), 5.46(brs,1H),
5.89(s,2H), 6.45(brs,1H), 6.52~6.75 (m,3H)
MS m/z; 267(M$^-$)

Example 30

[{1-(6-Methyl-1,3-benzodioxol-5-yl)ethyl}thio]acetamide

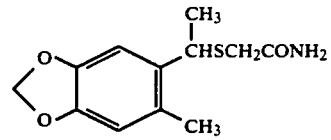

1.5 g of the title compound was prepared from 2.6 g of [{1-(6-methyl-1,3-benzodioxol-5-yl)ethyl}thio]acetic acid as a white powder according to the same procedure as that described in Example 27.
m.p.: 121° to 122° C.
$^1$H-NMR(90MHz, CDCl$_3$) δ;
1.53(d,J=7Hz,3H), 2.22(s,3H), 2.93 and 3.05(ABq,J=16Hz,2H), 4.21(q,J=7Hz,1H),
5.68(brs,1H), 5.85(s,2H), 6.50(brs,1H),
6.53(s,1H), 6.87(s,1H)
MS m/z;253(M$^-$)

Example 31

[{2-(6-Ethyl-1,3-benzodioxol-5-yl)ethyl}thio]acetamide

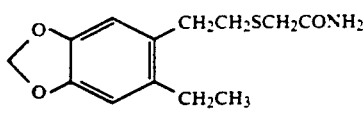

1.1 g of the title compound was prepared from 2.0 g of [{2-(6-ethyl-1,3-benzodioxol-5-yl)ethyl}thio]acetic acid as a colorless crystal according to the same procedure as that described in Example 27.
m.p.: 98° to 99° C.
$^1$H-NMR(400MHz,DMSO-d$_6$)δ;
1.10(t,J=7.5Hz,3H), 2.49~2.54(m,2H),
2.68~2.77(m,4H), 3.11(s,2H), 5.92(s,
2H), 6.73(s,1H), 6.76(s,1H), 7.01(s,1H),
7.43(s,1H)
MS(FD) m/z;167(MH$^-$)

Example 32

N,N-dimethyl-[{1-(6-methyl-1,3-benzodioxol-5-yl)ethyl}thio]acetamide

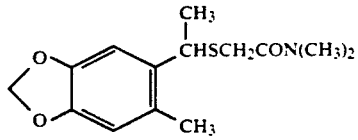

2.6 g of [{1-(6-methyl-1,3-benzodioxol-5-yl)ethyl}thio] acetic acid was dissolved in 20 ml of benzene, followed by the addition of 1.4 ml of thionyl chloride. The obtained mixture was heated under reflux for one hour and concentrated in a vacuum to obtain an acid chloride derivative as a brown oil.

Separately, 2.0 g of sodium hydroxide was dissolved in 10 ml of water to obtain a solution. Dimethylamine hydrochloride was added to the solution under cooling with ice. The above derivative was dropwise added to the obtained mixture. The obtained mixture was stirred at a room temperature overnight, followed by the addition of water. The mixture was extracted with chloroform. The organic layer was dried over magnesium sulfate and distilled to remove the solvent. The residue was purified by silica gel column chromatography (ethyl acetate/hexane=5:95) to obtain 2.1 g of the title compound as a colorless oil.
$^1$H-NMR(90MHz, CDCl$_3$) δ;
1.53(d,J=7Hz,3H), 2.27(s,3H), 2.90(s,
3H), 2.95(s,3H), 3.08 and 3.19(ABq,J=
14Hz,2H), 4.34(q,J=7Hz,1H), 5.85(s,2H),
6.55(s,1H), 6.94(s,1H)
MS m/z; 281(M$^-$)

Example 33

N,N-Diethyl-[{2-(6-ethyl-1,3-benzodioxol-5-yl)ethyl}thio] acetamide

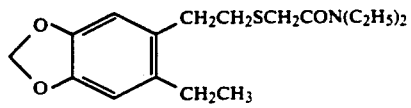

2.1 g of the title compound was prepared from 2.0 g of [{2-(6-ethyl-1,3-benzodioxol-5-yl)ethyl}thio]acetic acid by using 2.7 g of diethylamine as a pale yellow oil according to the same procedure as that described in Example 32.
$^1$H-NMR(400MHz,DMSO-d$_6$) δ;
1.01(t,J=7.1Hz,3H), 1.10(t,J=7.5Hz,3H),
1.12(t,J=7.1Hz, 3H), 2.52(q,J=7.3Hz,2H),
2.68~2.78(m,4H), 3.25(q,J=7.0Hz,2H),
3.33(q,J=7.0Hz,2H), 3.39(s,2H), 5.92(s,
2H), 6.72(s,1H), 6.76(s,1H)
MS(FD) m/z;323(M$^-$)

Example 34

N-[2-[{(1,3-Benzodioxol-5-yl)butyl}thio]-1-oxoethyl]aminoacetic acid

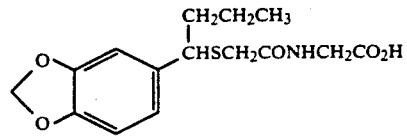

1.4 g of [{(1,3-benzodioxol-5-yl)butyl}thio]acetic acid was dissolved in 10 ml of benzene, followed by the addition of 0.8 ml of thionyl chloride. The obtained mixture was heated under reflux for 1.5 hours and concentrated in a vacuum to obtain a residue. Separately, 0.43 g of sodium hydroxide was dissolved in 4 ml of water, followed by the addition of 0.8 g of glycine to obtain a mixture. The above residue was dissolved in a small amount of tetrahydrofuran to obtain a solution. This solution was dropwise added to the above mixture under cooling with ice/water. The obtained mixture was stirred for 30 minutes, followed by the addition of water. The mixture was acidified with concentrated hydrochloric acid and extracted with chloroform. The organic layer was dried over magnesium sulfate and distilled to remove the solvent. Thus, a brown oil was obtained. This oil was crystallized from isopropyl ether to obtain 1.0 g of the title compound as a light brown crystal.
m.p.: 95° to 96° C.
$^1$H-NMR(90MHz, CDCl$_3$) δ; 0.87(m,3H),
1.10~1.50(m,2H), 1.68~1.93(m,2H), 3.02 and
3.07(ABq,J=17Hz, 2H), 3.76(t,J=7Hz,1H),
3.99(t,J=5Hz, 2H), 5.88(s,2H), 6.63~6.75(m,3H),
7.16(m,1H), 7.49(brs,1H)

Example 35

Sodium N-[2-[{(1,3-benzodioxol-5-yl)butyl}thio]-1oxoethyl]aminoacetate

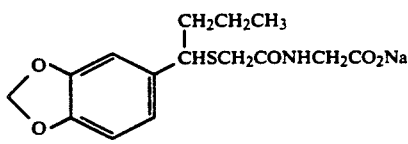

0.5 g of the title compound was prepared from 0.5 g of N-[2-{(1,3-benzodioxol-5-yl)butyl}thio3-1oxoethyl]aminoacetic acid as a white powder according to the same procedure as that described in Example 8.
m.p.: 264° to 270° C. (decomp.)
$^1$H-NMR(400MHz,DMSO-d$_6$)δ;
0.82(t,J=7.3Hz,3H), 1.11~1.28(m,2H), 1.67~1.80(m,2H), 2.80 and 3.03(ABq,J=15.0Hz,2H), 3.25(d,J=4.0Hz,2H), 3.91(dd, J=6.6Hz and 8.8Hz, 1H), 5.99(s,2H), 6.73 (dd,J=1.5Hz and 7.7Hz,1H), 6.80(d,J=7.7 Hz,1H), 6.87(d,J=1.5Hz,1H), 7.44(brs,1H) MS(FAB) m/z;370(MNa−), 348(MH−)

What is claimed is:

1. A benzodioxole derivative having the formula (I) or a pharmaceutically acceptable salt thereof:

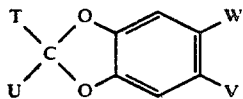 (I)

wherein T is hydrogen, U is hydrogen, V is $R^3$ and W is

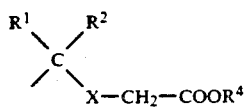

wherein $R^1$ and $R^2$ may be the same or different and each represents a hydrogen atom, an alkyl, benzyl, phenethyl or a heteroarylalkyl group wherein the heteroaryl group is a five or six membered ring containing nitrogen, $R^3$ represents a hydrogen atom or a lower alkyl, benzyl orphenethyl, or heteroarylalkyl group wherein the heteroaryl group is a five or six membered ring containing nitrogen, $R^4$ represents a hydrogen atom or a lower alkyl group, or $R^2$ and $R^3$ may join together to form a 4 to 6-membered ring and X represents a group of the formula:

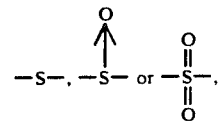

with the proviso that $R^1$ is an alkyl, benzyl, phenethyl, or heteroarylalkyl group having at least 3 carbon atoms when X is —S— group and $R^3$ and $R^2$ are each a hydrogen atom.

2. The benzodioxole derivative according to claim 1, wherein X is —S— and $R^3$ is a hydrogen atom.

3. The benzodioxole derivative according to claim 1, wherein W is —CH(n—CH$_3$H$_7$)—S—CH$_2$COOH.

4. The benzodioxole derivative according to claim 1, wherein W is —C(CH$_3$)$_2$—S—CH$_2$COOH.

* * * * *